United States Patent [19]
Reed et al.

[11] Patent Number: 5,459,038
[45] Date of Patent: Oct. 17, 1995

[54] DETERMINATION OF GENETIC SEX IN RUMINANTS USING Y-CHROMOSOME SPECIFIC POLYNUCLEOTIDES

[75] Inventors: Kenneth C. Reed, Monash; Eric A. Lord, North Lyneham; Klaus I. Matthaei, Scullin; David A. Mann, Higgins; Sandra Beaton, MacGregor; Charles M. Herr, Tabletop; Margaret E. Matthews, Reid, all of Australia

[73] Assignee: Advanced Riverina Holdings, Ltd., New South Wales, Australia

[21] Appl. No.: 175,679

[22] Filed: Dec. 30, 1993

Related U.S. Application Data

[63] Continuation of Ser. No. 3,695, Jan. 13, 1993, abandoned, which is a continuation of Ser. No. 548,903, filed as PCT/AU89/00029, Jan. 29, 1989, abandoned.

[30]     Foreign Application Priority Data

Jan. 29, 1988 [AU] Australia ................... PI6476

[51] Int. Cl.$^6$ ............... C12Q 1/70; C07H 21/04; C12P 19/34
[52] U.S. Cl. ............... 435/6; 435/91.2; 536/23.1; 536/24.31; 536/24.33; 935/6; 935/8; 935/17; 935/78
[58] Field of Search ............ 435/6, 91.2; 436/501, 436/63; 935/8, 78; 536/23.1, 23.5, 24.31, 24.33

[56]               References Cited

U.S. PATENT DOCUMENTS 4,769,319   9/1988   Ellis et al. ................ 436/501

OTHER PUBLICATIONS

Bethesda Research Laboratories Catalogue and Reference Guide (1985) p. 59.
Derwent Abstract Acc. No. 87-244362/35, Bishop et al, European Pat. No. 235046, Sep. 2, 1987.

*Primary Examiner*—Margaret Parr
*Assistant Examiner*—Carla Myers
*Attorney, Agent, or Firm*—Bacon & Thomas

[57]               ABSTRACT

Nucleic acid isolates capable of hybridizing only to the Y-chromosome specific DNA sequences of cattle, sheep and goats are described, as are methods for the determination of the sex chromosome constitution of a tissue or cell sample.

17 Claims, 66 Drawing Sheets

FIGURE 1a

```
            10        20        30        40        50
GGATCCCACAGGTGGACAAGCCACAACCTTGCACACCCACACATCACCAC
CCTAGGGTGTCCACCTGTTCGGTGTTGGAACGTGTGGGTGTGTAGTGGTG
BamHI
            60        70        80        90       100
AGGAACCACGTTTCACAAGTGGTGTCAAGGTAATTCTACTTAGTGGTCAC
TCCTTGGTGCAAAGTGTTCACCACAGTTCCATTAAGATGAATCACCAGTG 110       120       130       140       150
TGTGTTCAAGAAGTAGGGGGGTCCTGAAAGGAAAATATCAACTTGCAGTG
ACACAAGTTCTTCATCCCCCCAGGACTTTCCTTTTATAGTTGAACGTCAC 160       170       180       190       200
GGACCATGGATGGCTCTGCAACAGCACCTGTCAGGATAGGGAGGAGGGAA
CCTGGTACCTACCGAGACGTTGTCGTGGACAGTCCTATCCCTCCTCCCTT 210       220       230       240       250
AAGATTCCTGCGCCGCCTCCTCTTCCTGAGCAGCAGACTTCAAAGAGCAG
TTCTAAGGACGCGGCGGAGGAGAAGGACTCGTCGTCTGAAGTTTCTCGTC 260       270       280       290       300
CATAAAGGGTACAGGTATGGCCCAGAAGCAAGGGAGGTCCAAGATGACGG
GTATTTCCCATGTCCATACCGGGTCTTCGTTCCCTCCAGGTTCTACTGCC 310       320       330       340       350
CGATCCTCCAAGCCAAGTCAGGCTTCCTCCTCTGATGGTACTTGAACATG
GCTAGGAGGTTCGGTTCAGTCCGAAGGAGGAGACTACCATGAACTTGTAC 360       370       380       390       400
AACTGGAAGTAGGCCCTGCAGTTTTTCTTATGCTCAGAGCTCAGTTCCAC
TTGACCTTCATCCGGGACGTCAAAAAGAATACGAGTCTCGAGTCAAGGTG 410       420       430       440       450
CAGCAGGGCAACCAGTGCCTGCAGCGCATCTTGCCCTGGAAGCTCAGTAG
GTCGTCCCGTTGGTCACGGACGTCGCGTAGAACGGGACCTTCGAGTCATC 460       470       480       490       500
TGCTCCCGGGCCTTTTCTGGCCCTACTCCTCCACCATCTTCTCAGCTCCT
ACGAGGGCCCGGAAAAGACCGGGATGAGGAGGTGGTAGAAGAGTCGAGGA 510       520       530       540       550
GGAAGAACCCCTATTGCTGCTGCTCATCTGCCACAACCTCCACCTCCTCC
CCTTCTTGGGGATAACGACGACGAGTAGACGGTGTTGGAGGTGGAGGAGG 560       570       580       590       600
ATGATGTCTTCCACAAGCAGCTGGAACAACCACCCAATCCCCACCACGTC
TACTACAGAAGGTGTTCGTCGACCTTGTTGGTGGGTTAGGGGTGGTGCAG
```

FIGURE 1b

```
         610        620        630        640        650
TCCGACCACCAGGGGCTCACCATCGTCCACTGCCTCCACCCTGCATAGGG
AGGCTGGTGGTCCCCGAGTGGTAGCAGGTGACGGAGGTGGGACGTATCCC 660        670        680        690        700
TGGCTCTTTTGCCTGGCATGACAATTTGTGGCTGTAAGTTCCCAGCCTCA
ACCGAGAAAACGGACCGTACTGTTAAACACCGACATTCAAGGGTCGGAGT 710        720        730        740        750
AAAAGCCTGAGGATGGCAGGCCACCAACCCCAGCGCCCTGAAATCGGGGC
TTTTCGGACTCCTACCGTCCGGTGGTTGGGGTCGCGGGACTTTAGCCCCG 760        770        780        790        800
TCACAACTAGGAAGGTCTGGGGTCCCAGGATGCTCCTACATTCCTCTGAC
AGTGTTGATCCTTCCAGACCCCAGGGTCCTACGAGGATGTAAGGAGACTG 810        820        830        840        850
CAACCTTCACACTCCTCTTGGCCCTGATCGTGACCCCAGGCTGGGGAAGA
GTTGGAAGTGTGAGGAGAACCGGGACTAGCACTGGGGTCCGACCCCTTCT 860        870        880        890        900
TGTGAAGGGATGGGACATAATGGCACAACAAGTGGTGTGCAAATGCGGGT
ACACTTCCCTACCCTGTATTACCGTGTTGTTCACCACACGTTTACGCCCA 910        920        930        940        950
CAGGCTTCAGTAATCCTGTGGGACCCATTAGCTGTTTGAGGGCAGGGAGG
GTCCGAAGTCATTAGGACACCCTGGGTAATCGACAAACTCCCGTCCCTCC 960        970        980        990       1000
GAGGGGGATGGTAGGGAAGCGGTAGCTGGTGTGTGTCCGGTGGCCTGAGG
CTCCCCCTACCATCCCTTCGCCATCGACCACACACAGGCCACCGGACTCC 1010       1020       1030       1040       1050
CTGAAGAAATGGGTGACAGACAGCGTGGGACAGGGTGAAGGGGCCCTGGG
GACTTCTTTACCCACTGTCTGTCGCACCCTGTCCCACTTCCCCGGGACCC 1060       1070       1080       1090       1100
GAAATCACCCGAATAGGCAGATCATTAGGTTGTGAGCCATGCACAGGCTG
CTTTAGTGGGCTTATCCGTCTAGTAATCCAACACTCGGTACGTGTCCGAC 1110       1120       1130       1140       1150
CTGGCCCAAATGTAGTTCAATGGCCAAGATCGTGGAGGGCGGCACGCTTA
GACCGGGTTTACATCAAGTTACCGGTTCTAGCACCTCCCGCCGTGCGAAT 1160       1170       1180       1190       1200
TGGACACGCCACTGAAACGTAGGGCATCTTCCATGGTTCCTGTTCGATGG
ACCTGTGCGGTGACTTTGCATCCCGTAGAAGGTACCAAGGACAAGCTACC
```

FIGURE 1c

```
       1210      1220      1230      1240      1250
CACACCATATACCGCTCCAGAAAGGTAATGGGTTTTGCATCTGCTGATAC
GTGTGGTATATGGCGAGGTCTTTCCATTACCCAAAACGTAGACGACTATG 1260      1270      1280      1290      1300
CCCAGGTGCTGTCATTGACCGGGCTCTGAAAATTCCAACGACGGGTTCCT
GGGTCCACGACAGTAACTGGCCCGAGACTTTTAAGGTTGCTGCCCAAGGA 1310      1320      1330      1340      1350
GCTTCACAGTCTGAACAGCACACTCCTGTGTCCCTCAGGACCCTCAATAA
CGAAGTGTCAGACTTGTCGTGTGAGGACACAGGGAGTCCTGGGAGTTATT 1360      1370      1380      1390      1400
CTGAGAAGTCTCCCTGAATATCCAAAGGATAATCGGGCTGCACGAGGCTG
GACTCTTCAGAGGGACTTATAGGTTTCCTATTAGCCCGACGTGCTCCGAC 1410      1420      1430      1440      1450
GATACCTTTTTCCCATGGGACAGAGAACATGTTGATGTCCAGATGCTAGA
CTATGGAAAAAGGGTACCCTGTCTCTTGTACAACTACAGGTCTACGATCT 1460      1470      1480      1490      1500
GGAGAAGGGAAAACCCCCACTGTTTGCTACAGTTGATCTCCACTGTTCAG
CCTCTTCCCTTTTGGGGGTGACAAACGATGTCAACTAGAGGTGACAAGTC 1510      1520      1530      1540      1550
GGACACCAGAGCCTTAGGGTATCGAGCTGGCTCTGTGTCTCTTCATCTCT
CCTGTGGTCTCGGAATCCCATAGCTCGACCGAGACACAGAGAAGTAGAGA 1560      1570      1580      1590      1600
GCTTCTGGCATTTCACTGTTTTGGGCAATCCTTCTATGTGTTTACCAAGG
CGAAGACCGTAAAGTGACAAAACCCGTTAGGAAGATACACAAATGGTTCC 1610      1620      1630      1640      1650
GCTGGTGTCTGTCTGTCTCCATCTCTCTAAGTGGTGCTCTTGCTGTCTGC
CGACCACAGACAGACAGAGGTAGAGAGATTCACCACGAGAACGACAGACG 1660      1670      1680      1690      1700
CAATCTCTGGACACCAGTGCTCATATGAGAAGGTTATATGAGAAGGCAAG
GTTAGAGACCTGTGGTCACGAGTATACTCTTCCAATATACTCTTCCGTTC 1710      1720      1730      1740      1750
CGCTGCTCCTCCTTAGTGAGTTGCACCCATGGAGATCAGACTTTGTCAGT
GCGACGAGGAGGAATCACTCAACGTGGGTACCTCTAGTCTGAAACAGTCA 1760      1770      1780      1790      1800
CCACACATTCGGAGAGTGCTTTCTCAAACTTGAAAGTCAACAGTAGGCAG
GGTGTGTAAGCCTCTCACGAAAGAGTTTGAACTTTCAGTTGTCATCCGTC
```

FIGURE 1d

```
        1810      1820      1830      1840      1850
    TCACTGATAAAGTGCTTTCTCAAACTTGAAAGTCAACAGTGGGCAGTCAC
    AGTGACTATTTCACGAAAGAGTTTGAACTTTCAGTTGTCACCCGTCAGTG 1860      1870      1880      1890      1900
    TGCTAAACTGCAGAAAGTGTCTCCCTCGCTGGACAGACATGAATACTGCA
    ACGATTTGACGTCTTTCACAGAGGGAGCGACCTGTCTGTACTTATGACGT 1910      1920      1930      1940      1950
    AAGGCCTCGGGTAGCTTGGCCACACTTTGCACAGATGGAGAACTGGGGCA
    TTCCGGAGCCCATCGAACCGGTGTGAAACGTGTCTACCTCTTGACCCCGT 1960      1970      1980      1990      2000
    TGGCTTGTGGCTTGAGGGAACTCCCTGAACATTATTTGAATACCTGCCAG
    ACCGAACACCGAACTCCCTTGAGGGACTTGTAATAAACTTATGGACGGTC 2010      2020      2030      2040      2050
    GGAGATGGTAAGGACAGCTCCCCATTAAGTTCCATTACACTTGTGCCAGA
    CCTCTACCATTCCTGTCGAGGGGTAATTCAAGGTAATGTGAACACGGTCT 2060      2070      2080      2090      2100
    AACATGCACGTCTGCCAATTTACCCTATCAAGGCCCTTTCTAAGTGGTTC
    TTGTACGTGCAGACGGTTAAATGGGATAGTTCCGGGAAAGATTCACCAAG 2110      2120      2130      2140      2150
    TGTTCTCCACGTGAGAACACATTCAAGCCTGCCTGGTCACCTAAGCCTGT
    ACAAGAGGTGCACTCTTGTGTAAGTTCGGACGGACCAGTGGATTCGGACA 2160      2170      2180      2190      2200
    GGGGCTGGGAGCAGCAAGAGGATCAAGATAAGCCATCCATCCTATAGTCC
    CCCCGACCCTCGTCGTTCTCCTAGTTCTATTCGGTAGGTAGGATATCAGG 2210      2220      2230      2240      2250
    TGATACCCAATATATGTGTTCTGCAAAGAGTACAAAGAGTGATGATTCAA
    ACTATGGGTTATATACACAAGACGTTTCTCATGTTTCTCACTACTAAGTT 2260      2270      2280      2290      2300
    ACTGGAAGACTGCAGGTAGCAGGTGCTTATGCTGCAGTTCTGGTCCATCA
    TGACCTTCTGACGTCCATCGTCCACGAATACGACGTCAAGACCAGGTAGT 2310      2320      2330      2340      2350
    CTGAAACCACACAAAAAAGGCAAGGGCTGGTCATGCTCATGGTAAGGTCA
    GACTTTGGTGTGTTTTTTCCGTTCCCGACCAGTACGAGTACCATTCCAGT 2360      2370      2380      2390      2400
    GGGAAAGTATGCCTGACACTTGGGAAGGATGGAAAGGCCCTTGTATCCAG
    CCCTTTCATACGGACTGTGAACCCTTCCTACCTTTCCGGGAACATAGGTC
```

FIGURE 1e

```
        2410      2420      2430      2440      2450
GTGTTCAAGGGGCTGTGGAGTCACCCACCATGGCTTCTGTGTCTGGGATT
CACAAGTTCCCCGACACCTCAGTGGGTGGTACCGAAGACACAGACCCTAA 2460      2470      2480      2490      2500
GCAGCCTGTTCTGTGTCTCAGATCTGCACTGTCACTGGTTGCCGCCAGGC
CGTCGGACAAGACACAGAGTCTAGACGTGACAGTGACCAACGGCGGTCCG 2510      2520      2530      2540      2550
ACTTTATTCCTGCCTCTCCTTTCTGCCAGGCATCCTTGCTGTATCACTGT
TGAAATAAGGACGGAGAGGAAAGACGGTCCGTAGGAACGACATAGTGACA 2560      2570      2580      2590      2600
GATTCCACTCAGAACTTGCTCACTCAGTGAGATAACGGGGATCAGTAACT
CTAAGGTGAGTCTTGAACGAGTGAGTCACTCTATTGCCCCTAGTCATTGA 2610      2620      2630      2640      2650
ACCCTGGCCTCAGTGCTTCTGCTAGCTAGAGTTTATGTACCTTTCCCTAT
TGGGACCGGAGTCACGAAGACGATCGATCTCAAATACATGGAAAGGGATA 2660      2670      2680      2690      2700
GGCTTTCATGTTTTTGTATTCAACTTCCATCAACTGGTTAGGTCAGTTCT
CCGAAAGTACAAAAACATAAGTTGAAGGTAGTTGACCAATCCAGTCAAGA 2710      2720      2730      2740      2750
GACAGCTCATACTCACAAGCGTACTGGCAGGCACATCTGCACACACATGC
CTGTCGAGTATGAGTGTTCGCATGACCGTCCGTGTAGACGTGTGTGTACG 2760      2770      2780      2790      2800
CTGAACACACTAACGTCCCTGAGGAGGAAACTTTCTAACTCTGTGACAGC
GACTTGTGTGATTGCAGGGACTCCTCCTTTGAAAGATTGAGACACTGTCG 2810      2820      2830      2840      2850
ACCAAGAGTGTTTGGACCACCCATGCTTCACTGATTTACTAAATGCCAAG
TGGTTCTCACAAACCTGGTGGGTACGAAGTGACTAAATGATTTACGGTTC 2860      2870      2880      2890      2900
ACTTTTTCAGTCGCTCTCATTGGGGCCAGGTAGGTCTTCATACAATCAGC
TGAAAAAGTCAGCGAGAGTAACCCCGGTCCATCCAGAAGTATGTTAGTCG 2910      2920      2930      2940      2950
TATACCTGCTTGCCCACACAGCTGAAGTGCCAATGAAGCCTGTCCTTGGT
ATATGGACGAACGGGTGTGTCGACTTCACGGTTACTTCGGACAGGAACCA 2960      2970      2980      2990      3000
TGGGCCCAAAGACATCTAAGAGAGTCAGTGGGAAGGCAGGGTCCATCTGA
ACCCGGGTTTCTGTAGATTCTCTCAGTCACCCTTCCGTCCCAGGTAGACT
```

FIGURE 1f

```
        3010      3020      3030      3040      3050
GTGTCACCTGGGGCAGATCCGCTATAACAAAATCAGAGAACCTGCTCCAG
CACAGTGGACCCCGTCTAGGCGATATTGTTTTAGTCTCTTGGACGAGGTC 3060      3070      3080      3090      3100
CAAGACTGCCAGAATCCTCCCTCAGGTGCAGCCGTGCTCCTTTGCCCATC
GTTCTGACGGTCTTAGGAGGGAGTCCACGTCGGCACGAGGAAACGGGTAG 3110      3120      3130      3140      3150
TAGACCCACAGCCAGTGGCATGACCCCAGAGGAAAGGAATTC
ATCTGGGTGTCGGTCACCGTACTGGGGTCTCCTTTCCTTAAG
                                        EcoRI
```

FIGURE 2a

```
          10        20        30        40        50
GGATCCCACAGGTCGACACTCCACAACCTTGCACACCCACACTCACCACC
CCTAGGGTGTCCAGCTGTGAGGTGTTGGAACGTGTGGGTGTGAGTGGTGG
BamHI
          60        70        80        90       100
CCAGGAACCACATTTCACAAGTGATGTCAAGGTAATTCTACTTAGTGGTC
GGTCCTTGGTGTAAAGTGTTCACTACAGTTCCATTAAGATGAATCACCAG 110       120       130       140       150
ACTGAGTTCAAGAAGTAGGGGGGTCCTGAAAGGAAAATATCAACTTGCAG
TGACTCAAGTTCTTCATCCCCCCAGGACTTTCCTTTTATAGTTGAACGTC 160       170       180       190       200
TGGGACGATGGATGGCTCCGCAACAGCACCTGTCAGGATAGGGAGCAGGG
ACCCTGCTACCTACCGAGGCGTTGTCGTGGACAGTCCTATCCCTCGTCCC 210       220       230       240       250
AAAAGGTTCCTGCGCCGCCTCCTCTTCCTGAGCAGCAGACTTCAAAGAGC
TTTTCCAAGGACGCGGCGGAGGAGAAGGACTCGTCGTCTGAAGTTTCTCG 260       270       280       290       300
AGCAGAAAGGATACAGCTACAGCCCAGAAGCAAGGGATGCCCCAGGTGAT
TCGTCTTTCCTATGTCGATGTCGGGTCTTCGTTCCCTACGGGGTCCACTA 310       320       330       340       350
GGCGATCCTCCAAGCCAAGTCAGGCTTCCTCCTCTGATGGTTCTTGCACA
CCGCTAGGAGGTTCGGTTCAGTCCGAAGGAGGAGACTACCAAGAACGTGT 360       370       380       390       400
TGAACTGGAAGTAGGCCCTGCAGTTCTTCTTATGCTCAGAGCTCAGTTCC
ACTTGACCTTCATCCGGGACGTCAAGAAGAATACGAGTCTCGAGTCAAGG 410       420       430       440       450
ACCAGCAGGGCAGCCAGTGCCTGCAGCTCATCTTGCCCTGGAAGCTCACT
TGGTCGTCCCGTCGGTCACGGACGTCGAGTAGAACGGGACCTTCGAGTGA 460       470       480       490       500
AGTGCTCCCGGGCCTTCCCTGGCTCTGCTCCTCCACCGTCTTCTCAGCTC
TCACGAGGGCCCGGAAGGGACCGAGACGAGGAGGTGGCAGAAGAGTCGAG 510       520       530       540       550
CTGGAAGAACCCCTATTGCTGCTCCTCATCTGCCACAACCTCCACCTCCT
GACCTTCTTGGGGATAACGACGAGGAGTAGACGGTGTTGGAGGTGGAGGA 560       570       580       590       600
CCATGACGTCTTCCGCAAGCAGCTGGAACCACCACCCAATCCCCACCACG
GGTACTGCAGAAGGCGTTCGTCGACCTTGGTGGTGGGTTAGGGGTGGTGC
```

FIGURE 2b

```
           610        620        630        640        650
    TCTCCGTCCACCAGGGGCTCACCGTCGTCCACCGCCTCCACCCTGCATAG
    AGAGGCAGGTGGTCCCCGAGTGGCAGCAGGTGGCGGAGGTGGGACGTATC 660        670        680        690        700
    CGTGGCTCCTTTGCCTGGAATGACAACTTGTGGCTGTAAGGTCCCAGCCT
    GCACCGAGGAAACGGACCTTACTGTTGAACACCGACATTCCAGGGTCGGA 710        720        730        740        750
    CAAAAAGCCTGAGGATGGCAGGCCACCAACCCCAGCGCCCTGAAACCGGA
    GTTTTTCGGACTCCTACCGTCCGGTGGTTGGGGTCGCGGGACTTTGGCCT 760        770        780        790        800
    GCTCACAACTAGGAAGGTCTGGGGTCTCAGGATGCTCCTGCATTCCTCTG
    CGAGTGTTGATCCTTCCAGACCCCAGAGTCCTACGAGGACGTAAGGAGAC 810        820        830        840        850
    ACGGCCTTTCACACGCCTCTTGGCCCTGATCGTGACCCCAGGCTGGGGCA
    TGCCGGAAAGTGTGCGGAGAACCGGGACTAGCACTGGGGTCCGACCCCGT 860        870        880        890        900
    GATGCCAAGGGATGGGACATAATAGCACAGCAAGTGGTGTGCAAATGCGG
    CTACGGTTCCCTACCCTGTATTATCGTGTCGTTCACCACACGTTTACGCC 910        920        930        940        950
    CTCAGGTTTCAGTAATCCTGTGGGACCCACTAGCTCTTTGGGGGCGGGGA
    GAGTCCAAAGTCATTAGGACACCCTGGGTGATCGAGAAACCCCCGCCCCT 960        970        980        990       1000
    GTGAGGGGGATGGTAGGGAAGCGGGGGCTGGTGTGTGTCCGGTGGCCTGA
    CACTCCCCCTACCATCCCTTCGCCCCCGACCACACACAGGCCACCGGACT 1010       1020       1030       1040       1050
    GGCTGAAGAAAGGGGTGGCAGACAGCATGGGACAGGGTGAACAGGCCCTG
    CCGACTTCTTTCCCCACCGTCTGTCGTACCCTGTCCCACTTGTCCGGGAC 1060       1070       1080       1090       1100
    GGGAAATCAGCCGAATAGGCGGATCCCTAGGCCGTGAGCCACGGATAGGC
    CCCTTTAGTCGGCTTATCCGCCTAGGGATCCGGCACTCGGTGCCTATCCG
                                  BamHI
          1110       1120       1130       1140       1150
    TGCTGGCCCAAATCTAGTCCAATGGCTGAGAGAGTGGTGGGTGGCACCCT
    ACGACCGGGTTTAGATCAGGTTACCGACTCTCTCACCACCCACCGTGGGA 1160       1170       1180       1190       1200
    TCTGGACACGCCCCTCAAACGTAGGAAGTCTTCCACAGTTCCTGGGCTAC
    AGACCTGTGCGGGGAGTTTGCATCCTTCAGAAGGTGTCAAGGACCCGATG
```

FIGURE 2c

```
         1210      1220      1230      1240      1250
    AGCGCACCCACATGGCATATACCGCTCCAGGGAATAATGGGTTTTGCATC
    TCGCGTGGGTGTACCGTATATGGCGAGGTCCCTTATTACCCAAAACGTAG 1260      1270      1280      1290      1300
    TGCTGATACTCCAGGCGCTGTCATTGTCCGGACTCTGGAAATCCCAACGA
    ACGACTATGAGGTCCGCGACAGTAACAGGCCTGAGACCTTTAGGGTTGCT 1310      1320      1330      1340      1350
    CGGGTTCCTGCTTCACAGTCTGAACAGCTTACTCCTGTGTCCCTCAGGAC
    GCCCAAGGACGAAGTGTCAGACTTGTCGAATGAGGACACAGGGAGTCCTG 1360      1370      1380      1390      1400
    CCTCAATAACTGAGAAATTTCCCTGAGGATTCAAAGGATAAACAGGGACT
    GGAGTTATTGACTCTTTAAAGGGACTCCTAAGTTTCCTATTTGTCCCTGA 1410      1420      1430      1440      1450
    CCACGTGCCTGGATACTTTTTCTCCATGGGACACAGAACCTGTTGTCCGG
    GGTGCACGGACCTATGAAAAGAGGTACCCTGTGTCTTGGACAACAGGCC 1460      1470      1480      1490      1500
    ATGCTAGGGGAGAAGGGAAAAACCACACTGTTGGCTACAGTTGATCTCCA
    TACGATCCCCTCTTCCCTTTTTGGTGTGACAACCGATGTCAACTAGAGGT 1510      1520      1530      1540      1550
    CTGTTCAGGGACACCAGAGCCTTAGGGTACAGAGCTGGCTCTGTGTCTCT
    GACAAGTCCCTGTGGTCTCGGAATCCCATGTCTCGACCGAGACACAGAGA 1560      1570      1580      1590      1600
    TCATCTCTGCTTCTGGCATAGCACTGTTTTGGGCAACCCTTCCATGTGTG
    AGTAGAGACGAAGACCGTATCGTGACAAAACCCGTTGGGAAGGTACACAC 1610      1620      1630      1640      1650
    TACCAAGGGCTGGTGTCTGTTTGTCTCCATCTCTCTAAGTGGTGCTCTTG
    ATGGTTCCCGACCACAGACAAACAGAGGTAGAGAGATTCACCACGAGAAC 1660      1670      1680      1690      1700
    CTGTCTGTCACTCTCTGCACACCAGTGCTCATACGAGAAGTTTATATGAG
    GACAGACAGTGAGAGACGTGTGGTCACGAGTATGCTCTTCAAATATACTC 1710      1720      1730      1740      1750
    AAGGCAAGCCCTGCTCCTCCTTAGTGAGTTGCACCCATGGGAGATCAGAC
    TTCCGTTCGGGACGAGGAGGAATCACTCAACGTGGGTACCCTCTAGTCTG 1760      1770      1780      1790      1800
    TTTGTTAGTCCACACGTTCGGAGAGTGCTTTCTCAAACTTGAAAGTCCAC
    AAACAATCAGGTGTGCAAGCCTCTCACGAAAGAGTTTGAACTTTCAGGTG
```

FIGURE 2d

```
        1810      1820      1830      1840      1850
AGTGTGCGGTCACTGCTGAACTGCAGAAGGTGCGGAGTGACCCTCCCTCC
TCACACGCCAGTGACGACTTGACGTCTTCCACGCCTCACTGGGAGGGAGG 1860      1870      1880      1890      1900
ATCGCTGGACAGACGTGAATAGTGCAAAGGCCTCAGGTAGCTTGGCCACA
TAGCGACCTGTCTGCACTTATCACGTTTCCGGAGTCCATCGAACCGGTGT 1910      1920      1930      1940      1950
CTTTGCACAGGTGGAGAAATGGGGCATGGCCTGGGGCCTGAGGGCACTCC
GAAACGTGTCCACCTCTTTACCCCGTACCGGACCCCGGACTCCCGTGAGG 1960      1970      1980      1990      2000
CTGAACATTATTTGAATACCTGCCAGGGAGATGGTAAGGACAGCTCCCCA
GACTTGTAATAAACTTATGGACGGTCCCTCTACCATTCCTGTCGAGGGGT 2010      2020      2030      2040      2050
TTAAGTTCCATGACACACTGGTGCCAGAAACATGCATGGCTGCCAGTTTA
AATTCAAGGTACTGTGTGACCACGGTCTTTGTACGTACCGACGGTCAAAT 2060      2070      2080      2090      2100
CCCTATCGAGGCCCTTTCAAAGCGGTTCTGTTCTCCATGTGAGAACACAT
GGGATAGCTCCGGGAAAGTTTCGCCAAGACAAGAGGTACACTCTTGTGTA 2110      2120      2130      2140      2150
TCAAGCCTGCCCGGTCACCCAAGCCTGTGGGGCTGGGAGCAGCAAGAGGA
AGTTCGGACGGGCCAGTGGGTTCGGACACCCCGACCCTCGTCGTTCTCCT 2160      2170      2180      2190      2200
TCAAGATAAGCCATCCAGCCTATAGTCCTGAGAGCCAATATATGTGTTCT
AGTTCTATTCGGTAGGTCGGATATCAGGACTCTCGGTTATATACACAAGA 2210      2220      2230      2240      2250
GCAAAGAGTACAAAGAGTGATGATTCAGACTGGAAGACTGCAGGTAGCAG
CGTTTCTCATGTTTCTCACTACTAAGTCTGACCTTCTGACGTCCATCGTC 2260      2270      2280      2290      2300
GTGCTTATGCTGCAGTTCTGGTCCATCACTGAAACCACACAAAATAGGCA
CACGAATACGACGTCAAGACCAGGTAGTGACTTTGGTGTGTTTTATCCGT 2310      2320      2330      2340      2350
AGGGTTGCTCATGCTCATGGTAAGGTCAGGCAAAGTATGCCTGGCACTTG
TCCCAACGAGTACGAGTACCATTCCAGTCCGTTTCATACGGACCGTGAAC 2360      2370      2380      2390      2400
GGAAGGATGGAAAGGCCCTTGTATCAGGGTGTTCAAAGGGCTGTGGGGTC
CCTTCCTACCTTTCCGGGAACATAGTCCCACAAGTTTCCCGACACCCCAG
```

FIGURE 2e

```
          2410      2420      2430      2440      2450
      ACCCACCGTGGCTTCTGTGTCTGGGATTGCAACCTGTTCTGTGTCTCAGA
      TGGGTGGCACCGAAGACACAGACCCTAACGTTGGACAAGACACAGAGTCT 2460      2470      2480      2490      2500
      TCTTCTGCACTCTCACTGGTCACCCCCAGGCACTTTATTCCTGCCTCTCC
      AGAAGACGTGAGAGTGACCAGTGGGGGTCCGTGAAATAAGGACGGAGAGG 2510      2520      2530      2540      2550
      TTTCTGCCAGGAATCCTTGCTGGACCACTGTGATTCCACTCAGAACTTGC
      AAAGACGGTCCTTAGGAACGACCTGGTGACACTAAGGTGAGTCTTGAACG 2560      2570      2580      2590      2600
      TCACTCAGTGAGATAACGGGGATCAGTAAGTATGTCTACATATGTTCTGT
      AGTGAGTCACTCTATTGCCCCTAGTCATTCATACAGATGTATACAAGACA 2610      2620      2630      2640      2650
      GGGTTTGTGTATGTGTGTGTGTGCGCGCGCACGCGTGTGTGTGACTCC
      CCCAAACACATACACACACACACGCGCGCGTGCGCACACACACTGAGG 2660      2670      2680      2690      2700
      CACATCTGTTATTTTCGGAATCATTCACCTTTACAACAATAACTGTCAGC
      GTGTAGACAATAAAAGCCTTAGTAAGTGGAAATGTTGTTATTGACAGTCG 2710      2720      2730      2740      2750
      TAAGGTGGCTCTGATGTACTGTCTCTGGTCATTTCTGACTCAGAGGCTAA
      ATTCCACCGAGACTACATGACAGAGACCAGTAAAGACTGAGTCTCCGATT 2760      2770      2780      2790      2800
      TCCTCCTCAGATGCAGGCCTGAAGGAGACACACAGTCATGGCTGCGACAC
      AGGAGGAGTCTACGTCCGGACTTCCTCTGTGTCAGTACCGACGCTGTG 2810      2820      2830      2840      2850
      TTACAGGTGTGGCCCTGCCCGGACTCTACTCAGCTGTGCCTGTGGAGCCT
      AATGTCCACACCGGGACGGGCCTGAGATGAGTCGACACGGACACCTCGGA 2860      2870      2880      2890      2900
      GCCAATTGCCCAGTACCACACTTCCTTCAGGGTCCACCATTCTGTCCCCT
      CGGTTAACGGGTCATGGTGTGAAGGAAGTCCCAGGTGGTAAGACAGGGA 2910      2920      2930      2940      2950
      CGCCTCCACCCCTCCTCCTGCTCCTGCCTCTGCACCTCCCCTCCTCCTGA
      GCGGAGGTGGGGAGGAGGACGAGGACGGAGACGTGGAGGGGAGGAGGACT 2960      2970      2980      2990      3000
      GCACTGGACCACAACGAGTAGCAGAAAGGATACCACGTTGGCCTAGAAGC
      CGTGACCTGGTGTTGCTCATCGTCTTTCCTATGGTGCAACCGGATCTTCG
```

FIGURE 2f

```
         3010      3020      3030      3040      3050
    CAGGGATGCCCTGGATGTTGGCACTCTTCTGAGCCAAGCCACGCTTCCTC
    GTCCCTACGGGACCTACAACCGTGAGAAGACTCGGTTCGGTGCGAAGGAG 3060      3070      3080      3090      3100
    CTCTCATGACTCTTGCACATGAACCAAACGAAGGCCCTGCAGGTTTTCTC
    GAGAGTACTGAGAACGTGTACTTGGTTTGCTTCCGGGACGTCCAAAAGAG 3110      3120      3130      3140      3150
    AGGCTTAGAGCTAAGTTCCACTTACAAGGTCGCCAGTGCCAGCATCTCAT
    TCCGAATCTCGATTCAAGGTGAATGTTCCAGCGGTCACGGTCGTAGAGTA 3160      3170      3180      3190      3200
    CTAGTGCCGGGAGCTCACTCGGGCCTCCAGGCCTTTCCTGGCACTGCTCC
    GATCACGGCCCTCGAGTGAGCCCGGAGGTCCGGAAAGGACCGTGACGAGG 3210      3220      3230      3240      3250
    TCCAATGTCTTCTCCTCCAGCTCCAGGGAGGACCCTGTTTCTGTTATTCA
    AGGTTACAGAAGAGGAGGTCGAGGTCCCTCCTGGGACAAAGACAATAAGT 3260      3270      3280      3290      3300
    TCTGGCACAACCTCCACATCCTCAGTGATGTCCTCTGCAAGCAGCTGGAA
    AGACCGTGTTGGAGGTGTAGGAGTCACTACAGGAGACGTTCGTCGACCTT 3310      3320      3330      3340      3350
    ACCCCGTCTGATCCCTGCCACGACTCCGTCAACCTGGGCCTCGCTGTCCT
    TGGGGCAGACTAGGGACGGTGCTGAGGCAGTTGGACCCGGAGCGACAGGA 3360      3370      3380      3390      3400
    CTCCTGCCTCCACTCTGAAGAGGGTGGCATCTTCGCCTGGTGTGGCCACT
    GAGGACGGAGGTGAGACTTCTCCCACCGTAGAAGCGGACCACACCGGTGA 3410      3420      3430      3440      3450
    GGTGGCTGCAACGTCCCAGCCATGCACAGCATCACCAGGACAGGCTGTTG
    CCACCGACGTTGCAGGGTCGGTACGTGTCGTAGTGGTCCTGTCCGACAAC 3460      3470      3480      3490      3500
    CTGGCCAGATGCTAGGGGAGTAGGGAAAAACCCCACCGTTTGCCACATTG
    GACCGGTCTACGATCCCCTCATCCCTTTTTGGGGTGGCAAACGGTGTAAC 3510      3520      3530      3540      3550
    ATCTCCATTGTTCAGGGACACCAAATGGGAAAGGGGACGGAATGAATCAA
    TAGAGGTAACAAGTCCCTGTGGTTTACCCTTTCCCCTGCCTTACTTAGTT 3560      3570      3580      3590      3600
    ATTCCCCTTTTGATCACTCAACAGGAGGTCCTAGTCACCAGGTCTCATTC
    TAAGGGGAAAACTAGTGAGTTGTCCTCCAGGATCAGTGGTCCAGAGTAAG
```

FIGURE 2g

```
        3610            3620
ATGTTCCTGAAAAAGAAAGCTT
TACAAGGACTTTTTCTTTCGAA
                  HindIII
```

FIGURE 3a

```
         10        20        30        40        50
GGATCCCACAGGTCGACACTCCACAACCTTGCACACCCACACTCACCACC
CCTAGGGTGTCCAGCTGTGAGGTGTTGGAACGTGTGGGTGTGAGTGGTGG
BamHI
         60        70        80        90       100
CCAGGAACCACGTTTCACAAGTGATGTCAAGGTAATTCTACTTAGTGGTC
GGTCCTTGGTGCAAAGTGTTCACTACAGTTCCATTAAGATGAATCACCAG 110       120       130       140       150
ACTGTGTCCAAGAAGTAGGGGGGTCCTGAAAGGAAAATATCAACTTGCAG
TGACACAGGTTCTTCATCCCCCCAGGACTTTCCTTTTATAGTTGAACGTC 160       170       180       190       200
TGGGACGATGGATGGCTCCGCAACAGCACCTGTCAGGATAGGGAGCAGCG
ACCCTGCTACCTACCGAGGCGTTGTCGTGGACAGTCCTATCCCTCGTCGC 210       220       230       240       250
AAAAGGTTCCTGCGCCGCCTCCTCTTCCTGAGCAGCAGACTTCAAAGAGC
TTTTCCAAGGACGCGGCGGAGGAGAAGGACTCGTCGTCTGAAGTTTCTCG 260       270       280       290       300
AGCAGAAAGGATACAGCTATGGCCCAGAAGCAAGGGATGCCCCAGGTGAT
TCGTCTTTCCTATGTCGATACCGGGTCTTCGTTCCCTACGGGGTCCACTA 310       320       330       340       350
GGCGATCCTCCAAGCCACGTCAGGCTTCCTCCTCTGATGGTTCTTGCACA
CCGCTAGGAGGTTCGGTGCAGTCCGAAGGAGGAGACTACCAAGAACGTGT 360       370       380       390       400
TGAACTGGAAGTAGGCCCTGCAGTTCTTCTTATGCTCAGAGCTCAGTTCC
ACTTGACCTTCATCCGGGACGTCAAGAAGAATACGAGTCTCGAGTCAAGG 410       420       430       440       450
ACCAGCAGGGCAGCCAGTGCCTGCAGCGCATCTTGCCCTGGAAGCTCAGT
TGGTCGTCCCGTCGGTCACGGACGTCGCGTAGAACGGGACCTTCGAGTCA 460       470       480       490       500
AGTGCTCCCGGGCCTTCCCTGGCCCTGCTCCTCCACCGTCTTCTCAGCTC
TCACGAGGGCCCGGAAGGGACCGGGACGAGGAGGTGGCAGAAGAGTCGAG 510       520       530       540       550
CTGGAAAAACCCCTATTGCTGCTCCTCATCTGCCACAACCTCCACCTCCT.
GACCTTTTTGGGGATAACGACGAGGAGTAGACGGTGTTGGAGGTGGAGGA 560       570       580       590       600
CCATGACGTCTTCTGCAAGCAGCTGGAACCACCACCCAATCCCCACCACG
GGTACTGCAGAAGACGTTCGTCGACCTTGGTGGTGGGTTAGGGGTGGTGC
```

FIGURE 3b

```
            610        620        630        640        650
    TCTCCGTCCACCAGGGGCTCACCGTCGTCCACCGCCTCCACCCTGCATAG
    AGAGGCAGGTGGTCCCCGAGTGGCAGCAGGTGGCGGAGGTGGGACGTATC 660        670        680        690        700
    CGTGGCTCCTTTGCCTGGCATGACAACTTGTGGCTGTAAGGTCCCAGCCT
    GCACCGAGGAAACGGACCGTACTGTTGAACACCGACATTCCAGGGTCGGA 710        720        730        740        750
    CAAAAAGCCTGAGGATGGCAGGCCACCAACCCCAGCGCCCTGAAACCGGA
    GTTTTTCGGACTCCTACCGTCCGGTGGTTGGGGTCGCGGGACTTTGGCCT 760        770        780        790        800
    GCTCACAACTAGGAAGGTCTGGGGTCCCAGGATGCTCCTGCATTCCTCTG
    CGAGTGTTGATCCTTCCAGACCCCAGGGTCCTACGAGGACGTAAGGAGAC 810        820        830        840        850
    ACGGCCTTTCACACGCCTCTTGGCCCTGGTCGTGACCCCAGGCTGGGGCA
    TGCCGGAAAGTGTGCGGAGAACCGGGACCAGCACTGGGGTCCGACCCCGT 860        870        880        890        900
    GATGCCAAGGGATGGGACATAATAGCACAACAAGTGGTGTGTAAATGCGG
    CTACGGTTCCCTACCCTGTATTATCGTGTTGTTCACCACACATTTACGCC 910        920        930        940        950
    CTCAGGTTTCAGTAATCCTGTGGGACCCACTAGCTCTTTGGGGGCGGGGA
    GAGTCCAAAGTCATTAGGACACCCTGGGTGATCGAGAAACCCCCGCCCCT 960        970        980        990       1000
    GTGAGGGGGATGGTAGGGAAGCGGGGGCTGGTGTGTGTCCGGTGGCCTGA
    CACTCCCCCTACCATCCCTTCGCCCCCGACCACACACAGGCCACCGGACT 1010       1020       1030       1040       1050
    GGCTGAAGAAAGGGGTGGCAGACAGCATGGGACAGGGTGAACAGGCCCTG
    CCGACTTCTTTCCCCACCGTCTGTCGTACCCTGTCCCACTTGTCCGGGAC 1060       1070       1080       1090       1100
    GGGAAATCAGCCGAATAGGCGGATCCCTAGGCCGTGAGCCACGGATAGGC
    CCCTTTAGTCGGCTTATCCGCCTAGGGATCCGGCACTCGGTGCCTATCCG
                                BamHI
           1110       1120       1130       1140       1150
    TGCTGGCCCAAATCAGTCCAATGGCTGAGAGAGTGGTGGGTGGCACCCT
    ACGACCGGGTTTAGATCAGGTTACCGACTCTCTCACCACCCACCGTGGGA 1160       1170       1180       1190       1200
    TCTGGACACGCCCCTCAAACGTAGGAAGTCTTCCACAGTTCCTGGGCTAC
    AGACCTGTGCGGGGAGTTTGCATCCTTCAGAAGGTGTCAAGGACCCGATG
```

FIGURE 3c

```
        1210      1220      1230      1240      1250
AGCGCACCCACATGGCATATACCGCTCCAGGGAGTAATGGGTTTTGCATC
TCGCGTGGGTGTACCGTATATGGCGAGGTCCCTCATTACCCAAAACGTAG 1260      1270      1280      1290      1300
TGCTGATACTCCAGGCGCTGTCATTGTCCGGACTCTGGAAATCCCAACGA
ACGACTATGAGGTCCGCGACAGTAACAGGCCTGAGACCTTTAGGGTTGCT 1310      1320      1330      1340      1350
CGGGTTCCTGCTTCACAGTCTGAACAGCTTACTCCTGAGTCCCTCAGGAC
GCCCAAGGACGAAGTGTCAGACTTGTCGAATGAGGACTCAGGGAGTCCTG 1360      1370      1380      1390      1400
CCTCAATAACTGAGAAATTTCCCTGAGGATTCAAAGGATAAACAGGGACT
GGAGTTATTGACTCTTTAAAGGGACTCCTAAGTTTCCTATTTGTCCCTGA 1410      1420      1430      1440      1450
CCACGTGCCTGGATACTTTTTCTCCATGGGACACAGAACCTGTTGTCCAG
GGTGCACGGACCTATGAAAAGAGGTACCCTGTGTCTTGGACAACAGGTC 1460      1470      1480      1490      1500
ATGCTAGGGGAGAAGGGAAAATCCACACTGTTGGCTACAGTTGATCTCCA
TACGATCCCCTCTTCCCTTTTAGGTGTGACAACCGATGTCAACTAGAGGT 1510      1520      1530      1540      1550
CTGTTCAGGGACACCAGAGCCTTAGGGTACAGAGCTGGCTCTGTGTCTCT
GACAAGTCCCTGTGGTCTCGGAATCCCATGTCTCGACCGAGACACAGAGA 1560      1570      1580      1590      1600
TCATCTCTGCTTCTGGCATAGCACTGTTTTGGGCAACCCTTCCATGTGTG
AGTAGAGACGAAGACCGTATCGTGACAAAACCCGTTGGGAAGGTACACAC 1610      1620      1630      1640      1650
TACCAAGGGCTGGTGTCTGTTTGTCTCCATCTCTCTAAGTGGTGCTCTTG
ATGGTTCCCGACCACAGACAAACAGAGGTAGAGAGATTCACCACGAGAAC 1660      1670      1680      1690      1700
CTGTCTGTCACTCTCTGCACACCAGTGCTCATACGAGAAGTTTATATGAG
GACAGACAGTGAGAGACGTGTGGTCACGAGTATGCTCTTCAAATATACTC 1710      1720      1730      1740      1750
AAGGCAAGCCCTGCTCCTCCTTAGTGAGTTGCACCCATGGGAGATCAGAC
TTCCGTTCGGGACGAGGAGGAATCACTCAACGTGGGTACCCTCTAGTCTG 1760      1770      1780      1790      1800
TTTGTTAGTCCACACATTCGGAGAGTGCTTTCTCAAACTTGAAAGTCCAC
AAACAATCAGGTGTGTAAGCCTCTCACGAAAGAGTTTGAACTTTCAGGTG
```

FIGURE 3d

```
          1810      1820      1830      1840      1850
     AGTGTGCGGTCACTGCTGAACTGCAGAAGGTGCGGTGTGACCCTCCCTCC
     TCACACGCCAGTGACGACTTGACGTCTTCCACGCCACACTGGGAGGGAGG 1860      1870      1880      1890      1900
     GTCGCTGGACAGACGTGAATAGTGCAAAGGCCTCAGGTAGCTTGGCCACA
     CAGCGACCTGTCTGCACTTATCACGTTTCCGGAGTCCATCGAACCGGTGT 1910      1920      1930      1940      1950
     CTTTGCACAGATGGAGAAATGGGGCATGGCCTGGGGCCTGAGGGCACTCC
     GAAACGTGTCTACCTCTTTACCCCGTACCGGACCCCGGACTCCCGTGAGG 1960      1970      1980      1990      2000
     CTGAACATTATTTGATACCTGCCAGGGAGATGGTAAGGACAGCTCCCCAT
     GACTTGTAATAAACTATGGACGGTCCCTCTACCATTCCTGTCGAGGGGTA 2010      2020      2030      2040      2050
     TAAGTTCCATGACACACTGGTGCCAGAAACATGCATGGCTGCCAGTTTAC
     ATTCAAGGTACTGTGTGACCACGGTCTTTGTACGTACCGACGGTCAAATG 2060      2070      2080      2090      2100
     CCTATCGAGGCCCTTTCAAAGCGGTTCTGTTCTCCATGTGAGGACACATT
     GGATAGCTCCGGGAAAGTTTCGCCAAGACAAGAGGTACACTCCTGTGTAA 2110      2120      2130      2140      2150
     CAAGCCTGCCCGGTCACCCAAGCCTGTGGGGCTGGGAGCAGCAAGAGGAT
     GTTCGGACGGGCCAGTGGGTTCGGACACCCCGACCCTCGTCGTTCTCCTA 2160      2170      2180      2190      2200
     CAAGATAAGCCATCCAGCCTATAGTCCTGAGAGCCAATATATGTGTTCTG
     GTTCTATTCGGTAGGTCGGATATCAGGACTCTCGGTTATATACACAAGAC 2210      2220      2230      2240      2250
     CAAAGAGTACAAAGAGTGATGATTCAGACTGGAAGACTGCAGGTAGCAGG
     GTTTCTCATGTTTCTCACTACTAAGTCTGACCTTCTGACGTCCATCGTCC 2260      2270      2280      2290      2300
     TGCTTATGCTGAAGTTCTGGTCCATCACTGAAACCACACAAAATAGGCAA
     ACGAATACGACTTCAAGACCAGGTAGTGACTTTGGTGTGTTTTATCCGTT 2310      2320      2330      2340      2350
     GGGTTGCTCATGCTCATGGTAAGGTCAGGGAAAGTATGCCTGGCACTTGG
     CCCAACGAGTACGAGTACCATTCCAGTCCCTTTCATACGGACCGTGAACC 2360      2370      2380      2390      2400
     GAAGGATGGAAAGGCCCTTGTATCAGGGTGTTCAAAGGGCTGTGGGGTCA
     CTTCCTACCTTTCCGGGAACATAGTCCCACAAGTTTCCCGACACCCCAGT
```

FIGURE 3e

```
          2410      2420      2430      2440      2450
      CCCACCGTGGCTTCTGTGTCTGGGATTGCAACCTGTTCTGTGTCTCAGAT
      GGGTGGCACCGAAGACACAGACCCTAACGTTGGACAAGACACAGAGTCTA 2460      2470      2480      2490      2500
      CTTCTGCACTCTCACTGGTCACCCCCAGGCACTTTATTCCTGCCTCTCCT
      GAAGACGTGAGAGTGACCAGTGGGGGTCCGTGAAATAAGGACGGAGAGGA 2510      2520      2530      2540      2550
      TTCTGCCAGGAATCCTTGCTGGACCACTGTGATTCCACTCAGAACTTGCT
      AAGACGGTCCTTAGGAACGACCTGGTGACACTAAGGTGAGTCTTGAACGA 2560      2570      2580      2590      2600
      CACTCAGTGAGATAACGGGGATCAGTAAGTATGTCTACATATGTTCTGTG
      GTGAGTCACTCTATTGCCCCTAGTCATTCATACAGATGTATACAAGACAC 2610      2620      2630      2640      2650
      GGTTTGTGTATGTGTGTGTGCGCGCACACACACGTGTGTGTGACTCCCAC
      CCAAACACATACACACACGCGCGTGTGTGTGCACACACACTGAGGGTG 2660      2670      2680      2690      2700
      ATCTCAGTTATTTTCGGAATCATTCACCTTTACAACAATAACTGTCAGCT
      TAGAGTCAATAAAAGCCTTAGTAAGTGGAAATGTTGTTATTGACAGTCGA 2710      2720      2730      2740      2750
      AAGGTGGCTCTGATGTACTGTCTCTGGTCATTTCTGACTTAGAGGCTAAT
      TTCCACCGAGACTACATGACAGAGACCAGTAAAGACTGAATCTCCGATTA 2760      2770      2780      2790      2800
      CCTCCTCAGATGCAGGCCTGAAGGAGACACACAGAGTCATGGCTGCGACC
      GGAGGAGTCTACGTCCGGACTTCCTCTGTGTGTCTCAGTACCGACGCTGG 2810      2820      2830      2840      2850
      CTTACAGGTGTGGCCCTGCCCGGACTCTACTCAGCTGTGCCTTTGGAGCC
      GAATGTCCACACCGGGACGGGCCTGAGATGAGTCGACACGGAAACCTCGG 2860      2870      2880      2890      2900
      TGCCAATTGCCCAGTACCACACTTCCTTCAGGGTCCACCATTCTGCCCCC
      ACGGTTAACGGGTCATGGTGTGAAGGAAGTCCCAGGTGGTAAGACGGGGG 2910      2920      2930      2940      2950
      TCGCCTCCACCCCTCCTCCTGCTCCTGCCTCTGCACCTCCGCCTCCTCCT
      AGCGGAGGTGGGGAGGAGGACGAGGACGGAGACGTGGAGGCGGAGGAGGA 2960      2970      2980      2990      3000
      GAGCACTGGACCACAACGAGTAGCAGAAAGGATACCACGTTGGCCCAGAA
      CTCGTGACCTGGTGTTGCTCATCGTCTTTCCTATGGTGCAACCGGGTCTT
```

FIGURE 3f

```
       3010       3020       3030       3040       3050
GCCAGGGATGCCCTGGATGTTGGCACTCTTCTGAGCCAAGCCACGCTTCC
CGGTCCCTACGGGACCTACAACCGTGAGAAGACTCGGTTCGGTGCGAAGG 3060       3070       3080       3090       3100
TCCTCTCATGACTCTTGCACATAAACCAAACGTAGGCCCTGCAGGTTTTC
AGGAGAGTACTGAGAACGTGTATTTGGTTTGCATCCGGGACGTCCAAAAG 3110       3120       3130       3140       3150
TCAGGCTTAGAGCTAAGTTCCACTTACAAGGTCGCCAGTGCCAGCATCTC
AGTCCGAATCTCGATTCAAGGTGAATGTTCCAGCGGTCACGGTCGTAGAG 3160       3170       3180       3190       3200
ATCTAGTGCCGGGAGCTCACTCGGGACTCCAGGCCTTTCCTGGCACTGCT
TAGATCACGGCCCTCGAGTGAGCCCTGAGGTCCGGAAAGGACCGTGACGA 3210       3220       3230       3240       3250
CCTCCAATGTCTTCTCCTCCAGCTCCAGGGAGGACCCCTGTTTCTGTTAT
GGAGGTTACAGAAGAGGAGGTCGAGGTCCCTCCTGGGGACAAAGACAATA 3260       3270       3280       3290       3300
TCATCTGGCACAACCTCCACATCCTCAGTGATGTCCTCTGCAAGCAGCTG
AGTAGACCGTGTTGGAGGTGTAGGAGTCACTACAGGAGACGTTCGTCGAC 3310       3320       3330       3340       3350
GAAACCCCGTCTGATCCCTGCCACGACTCCGTCCACCTGGGCCTCGCTGT
CTTTGGGGCAGACTAGGGACGGTGCTGAGGCAGGTGGACCCGGAGCGACA 3360       3370       3380       3390       3400
CCTCTCCTGCCTCCACTCTGAAGAGGGTGGCATCTTCGCCTGGTGTGGCC
GGAGAGGACGGAGGTGAGACTTCTCCCACCGTAGAAGCGGACCACACCGG 3410       3420       3430       3440       3450
ACTGGTGGCTCCAACGTCCCAGCCATGCACAGCATCACCAGGACAGGCTG
TGACCACCGAGGTTGCAGGGTCGGTACGTGTCGTAGTGGTCCTGTCCGAC 3460       3470       3480       3490       3500
TTGCTGGCCAGATGCTAGGGGAGTAGGGAAAAACCCCACCGTTTGCCACG
AACGACCGGTCTACGATCCCCTCATCCCTTTTTGGGGTGGCAAACGGTGC 3510       3520       3530       3540       3550
TTGATCTCCATTGTTCAGGGACACCAAATGGGAAAGGGGACGGAATGAAT
AACTAGAGGTAACAAGTCCCTGTGGTTTACCCTTTCCCCTGCCTTACTTA 3560       3570       3580       3590       3600
AAAATTCCCCTTTTGATCACTCAACAGGAGGTCCTAGTCACCAGGTCTCA
TTTTAAGGGGAAAACTAGTGAGTTGTCCTCCAGGATCAGTGGTCCAGAGT
```

FIGURE 3g

```
       3610      3620      3630      3640      3650
TACATGTTCCTGAAAAAGAAAGCTTGTACTTCAGCATATAGACAAGTTTC
ATGTACAAGGACTTTTTCTTTCGAACATGAAGTCGTATATCTGTTCAAAG
                     HindIII
       3660      3670      3680      3690      3700
CTCTCAGCGATGTTACTGTGTACACGCATATATTTGTGTACATGTGGACG
GAGAGTCGCTACAATGACACATGTGCGTATATAAACACATGTACACCTGC 3710      3720      3730      3740      3750
TAGAAATTTTAGTGCTTACCAAAATTCAAGGTCCTGGGAAAGAAAGCTTG
ATCTTTAAAATCACGAATGGTTTTAAGTTCCAGGACCCTTTCTTTCGAAC
                                              HindIII
       3760      3770      3780      3790      3800
TACTTCTGCATATGGACAGGTTTCCTCTCAGCGATGTAACTGTATTCACC
ATGAAGACGTATACCTGTCCAAAGGAGAGTCGCTACATTGACATAAGTGG 3810      3820      3830      3840      3850
CATCTATTTGTGCACATGTGTGTGTAGAAATTTGAGTGCTTACCAAAATT
GTAGATAAACACGTGTACACACATCTTTAAACTCACGAATGGTTTTAA 3860      3870      3880      3890      3900
CATGTTCCTTGAAAAGAAAGCTTGTACTTCCGCATATGGAGAAGCTTCCT
GTACAAGGAACTTTTCTTTCGAACATGAAGGCGTATACCTCTTCGAAGGA
                HindIII                      HindIII
       3910      3920      3930      3940      3950
CTCAGGGATGTTACTGTGTACACGAGTGTGTTCTGCACATATGCGTGCA
GAGTCCCTACAATGACACATGTGCTCACACAAAGACGTGTATACGCACGT 3960      3970      3980      3990      4000
GAAATTTTAGTGCTTACCAAAACTCAAGTTCCTGGAAAAGAAAGCTTGTA
CTTTAAAATCACGAATGGTTTTGAGTTCAAGGACCTTTTCTTTCGAACAT
                                              HindIII
       4010      4020      4030      4040      4050
CTTTTGCATATGGACAGGTTTCCCCTCAGCGATCTTACTGTGTACACGCA
GAAAACGTATACCTGTCCAAAGGGGAGTCGCTAGAATGACACATGTGCGT 4060      4070      4080      4090      4100
TCTATTTGTGCACATGTGCACATAGAAATTTGAGTGCTTACCACAATTAA
AGATAAACACGTGTACACGTGTATCTTTAAACTCACGAATGGTGTTAATT 4110      4120      4130      4140      4150
TGTTCCTGGAAAAGAAAGCTTGCACTTCTGCATATGGACAAGTTTTCTCT
ACAAGGACCTTTTCTTTCGAACGTGAAGACGTATACCTGTTCAAAAGAGA
                     HindIII
       4160      4170      4180      4190      4200
CAGGGATGTTACTGAGTACACGTGCATGTTTGTACACATGTGCGTGCAGA
GTCCCTACAATGACTCATGTGCACGTACAAACATGTGTACACGCACGTCT
```

FIGURE 3h

```
          4210      4220      4230      4240      4250
AATTTGAGTGCCTACCAAAATTCAAGTTCCTGGAAAAGAAAGCTGTACTT
TTAAACTCACGGATGGTTTTAAGTTCAAGGACCTTTTCTTTCGACATGAA 4260      4270      4280      4290      4300
CTGCATATGGACAGGTTTCCCCTCAGCGATGTTACCGTGTACACATGTAT
GACGTATACCTGTCCAAAGGGGAGTCGCTACAATGGCACATGTGTACATA 4310      4320      4330      4340      4350
GTTTCTGTACATGTGCGTGTAGAAATCCCTGCCAGTTCGCTTGTGTGTAT
CAAAGACATGTACACGCACATCTTTAGGGACGGTCAAGCGAACACACATA 4360      4370      4380      4390      4400
GAGCTACTGCAACTGACCTAGCCAGGTGATAGAAGTTGGACAGCGAAACC
CTCGATGACGTTGACTGGATCGGTCCACTATCTTCAACCTGTCGCTTTGG 4410      4420      4430      4440      4450
ATGAAGTTCTTAGGGAACGGTACAGAGTCTCTGGCCAGCAGAAGCACTGA
TACTTCAAGAATCCCTTGCCATGTCTCAGAGACCGGTCGTCTTCGTGACT 4460      4470      4480      4490      4500
AGCCAGGGAATCGCTTCCCGTTTGCTCACTGAGCAAACACGTTCTAGGCG
TCGGTCCCTTAGCGAAGGGCAAACGAGTGACTCGTTTGTGCAAGATCCGC 4510      4520      4530      4540      4550
GAATCACAGTCGTGCACCTAGGATGCTTGGCAGAAAGGAGAGGCCGGAGG
CTTAGTGTCAGCACGTGGATCCTACGAACCGTCTTTCCTCTCCGGCCTCC 4560      4570      4580      4590      4600
AGAGAGCCTGGGGAGTGTGAAGATGAAAGTCCACTACATCTGCAGTTTAC
TCTCTCGGACCCCTCACACTTCTACTTTCAGGTGATGTAGACGTCAAATG 4610      4620      4630      4640      4650
GAAAAGTAGAAAATGTACCTAATGAGCTGGGAGGACAACTGTACTTAATT
CTTTTCATCTTTTACATGGATTACTCGACCCTCCTGTTGACATGAATTAA 4660      4670      4680      4690      4700
AATTGAGTTATCTAAGAGGATTTCCATCCAAACAGCCAAAAGTGCTTCTG
TTAACTCAATAGATTCTCCTAAAGGTAGGTTTGTCGGTTTTCACGAAGAC 4710      4720      4730      4740      4750
GTTTCTTCTTGCTGCCTGTAGTAAAACATGAAGGGATATATATATATATA
CAAAGAAGAACGACGGACATCATTTGTACTTCCCTATATATATATATAT 4760      4770      4780      4790      4800
TATATATATATTTAATGTTTAACATAAAGATTATTAAAACAGGGGACAAC
ATATATATATAAATTACAAATTGTATTTCTAATAATTTTGTCCCCTGTTG
```

FIGURE 3i

```
         4810       4820       4830       4840       4850
ATTTGCTGATTTGGGAATTTTCCAGTCTTTTAAGATGATGGAAGATGATA
TAAACGACTAAACCCTTAAAAGGTCAGAAAATTCTACTACCTTCTACTAT 4860       4870       4880       4890       4900
AATTAATGACTCTCAAGCAAGATCATATCCAGGGCATTGAGATTAGGTGG
TTAATTACTGAGAGTTCGTTCTAGTATAGGTCCCGTAACTCTAATCCACC 4910       4920       4930       4940       4950
TCTAAATATAACATTTTACACCACCGATAGGCCAGTTCTTCTTCATATTA
AGATTTATATTGTAAAATGTGGTGGCTATCCGGTCAAGAAGAAGTATAAT 4960       4970       4980       4990       5000
TTTTTTCTAAACAAAGGTGTTCTAAAGATGAGTATGACTGTAAAATTCTT
AAAAAAGATTTGTTTCCACAAGATTTCTACTCATACTGACATTTTAAGAA 5010       5020       5030       5040       5050
TGTTAAGCCTCAGAAAGCTGGAAGGGGATGCTTCATGGCATTATTTTAGT
ACAATTCGGAGTCTTTCGACCTTCCCCTACGAAGTACCGTAATAAAATCA 5060       5070       5080       5090       5100
CAGGCCAATACCCTCCAAAGAGTTTAGGGGTGTCACTCAGAGATCCTTTC
GTCCGGTTATGGGAGGTTTCTCAAATCCCCACAGTGAGTCTCTAGGAAAG 5110       5120       5130       5140       5150
AGTCACACAATAAGACTTCTACCAAGGTTCAGGGTGTTATCCCTCAGCTA
TCAGTGTGTTATTCTGAAGATGGTTCCAAGTCCCACAATAGGGAGTCGAT 5160       5170       5180       5190       5200
TCTCAGCAGAAAACCAAGACAGAGTAAGCCTTATTATGAAGACATGTGTG
AGAGTCGTCTTTTGGTTCTGTCTCATTCGGAATAATACTTCTGTACACAC 5210       5220       5230       5240       5250
ATTGTCGCTTTTGAGTGGGGTGCTTTGCCTTGAACACCAGTAAGAGTAAC
TAACAGCGAAAACTCACCCCACGAAACGGAACTTGTGGTCATTCTCATTG 5260       5270       5280       5290       5300
AGGAGACACACCAAGGTTTTAAGATAACATATTTAAGTTCAGCTCGGTCT
TCCTCTGTGTGGTTCCAAAATTCTATTGTATAAATTCAAGTCGAGCCAGA 5310       5320       5330       5340       5350
GAAAGGACCAGCAATAGTACAAAATAGGAGCTCTGGACTTCTACCTTCTA
CTTTCCTGGTCGTTATCATGTTTTATCCTCGAGACCTGAAGATGGAAGAT 5360       5370       5380       5390       5400
CAAGCAGGAAGCAGGCTAGGGACACTGTTTCATGTAACCATATCTAGCCA
GTTCGTCCTTCGTCCGATCCCTGTGACAAAGTACATTGGTATAGATCGGT
```

FIGURE 3j

```
         5410      5420      5430      5440      5450
    CCTTTCATGCAATGGCATCATGTCAGCGGGTAGAAAGAAAAAATCAGAGA
    GGAAAGTACGTTACCGTAGTACAGTCGCCCATCTTTCTTTTTAGTCTCT 5460      5470      5480      5490      5500
    CTGAAGCCTAGGAAGTGTCCAGGCCTTAAATACTAATCAAAGGACTGCCC
    GACTTCGGATCCTTCACAGGTCCGGAATTTATGATTAGTTTCCTGACGGG 5510      5520      5530      5540      5550
    GCAAGAACCCATGGGATTTCAGAACTGCTACTATTGACTCCCTTTTCCCT
    CGTTCTTGGGTACCCTAAAGTCTTGACGATGATAACTGAGGGAAAAGGGA 5560      5570      5580      5590      5600
    CCCCTTTCTGGAACAGGAGTGTCTATGAAGGTTATCTATGCCTGAACCAC
    GGGGAAAGACCTTGTCCTCACAGATACTTCCAATAGATACGGACTTGGTG 5610      5620      5630      5640      5650
    CACTGTATGTTGGCTGTGAAAGGGAGCAGATTAACTCATCTCTTTTGTTC
    GTGACATACAACCGACACTTTCCCTCGTCTAATTGAGTAGAGAAAACAAG 5660      5670      5680      5690      5700
    ACACATCCTCAGGTCTAGAGGAACTACACTTCTATAATTTGAACTGATGT
    TGTGTAGGAGTCCAGATCTCCTTGATGTGAAGATATTAAACTTGACTACA 5710      5720      5730      5740      5750
    GTTGCAGACTTGAGAGGCTCTTGGACTGCAAGGAGATCAAACCAGTCAAT
    CAACGTCTGAACTCTCCGAGAACCTGACGTTCCTCTAGTTTGGTCAGTTA 5760      5770      5780      5790      5800
    CCTAAAGTAAATCTCTCCTGCATATTCATTCGAAGGACTGATGCTGAAGC
    GGATTTCATTTAGAGAGGACGTATAAGTAAGCTTCCTGACTACGACTTCG 5810      5820      5830      5840      5850
    TGAAGCTCCAATACTTGGGCTATGTGATGGGAATAACCGTCTCATTGGAA
    ACTTCGAGGTTATGAACCCGATACACTACCCTTATTGGCAGAGTAACCTT 5860      5870      5880      5890      5900
    AAGACCGTGATGCGGAAAAAGATGAAGGTAGGAGAAGGGGACAGCAGAGG
    TTCTGGCACTACGCCTTTTTCTACTTCCATCCTCTTCCCCTGTCGTCTCC 5910      5920      5930      5940      5950
    ATGGGATTGTTGGATAGCATCATCGACTCAATGGACTTGAGTTTGAGCAA
    TACCCTAACAACCTATCGTAGTAGCTGAGTTACCTGAACTCAAACTCGTT 5960      5970      5980      5990      6000
    GCTCCTGGAGTTGATGGACAGGGAAGCCTGCAGCGCTGCAGCCCATGGGT
    CGAGGACCTCAACTACCTGTCCCTTCGGACGTCGCGACGTCGGGTACCCA
```

FIGURE 3k

```
          6010       6020       6030       6040       6050
      CGCCAAGAATACGACACAACTGAGCAACAGAACACGAGATACTGTACACG
      GCGGTTCTTATGCTGTGTTGACTCGTTGTCTTGTGCTCTATGACATGTGC 6060       6070       6080       6090       6100
      TGGACCCTGATCCATAGCTGGACCTGACTTAGATGACAAGGTCCTGAACT
      ACCTGGGACTAGGTATCGACCTGGACTGAATCTACTGTTCCAGGACTTGA 6110       6120       6130       6140       6150
      TCAAGTTAATGCTGTAACAGATAAATTGTTTAAAAGCATTGGCAGGAAAA
      AGTTCAATTACGACATTGTCTATTTAACAAATTTTCGTAACCGTCCTTTT 6160       6170       6180       6190       6200
      GGCATTTTGGACATACACGTATGTGAACAATTTCTGGCCATGTGTGTACC
      CCGTAAAACCTGTATGTGCATACACTTGTTAAAGACCGGTACACACATGG 6210       6220       6230       6240       6250
      ACGTGGTTTTAAATTATGTCCACGGTTCCTTCTTCCGCCCCTTCACATGT
      TGCACCAAAATTTAATACAGGTGCCAAGGAAGAAGGCGGGGAAGTGTACA 6260       6270       6280       6290       6300
      GTGGTGGGCTTAGTGGCTCACTTCTCATGTTAGAATACTGTAGAAACGAA
      CACCACCCGAATCACCGAGTGAAGAGTACAATCTTATGACATCTTTGCTT 6310       6320       6330       6340       6350
      CAATGAAGTGTCTGAGACTAGGTCATAAAAGGCACTGCAGCCTTCTTGAT
      GTTACTTCACAGACTCTGATCCAGTATTTTCCGTGACGTCGGAAGAACTA 6360       6370       6380       6390       6400
      CATCCTCTTGGATCACTCACTCTAGAAGCCAGCTTAGTCATATCTCGAGA
      GTAGGAGAACCTAGTGAGTGAGATCTTCGGTCGAATCAGTATAGAGCTCT 6410       6420       6430       6440       6450
      ACACTCAGGTAGCCCTTTAGAGAGGCCCATGTGAAAGAACCGAGGCTTTC
      TGTGAGTCCATCGGGAAATCTCTCCGGGTACACTTTCTTGGCTCCGAAAG 6460       6470       6480       6490       6500
      TCCCAACAGCCAGCAAGCAAACTGGTTCCAACAGCTATGTGAGTAAGCCA
      AGGGTTGTCGGTCGTTCGTTTGACCAAGGTTGTCGATACACTCATTCGGT 6510       6520       6530       6540       6550
      TCTTGGAAGGAAATCCACCAGCGCATGTCAAGGCTTCAGAGGATGGCAAT
      AGAACCTTCCTTTAGGTGGTCGCGTACAGTTCCGAAGTCTCCTACCGTTA 6560       6570       6580       6590       6600
      CTCATGAGACACTGAGCCACAACACTCAGCTGAATTACTCCTGGATTCCC
      GAGTACTCTGTGACTCGGTGTTGTGAGTCGACTTAATGAGGACCTAAGGG
```

FIGURE 3I

```
        6610       6620       6630       6640       6650
AACTTTCAGCAGCAGTATGAAATAATATTGTTTTAAGCTGCTAGTTTTGG
TTGAAAGTCGTCGTCATACTTTATTATAACAAAATTCGACGATCAAAACC 6660       6670       6680       6690       6700
CTAACTGCTTATGCAGCACTAGTTCATTAATGCACTGCCAACTTTGGGCA
GATTGACGAATACGTCGTGATCAAGTAATTACGTGACGGTTGAAACCCGT 6710       6720       6730       6740       6750
ATGTCTTTATTCAGGGCTGCCTGTCCATCTAGTCCAATTTAATCCAGAAT
TACAGAAATAAGTCCCGACGGACAGGTAGATCAGGTTAAATTAGGTCTTA 6760       6770       6780       6790       6800
CTGCTACTTCAGTTCAGAAAACATAGCCCACCCTTGATCTGACCACCCTC
GACGATGAAGTCAAGTCTTTTGTATCGGGTGGGAACTAGACTGGTGGGAG 6810       6820       6830       6840       6850
AGTATCCGATCAAATATCATTTCACTACCCGGAATATCTTATCAGCCTTG
TCATAGGCTAGTTTATAGTAAAGTGATGGGCCTTATAGAATAGTCGGAAC 6860       6870       6880       6890       6900
CCTAGCCTCAGCAATGATCCTCTCAGTTGAGCCAGAGTCCACCCTCACGC
GGATCGGAGTCGTTACTAGGAGAGTCAACTCGGTCTCAGGTGGGAGTGCG 6910       6920       6930       6940       6950
TTATAGTCCTCATTTTAATAAGTTTCCATCCACTGACACCCATTCTGTTA
AATATCAGGAGTAAAATTATTCAAAGGTAGGTGACTGTGGGTAAGACAAT 6960       6970       6980       6990       7000
TTGTTGTCCATTGCTTTTCAGTCTCCCATCTCTGTCTGCAATCCCATGGG
AACAACAGGTAACGAAAGTCAGAGGGTAGAGACAGACGTTAGGGTACCC 7010       7020       7030       7040       7050
CCCACCCTGTTCCTCAGCTATAAATCCCAGCTGCACCCCTCCTGGAGTCA
GGGTGGGACAAGGAGTCGATATTTAGGGTCGACGTGGGGAGGACCTCAGT 7060       7070       7080       7090       7100
CACATAAGCTCAATCTCTCTCCCATGTTATAATACGCCACTGTAGTACTC
GTGTATTCGAGTTAGAGAGAGGGTACAATATTATGCGGTGACATCATGAG 7110       7120       7130       7140       7150
TTACCTTGAATAAAGTTTTTCTTGCCACCTTTCGTAAGTGTTATGAAAAC
AATGGAACTTATTTCAAAAGAACGGTGGAAAGCATTCACAATACTTTTG 7160       7170       7180       7190       7200
TTTTTGAACATTCCCAAGTTCTGTTAGTAAGGATTACTCTCAAAGGAATC
AAAAACTTGTAAGGGTTCAAGACAATCATTCCTAATGAGAGTTTCCTTAG
```

FIGURE 3m

```
         7210      7220      7230      7240      7250
TAGTTTTATATCTTTATTCTTTATACTATATTCATTTGGGGGAACAAATT
ATCAAAATATAGAAATAAGAAATATGATATAAGTAAACCCCCTTGTTTAA 7260      7270      7280      7290      7300
TCTAGAATTAAAACATTTCATGTTTTTACCATACAAACAGAAAATATCTT
AGATCTTAATTTTGTAAAGTACAAAAATGGTATGTTTGTCTTTTATAGAA 7310      7320      7330      7340      7350
TGAAAATACATTTACATATCTTAAAATATGTAGTAATCTGAAAAGGATGT
ACTTTTATGTAAATGTATAGAATTTTATACATCATTAGACTTTTCCTACA 7360      7370      7380      7390      7400
GTATATAGACATGTCACTGTATATACACACATACCCTCAGAGCTCCAAGG
CATATATCTGTACAGTGACATATATGTGTGTATGGGAGTCTCGAGGTTCC 7410      7420      7430      7440      7450
AAAACTTAATTCTCAGTAAACAATAAATGAATACATTCAGCCTGAAAATA
TTTTGAATTAAGAGTCATTTGTTATTTACTTATGTAAGTCGGACTTTTAT 7460      7470      7480      7490      7500
GTGAACTCTTTGGATTCAACTTGCCAAAAATCTTAGACAATGAAATTTTA
CACTTGAGAAACCTAAGTTGAACGGTTTTAGAATCTGTTACTTTAAAAT 7510      7520      7530      7540      7550
ATTAAAAAACATGGATACATAAAAATAATTGGGATTCAGACAAAATTGCT
TAATTTTTGTACCTATGTATTTTATTAACCCTAAGTCTGTTTTAACGA 7560      7570      7580      7590      7600
AAATAAAGATAGGTCAACCCCTAAACCATCTCTGGAAAAAAAAAAAAAAA
TTTATTTCTATCCAGTTGGGGATTTGGTAGAGACCTTTTTTTTTTTTTT 7610      7620      7630      7640      7650
AGAAATCCTCAGTATCATGTAATAACCTATCATGGAAAAGAACCTACAAA
TCTTTAGGAGTCATAGTACATTATTGGATAGTACCTTTTCTTGGATGTTT 7660      7670      7680      7690      7700
AGAATAGATACATATCTGCATAACTAAATCACTCTGATATACATCTGAAA
TCTTATCTATGTATAGACGTATTGATTTAGTGAGACTATATGTAGACTTT 7710      7720      7730      7740      7750
TACAACATTGTAAATCTAATATATTTACAGGAAAAAAAAAAATTGTGAAG
ATGTTGTAACATTTAGATTATATAAATGTCCTTTTTTTTTTAACACTTC 7760      7770      7780      7790      7800
AAACTTCTAAAATACAAAGTTATAAAGAAAAAAAATCCTAAAGAATGTAG
TTTGAAGATTTATGTTTCAATATTTCTTTTTTTAGGATTTCTTACATC
```

FIGURE 3n

```
        7810       7820       7830       7840       7850
GAAGTATCTATGAATGTAAACAAAAATAGAAAACAAAAATAAAGCTTGTT
CTTCATAGATACTTACATTTGTTTTATCTTTTGTTTTATTTCGAACAA
                                         HindIII
        7860       7870       7880       7890       7900
GGGTTAAGACGACAAGAGCTGCTTCTTGGAAAAAGAAAATCAGAACACTT
CCCAATTCTGCTGTTCTCGACGAAGAACCTTTTTCTTTAGTCTTGTGAA 7910       7920       7930       7940       7950
GATACAACTGTGGCAAATCTATAAAGGGGACAGGGAGGTTAATTCCAATA
CTATGTTGACACCGTTTAGATATTTCCCCTGTCCCTCCAATTAAGGTTAT 7960       7970       7980       7990       8000
CTAGAAATGAGGAACGAAATGGGATTCTGAGAGGATAACATTCAACTCTG
GATCTTTACTCCTTGCTTTACCCTAAGACTCTCCTATTGTAAGTTGAGAC 8010
AGTGGAATTC
TCACCTTAAG
    EcoRI
```

FIGURE 4a

```
         10          20         30         40         50
GAATTCCAACTTAATCTCCTATGAGTCCAAAGTCCATGCTTCGAAACGCT
CTTAAGGTTGAATTAGAGGATACTCAGGTTTCAGGTACGAAGCTTTGCGA
EcoRI
         60          70         80         90        100
GTAGAACAATGCTTTTGTAAAAATACTCTCCTTTACATTTGATTTCACGT
CATCTTGTTACGAAAACATTTTATGAGAGGAAATGTAAACTAAAGTGCA 110         120        130        140        150
AATGATCAGTGTGGTGTTTTGTTTTTTTTCCCCCTCTTTATTTTTTTAA
TTACTAGTCACACCACAAAACAAAAAAAAGGGGGAGAAATAAAAAAATT 160         170        180        190        200
GTAGAAGAGGTTAAAGTGACATGTGACAAAGCTATGATTCTAGAGCCATG
CATCTTCTCCAATTTCACTGTACACTGTTTCGATACTAAGATCTCGGTAC 210         220        230        240        250
TAGACTTGTAGTCGTAGTTTTTTCAGCTGTCATTGAGTCTGGTTGACGCT
ATCTGAACATCAGCATCAAAAAGTCGACAGTAACTCAGACCAACTGCGA 260         270        280        290        300
CAGTGTCTTTGTCTGTAAGATAAGGGTGTGTATAGTACTCTAGAGTTTTG
GTCACAGAAACAGACATTCTATTCCCACACATATCATGAGATCTCAAAAC 310         320        330        340        350
GAGATACTCAAATAGCCCATTTTTCTGTACTTAACTAATCTGTAGTATGT
CTCTATGAGTTTATCGGGTAAAAGACATGAATTGATTAGACATCATACA 360         370        380        390        400
TTATACTTAGGTGGCAGTTTGTATAAAGGAAGCACTGGGACTTGTGACCG
AATATGAATCCACCGTCAAACATATTTCCTTCGTGACCCTGAACACTGGC 410         420        430        440        450
CACCCTCTAAGAATAAGAAAGTATTAAAAATATGGAACTCCCACGTATGT
GTGGGAGATTCTTATTCTTTCATAATTTTTATACCTTGAGGGTGCATACA 460         470        480        490        500
TACGTGAAGAAGAACAAGAGCCAGAAGTACGGAAAAGGGAGGGAGAGACC
ATGCACTTCTTCTTGTTCTCGGTCTTCATGCCTTTTCCCTCCCTCTCTGG 510         520        530        540        550
AAAGAAGTAGATGATGATGATGATGAAGTGATCTTGGTTGGAGTGGAACA
TTTCTTCATCTACTACTACTACTACTTCACTAGAACCAACCTCACCTTGT 560         570        580        590        600
TGGAAATGAAGATGCTGACGTGATCTTTGTTGGGATGAGCTCAGCTTCAA
ACCTTTACTTCTACGACTGCACTAGAAACAACCCTACTCGAGTCGAAGTT
```

FIGURE 4b

```
          610         620         630         640         650
     AACCAGTCGTTTCAAACATACTGAACAGAGATACCCCAGGTTCTTATTCA
     TTGGTCAGCAAAGTTTGTATGACTTGTCTCTATGGGGTCCAAGAATAAGT 660         670         680         690         700
     AGGAGAAAAGGTGTGGTCACTTCAGGAGAGGTAACGCTCACAGATTACA
     TCCTCTTTTTCCACACCAGTGAAGTCCTCTCCATTGCGAGTGTCTAATGT 710         720         730         740         750
     GCCTGTTAGTCATGTGACTCCTACATCAGAAGCAAAGACTGTCTTGCCAG
     CGGACAATCAGTACACTGAGGATGTAGTCTTCGTTTCTGACAGAACGGTC 760         770         780         790         800
     TGTCTGACTCTGACTCAAGATCAACAGGTAGTCCTATTATTATTGAATCT
     ACAGACTGAGACTGAGTTCTAGTTGTCCATCAGGATAATAATAACTTAGA 810         820         830         840         850
     CCGTCTCAAGCTGATTATAAAAATCTTTCACCACAAATAGTGCCTGATGG
     GGCAGAGTTCGACTAATATTTTTAGAAAGTGGTGTTTATCACGGACTACC 860         870         880         890         900
     CTTTTCGAAGGAGTTATGTTCTTCTTTGATTACCTTCACAAGGTCATTGC
     GAAAAGCTTCCTCAATACAAGAAGAAACTAATGGAAGTGTTCCAGTAACG 910         920         930         940         950
     AGCATCCAGTAGAAACAGCAGTTTCTGCAGGAGATATGAATAAAAGTCCT
     TCGTAGGTCATCTTTGTCGTCAAAGACGTCCTCTATACTTATTTTCAGGA 960         970         980         990        1000
     CATGTATCAAAGCGAGTTTCCCCTTGTGAAACAAATCGCAGAAATCCCAG
     GTACATAGTTTCGCTCAAAGGGGAACACTTTGTTTAGCGTCTTTAGGGTC 1010        1020        1030        1040        1050
     AAGGCCTAAACTCAGTGATGGCATTGTCGGGGAACATTCTTTAGGTTTCT
     TTCCGGATTTGAGTCACTACCGTAACAGCCCCTTGTAAGAAATCCAAAGA 1060        1070        1080        1090        1100
     CCCCGTCACGTTTTTTTCATACAGAGACCACTCAGCAAAGCACACCAGAC
     GGGGCAGTGCAAAAAAGTATGTCTCTGGTGAGTCGTTTCGTGTGGTCTG 1110        1120        1130        1140        1150
     CGTGTCCATACCTCACTAAGCCATGTTCAGAATGGAGAACCTTGTCCAAC
     GCACAGGTATGGAGTGATTCGGTACAAGTCTTACCTCTTGGAACAGGTTG 1160        1170        1180        1190        1200
     ACCTTTTCCAAAGGACAGTGTTCATTGCAAGCCTGTAAGACCTTTAGGGG
     TGGAAAAGGTTTCCTGTCACAAGTAACGTTCGGACATTCTGGAAATCCCC
```

FIGURE 4c

```
        1210      1220      1230      1240      1250
AAAGTGGACGGACAAAAACTGATTTTCCAAGTTTGGCAAGTCCAAACAAA
TTTCACCTGCCTGTTTTTGACTAAAAGGTTCAAACCGTTCAGGTTTGTTT 1260      1270      1280      1290      1300
ATTGGTGATCCCACAGAAGGAAATCTGATTGTGTTACTTCATGACTTCTA
TAACCACTAGGGTGTCTTCCTTTAGACTAACACAATGAAGTACTGAAGAT 1310      1320      1330      1340      1350
CTATGGCGAGCATGGAGGAGTTGGGCAGCCAGAAGCGAAGACCCACACCG
GATACCGCTCGTACCTCCTCAACCCGTCGGTCTTCGCTTCTGGGTGTGGC 1360      1370      1380      1390      1400
CGTTTAAATGCCTCAGCTGCTTGAAAGTTCTAAAAAATGTCAAGTTTATG
GCAAATTTACGGAGTCGACGAACTTTCAAGATTTTTTACAGTTCAAATAC 1410      1420      1430      1440      1450
AATCACATGAAGCACCATTTGGAACTTGAGAGGCAGAGAGGTGACAGCTG
TTAGTGTACTTCGTGGTAAACCTTGAACTCTCCGTCTCTCCACTGTCGAC 1460      1470      1480      1490      1500
GAAAACCCACACCACCTGCCAGCACTGCCTCCGCCAGTTTCCTACTCCCT
CTTTTGGGTGTGGTGGACGGTCGTGACGGAGGCGGTCAAAGGATGAGGGA 1510      1520      1530      1540      1550
TCCAGCTGCAGTGTCACATTGAAAGTGTCCACACGGCCCAGGAGCCCTCC
AGGTCGACGTCACAGTGTAACTTTCACAGGTGTGCCGGGTCCTCGGGAGG 1560      1570      1580      1590      1600
GCAGTCTGTCACATCTGTGAGTTGTCCTTTGAGACAGATCAGGTTCTCTT
CGTCAGACAGTGTAGACACTCAACAGGAAACTCTGTCTAGTCCAAGAGAA 1610      1620      1630      1640      1650
AGAGCACATGAAAGACAATCATAAGCCTGGTGAAATGCCCTATGTATGCC
TCTCGTGTACTTTCTGTTAGTATTCGGACCACTTTACGGGATACATACGG 1660      1670      1680      1690      1700
AGGTTTGCAGTTACAGATCATCATTTTTTGCAGATGTGGATGCACATTTC
TCCAAACGTCAATGTCTAGTAGTAAAAAACGTCTACACCTACGTGTAAAG 1710      1720      1730      1740      1750
AGAGCATACCATGGTAACACCAAGAATTTACTTTGCCCGTTTTGTCTCAA
TCTCGTATGGTACCATTGTGGTTCTTAAATGAAACGGGCAAAACAGAGTT 1760      1770      1780      1790      1800
AATTTTTCAAACTGCAACAGCATACAGACGTCATCATCGAGGGCACTGGG
TTAAAAAGTTTGACGTTGTCGTATGTCTGCAGTAGTAGCTCCCGTGACCC
```

FIGURE 4d

```
         1810      1820      1830      1840      1850
   AAAAGAGTTTTCACCAGTGTTCCAAATGTCGGCTACAGTTTTAACTACC
   TTTTCTCAAAAGTGGTCACAAGGTTTACAGCCGATGTCAAAAATTGATGG 1860      1870      1880      1890      1900
   AAAGAGGAGAGGGAGCACAAGACCCAGTGTCATCAAATGTTTAAGAAGCC
   TTTCTCCTCTCCCTCGTGTTCTGGGTCACAGTAGTTTACAAATTCTTCGG 1910      1920      1930      1940      1950
   TAAGCAGCTAGAAGGATTGTCTCCTGAAACAAAAATTTTTATTCAAGTAT
   ATTCGTCGATCTTCCTAACAGAGGACTTTGTTTTTAAAAATAAGTTCATA 1960      1970      1980      1990      2000
   CAATGGAACCCCTTCAGCCAGGATTGGTGGAAGTTGCATCCGTTACTGTG
   GTTACCTTGGGGAAGTCGGTCCTAACCACCTTCAACGTAGGCAATGACAC 2010      2020      2030      2040      2050
   AACACATCTGATTTTGAATCATCACCCCCCAAATCTAAAAGGAGGAGGTC
   TTGTGTAGACTAAAACTTAGTAGTGGGGGGTTTAGATTTTCCTCCTCCAG 2060      2070      2080      2090      2100
   AAAAAAAGAAAAATAATAGTTAATTCTGCCTTCAGTAAGTCTGAAGCAAG
   TTTTTTTCTTTTTATTATCAATTAAGACGGAAGTCATTCAGACTTCGTTC 2110      2120      2130      2140      2150
   TATTTCAGTCAAAGTTAAAAATCCCATTAAAAACCAAAAGATCAACTTAT
   ATAAAGTCAGTTTCAATTTTAGGGTAATTTTGGTTTTCTAGTTGAATA 2160      2170      2180      2190      2200
   AGCATTATTCAATAATATCAAATATAGGGAAACCGATGGGTAATTTATGT
   TCGTAATAAGTTATTATAGTTTATATCCCTTTGGCTACCCATTAAATACA 2210      2220      2230      2240      2250
   GATTTTGTTTTAAATAGAGGAAGTACAGTTTTGTTTGATCTTCATATTGA
   CTAAAACAAAATTTATCTCCTTCATGTCAAAACAAACTAGAAGTATAACT 2260      2270      2280      2290      2300
   GCTGCTATTTAAAAATCTATGATCTGTTTTTCGTGTAATTGTCTTAACAT
   CGACGATAAATTTTAGATACTAGACAAAAGCACATTAACAGAATTGTA 2310      2320      2330      2340      2350
   GTAAAAGGATGTGTGCATGTGTGTGTGAGAGAGAGAGAATGAGAGAAGT
   CATTTTCCTACACACGTACACACACACTCTCTCTCTTACTCTCTTCA 2360      2370      2380      2390      2400
   GGAGAAAGGAAAAGTAAGAACCTATTTTGGTATTTGATGTTACTTGTAAG
   CCTCTTTCCTTTTCATTCTTGGATAAAACCATAAACTACAATGAACATTC
```

FIGURE 4e

```
              2410      2420      2430      2440      2450
    TTCGAAAGCTCTCCTATACATATAATCTGTAGAGTGTTTTAGCAACGTAA
    AAGCTTTCGAGAGGATATGTATATTAGACATCTCACAAAATCGTTGCATT 2460      2470      2480      2490      2500
    TTTTGAAGTGTTTTCATGCCTTGCAGATCTCAGTATCAGCTATATAGCCA
    AAAACTTCACAAAAGTACGGAACGTCTAGAGTCATAGTCGATATATCGGT 2510      2520      2530      2540      2550
    GATTTGAATGTCACTTTCTGAAGTGCCTCTTGGGCTGATCTAAGATAACC
    CTAAACTTACAGTGAAAGACTTCACGGAGAACCCGACTAGATTCTATTGG 2560      2570      2580      2590      2600
    TGGCTCTGAAAGCGTGCAGTGGAGGTTGATGGAGAAGCTACGATGTGAGT
    ACCGAGACTTTCGCACGTCACCTCCAACTACCTCTTCGATGCTACACTCA 2610      2620      2630      2640      2650
    TTGGACCAGACACGGGTTTTAATCAGTGAAGAGCTGTGCCTTCGTGTCCC
    AACCTGGTCTGTGCCCAAAATTAGTCACTTCTCGACACGGAAGCACAGGG 2660      2670      2680      2690      2700
    AGCTGAAGAAGAGGCATACATTCACTGCAGGCACAGAGCCAAGGGAGAAG
    TCGACTTCTTCTCCGTATGTAAGTGACGTCCGTGTCTCGGTTCCCTCTTC 2710      2720      2730      2740      2750
    GAACACTGTCTCAGAGTGCTTTTACCTAGCCCAGGGACATCTCAAGGAAG
    CTTGTGACAGAGTCTCACGAAAATGGATCGGGTCCCTGTAGAGTTCCTTC 2760      2770      2780      2790      2800
    CCAGCCGTTAAAATGCCTGTGTTTGGTGAGAGACCCTGGCGAGCATGAAG
    GGTCGGCAATTTTACGGACACAAACCACTCTCTGGGACCGCTCGTACTTC 2810      2820      2830      2840      2850
    CAGGCCCTGTGTAGCACTGACTGCAGTTGGAGAAGCAGAGATAGTTAATG
    GTCCGGGACACATCGTGACTGACGTCAACCTCTTCGTCTCTATCAATTAC 2860      2870      2880      2890      2900
    AGACCTGGTGCCTGTGGACCTCCTGTTGAGTGATCAAAAGGGGAATTTGA
    TCTGGACCACGGACACCTGGAGGACAACTCACTAGTTTTCCCCTTAAACT 2910      2920      2930      2940      2950
    TTCATTCTGTCCCCTTTCCCATTTGGCTGGCCTGTAGTCACAGTGAGGTC
    AAGTAAGACAGGGGAAAGGGTAAACCGACCGGACATCAGTGTCACTCCAG 2960      2970      2980      2990      3000
    GGCATATCTGTGTCAGACACAGTAGCAAAGCAAGTTAAAATTCCCAAAGG
    CCGTATAGACACAGTCTGTGTCATCGTTTCGTTCAATTTTAAGGGTTTCC
```

FIGURE 4f

```
           3010        3020        3030        3040        3050
    AAAAAGAGCCTTGACGTCCACTTTGATTTGCGCTGGACCCATAGTTGTAG
    TTTTTCTCGGAACTGCAGGTGAAACTAAACGCGACCTGGGTATCAACATC 3060        3070        3080        3090        3100
    CTGAAAAGGATCAAACAGAGGAAATCTGTTCAGCTTTTGAATTGGGCTAA
    GACTTTTCCTAGTTTGTCTCCTTTAGACAAGTCGAAAACTTAACCCGATT 3110        3120        3130        3140        3150
    ATTGAGTTCTCTTACCCTTAAGCTACAGTGGAGTTGTCCAAGAATCGTAA
    TAACTCAAGAGAATGGGAATTCGATGTCACCTCAACAGGTTCTTAGCATT 3160        3170        3180        3190        3200
    ATATAGTGGACAAAAATAGTCCAGGGTGATTAAAGCCTTTTTGGAACTCT
    TATATCACCTGTTTTTATCAGGTCCCACTAATTTCGGAAAAACCTTGAGA 3210        3220        3230        3240        3250
    TGCTCCCATTTTCCAGTTACATGTGTCTTACCCGATTTGACCATGTGAAG
    ACGAGGGTAAAAGGTCAATGTACACAGAATGGGCTAAACTGGTACACTTC 3260        3270        3280        3290        3300
    ATTTCGGTTCTGTATCTTATCTTGCCTTGGACACAAATGTAGTACAGTTA
    TAAAGCCAAGACATAGAATAGAACGGAACCTGTGTTTACATCATGTCAAT 3310        3320        3330        3340        3350
    ACAGCTAATTCTTTGCGTGTGTAATTTCCCATTGTATCAAACTAATTGAG
    TGTCGATTAAGAAACGCACACATTAAAGGGTAACATAGTTTGATTAACTC 3360        3370        3380        3390        3400
    TTTCCGTCTTTCTTGACACAGTCTGATGTGCAAGAATTGTCTCATGTATT
    AAAGGCAGAAAGAACTGTGTCAGACTACACGTTCTTAACAGAGTACATAA 3410        3420        3430        3440        3450
    TCAGTAATTATCAGGTCATAGAGTTATCCTTCCTCTAATGTATCCAACCA
    AGTCATTAATAGTCCAGTATCTCAATAGGAAGGAGATTACATAGGTTGGT 3460        3470        3480        3490        3500
    TCTAATCTGTGATTATACTTGTGGAAACCTTCTTTCTTGCGGTCTCCAAG
    AGATTAGACACTAATATGAACACCTTTGGAAGAAAGAACGCCAGAGGTTC 3510        3520        3530        3540        3550
    GGCTCTTTCACAGACCTGTGAGGTACCCTCTAAGTATTGGTTCCTGAACA
    CCGAGAAAGTGTCTGGACACTCCATGGGAGATTCATAACCAAGGACTTGT 3560        3570        3580        3590        3600
    TCAGCACACTTGGCTGCCTCTGTAGGTTCTTGGAATTGAGTCTCCTCCTG
    AGTCGTGTGAACCGACGGAGACATCCAAGAACCTTAACTCAGAGGAGGAC
```

FIGURE 4g

```
        3610        3620        3630        3640        3650
CAGTTGAATGTCACCCCTTCTCCACTTCTGGCACGGATACCTAGCAATCT
GTCAACTTACAGTGGGGAAGAGGTGAAGACCGTGCCTATGGATCGTTAGA 3660        3670        3680        3690        3700
CTGTGCACCATTCCAGGAAGCTGGGATCCTGTCTGTAGACCTATGCCAGG
GACACGTGGTAAGGTCCTTCGACCCTAGGACAGACATCTGGATACGGTCC 3710        3720        3730        3740        3750
AGCAACTCTCCGTTTCCTCTTCCTTTCTCCTCCTCTTTGTCTCTCGCCAC
TCGTTGAGAGGCAAAGGAGAAGGAAAGAGGAGGAGAAACAGAGAGCGGTG 3760        3770        3780        3790        3800
TCTCCCCAGGCCTCAGTTTCTTTAAGTCCTCTAAGCTTTCACAAAATGCT
AGAGGGGTCCGGAGTCAAAGAAATTCAGGAGATTCGAAAGTGTTTTACGA 3810        3820        3830        3840        3850
GGAAAGAGATCATCACCAAGCGGTTAGCATCCTTCTCAGAACTGAAGAGG
CCTTTCTCTAGTAGTGGTTCGCCAATCGTAGGAAGAGTCTTGACTTCTCC 3860        3870        3880        3890        3900
AAGGACTACAGATGATGAAGCTGTAGTGAATCTGTTGTCTCCATTTTAGG
TTCCTGATGTCTACTACTTCGACATCACTTAGACAACAGAGGTAAAATCC 3910        3920        3930        3940        3950
TAATTTCGTGAGTGTAAATTCAAATTCAAATAAATTGTGTTTATTTACTC
ATTAAAGCACTCACATTTAAGTTTAAGTTTATTTAACACAAATAAATGAG 3960        3970        3980        3990
AGAGCCTGATTGATTTATTTGCACTTTGAATTC
TCTCGGACTAACTAAATAAACGTGAAACTTAAG
                                EcoRI
```

FIGURE 5a

```
          10        20        30        40        50
AAGCTTGTTTGTCTTTAAGATACGGAAACGCATTTAAAAATTATACATTT
TTCGAACAAACAGAAATTCTATGCCTTTGCGTAAATTTTAATATGTAAA
HindIII
          60        70        80        90       100
GCTGAAAAAGATGCAGCTGGTGTGTGGTTAACTTAGAATTCCAGTTTAAT
CGACTTTTTCTACGTCGACCACACACCAATTGAATCTTAAGGTCAAATTA
                                     EcoRI
         110       120       130       140       150
CTTCTTTGACTCCAAAGTCCATATTTCTAAACACTGTAAAATAGTGCTTT
GAAGAAACTGAGGTTTCAGGTATAAAGATTTGTGACATTTTATCACGAAA 160       170       180       190       200
TGTAAAAAAATTGTCCTTTACATGTGATTTCACCTAATGATCAGTGGTGG
ACATTTTTTAACAGGAAATGTACACTAAAGTGGATTACTAGTCACCACC 210       220       230       240       250
TTTTTTTTTTTTTTCTTTCTTTCTTTAAATAGAAAATATTAAAATCAAC
AAAAAAAAAAAAAAGAAAGAAAGAAATTTATCTTTTATAATTTTAGTTG 260       270       280       290       300
ATGGGACAAAGCTACGATTCTCGAGTCATGTAGACTTGTAGTCATAGGTT
TACCCTGTTTCGATGCTAAGAGCTCAGTACATCTGAACATCAGTATCCAA 310       320       330       340       350
TTTCAGCTGTCATTTAGTCTCTTTGATGCTAAATGTCTTTATCTGTAAGA
AAAGTCGACAGTAAATCAGAGAAACTACGATTTACAGAAATAGACATTCT 360       370       380       390       400
TAAGGGTGTTTATAACTACCTTAGAGTTTTGGAGACAAACAAATAGCACA
ATTCCCACAAATATTGATGGAATCTCAAAACCTCTGTTTGTTTATCGTGT 410       420       430       440       450
TTTTCTGTACTTAAATAATATGTAGTATATTTATACTTAGGTGGCAGTTT
AAAAGACATGAATTTATTATACATCATATAAATATGAATCCACCGTCAAA 460       470       480       490       500
ATTTCAAGGAAGCACTGGGACTTGTGGCCACATCCTCCAAGATTAAAAAA
TAAAGTTCCTTCGTGACCCTGAACACCGGTGTAGGAGGTTCTAATTTTTT 510       520       530       540       550
AAAGTACTTAAAATATGGAACGACCATGTATGTTACGTGAAAAAGAACAG
TTTCATGAATTTTATACCTTGCTGGTACATACAATGCACTTTTTCTTGTC 560       570       580       590       600
GAGCCAGAACCACAGAAAAGCAAGGGAGAAGCCAAATAAGTAGATGATGA
CTCGGTCTTGGTGTCTTTTCGTTCCCTCTTCGGTTTATTCATCTACTACT
```

FIGURE 5b

```
         610        620        630        640        650
ACACGCTGAACTGATCTTTTTGGAGTGGAACATGTAAATGAAGATGCTGA
TGTGCGACTTGACTAGAAAAACCTCACCTTGTACATTTACTTCTACGACT 660        670        680        690        700
TGTGATCTTTGTGGGGATGACCTCAAATCCAAAACCAGTCATTTCAAACA
ACACTAGAAACACCCCTACTGGAGTTTAGGTTTTGGTCAGTAAAGTTTGT 710        720        730        740        750
TACTGAACAGAGTTACCCCAGATTCTTGTTCAAGGAGAAAAAGTATGGT
ATGACTTGTCTCAATGGGGTCTAAGAACAAGTTCCTCTTTTTTCATACCA 760        770        780        790        800
CACTTCAGGAAAGATAATGCTCAGAAATTACAGCCTGTTAATCATGTGAC
GTGAAGTCCTTTCTATTACGAGTCTTTAATGTCGGACAATTAGTACACTG 810        820        830        840        850
TCCTGCATCAGAAGCAAAGACTGTCTTGCCACTTTCTGTCTCTGAATCAA
AGGACGTAGTCTTCGTTTCTGACAGAACGGTGAAAGACAGAGACTTAGTT 860        870        880        890        900
GATCAACAGATAGTCCTATTATTATTGAGCCTTTGTCCAAAGCAGATTCT
CTAGTTGTCTATCAGGATAATAATAACTCGGAAACAGGTTTCGTCTAAGA 910        920        930        940        950
AAAAATATTTCACCACAAATAGTGCCTAATAGCTTTTCAGAGTTATGTTC
TTTTTATAAAGTGGTGTTTATCACGGATTATCGAAAGTCTCAATACAAG 960        970        980        990       1000
TCCTTTGATTACCTTCACAAGTTCATTGCAGGATCCAGTAGAAACAGCAG
AGGAAACTAATGGAAGTGTTCAAGTAACGTCCTAGGTCATCTTTGTCGTC
                                 BamHI
        1010       1020       1030       1040       1050
TTATGCAGGAGCTATGGATAAAAGTCCTCATGTATCAAAGTGACTTTCCA
AATACGTCCTCGATACCTATTTTCAGGAGTACATAGTTTCACTGAAAGGT 1060       1070       1080       1090       1100
CTTCTGAAACAAATAGCACAAATCCCAAAAGGCCTAAACTCAGTGATGGA
GAAGACTTTGTTTATCGTGTTTAGGGTTTTCCGGATTTGAGTCACTACCT 1110       1120       1130       1140       1150
ATTATAGGAGAACATTCTTTAGCTTTGTGCCCTCCAGATATTTTTCAAAC
TAATATCCTCTTGTAAGAAATCGAAACACGGGAGGTCTATAAAAAGTTTG 1160       1170       1180       1190       1200
AGTGACTACTCAGCAAAGCACACCAGACAGTGTTCATACCTCATTAAGCC
TCACTGATGAGTCGTTTCGTGTGGTCTGTCACAAGTATGGAGTAATTCGG
```

FIGURE 5c

```
          1210        1220        1230        1240        1250
ATGTTCAGAATGGAGAATCTTATCCAACACATTTTCTAAAGGACAATGTC
TACAAGTCTTACCTCTTAGAATAGGTTGTGTAAAAGATTTCCTGTTACAG 1260        1270        1280        1290        1300
CATTGCAAACCTATAAGCCCTTTAGGGTCAAATGGACTGACAAAAATTGA
GTAACGTTTGGATATTCGGGAAATCCCAGTTTACCTGACTGTTTTTAACT 1310        1320        1330        1340        1350
CTTTCCAAGTGTAGCAAGTCAAAACAAGATTGTTGATCCCACAGAAGGCA
GAAAGGTTCACATCGTTCAGTTTTGTTCTAACAACTAGGGTGTCTTCCGT 1360        1370        1380        1390        1400
ATCTGATTGTGTTACTCTGTGACTTCTACTATGGACAGCATATAGGAGAT
TAGACTAACACAATGAGACACTGAAGATGATACCTGTCGTATATCCTCTA 1410        1420        1430        1440        1450
GGGGCAGCCAGAACCGAAAACTCACACAGCCTTTAAATGCCTCAGCTGCT
CCCCGTCGGTCTTGGCTTTTGAGTGTGTCGGAAATTTACGGAGTCGACGA 1460        1470        1480        1490        1500
TGAAAGTTCTAAAAAATGTCAAGTTTATGAATCACATGAAGCACCATTTG
ACTTTCAAGATTTTTTACAGTTCAAATACTTAGTGTACTTCGTGGTAAAC 1510        1520        1530        1540        1550
GAGCTTGAGAGGCAGAGAGGTGACAGCTGGAAATACCACACCACCTGCCA
CTCGAACTCTCCGTCTCTCCACTGTCGACCTTTATGGTGTGGTGGACGGT 1560        1570        1580        1590        1600
GCACTGCAACTGCCAGTTTCCTACTCCCTTCCAGCTGCAGTGTCACATTG
CGTGACGTTGACGGTCAAAGGATGAGGGAAGGTCGACGTCACAGTGTAAC 1610        1620        1630        1640        1650
AAAGTGTCCATACTTCCCAGGAGCCCTCTGCAGTCTGTAAAATCTGTGAA
TTTCACAGGTATGAAGGGTCCTCGGGAGACGTCAGACATTTTAGACACTT 1660        1670        1680        1690        1700
TTGTCCTTTGAGACAGATCGGGTTCTCTAACAGCACATGAAAGATAATCA
AACAGGAAACTCTGTCTAGCCCAAGAGATTGTCGTGTACTTTCTATTAGT 1710        1720        1730        1740        1750
TAAGCCTGGTGAAATGCCCTATGTATGCCAGGTTTGCAGTTACAGATCAT
ATTCGGACCACTTTACGGGATACATACGGTCCAAACGTCAATGTCTAGTA 1760        1770        1780        1790        1800
CATTCTTTGCAGATGTGGATGCACATTTCAGAGCATACCATGGTAACATT
GTAAGAAACGTCTACACCTACGTGTAAAGTCTCGTATGGTACCATTGTAA
```

FIGURE 5d

```
         1810       1820       1830       1840       1850
AAGAGTTTACTTTGCCCCTTTTGTCTTCAAATGTTTAAAACTGCAAGACC
TTCTCAAATGAAACGGGGAAAACAGAAGTTTACAAATTTTGACGTTCTGG 1860       1870       1880       1890       1900
ATACATATGTCATTATAGACAGCACTGGGAAAAGTTTTCATCAGTGTTCC
TATGTATACAGTAATATCTGTCGTGACCCTTTTCAAAAGTAGTCACAAGG 1910       1920       1930       1940       1950
AAATGTAGGCTACACTTTTTAACTTTTAAAGAGAAAAGACAGCACAAGAC
TTTACATCCGATGTGAAAAATTGAAAATTTCTCTTTTCTGTCGTGTTCTG 1960       1970       1980       1990       2000
CCAGTGTCATCAAATGTTTAAGAAGCCTAAGCATCTAGAAGGATTACCTC
GGTCACAGTAGTTTACAAATTCTTCGGATTCGTAGATCTTCCTAATGGAG 2010       2020       2030       2040       2050
CTGAAACAAGAGTTTTTTTTCAGGTATCACCGGAACCCCTTCAACAGGAT
GACTTTGTTCTCAAAAAAAGTCCATAGTGGCCTTGGGGAAGTTGTCCTA 2060       2070       2080       2090       2100
TGGTGGAAGTAGCATCCAATACTGTGAACACATCTGATTCTGAACCATCA
ACCACCTTCATCGTAGGTTATGACACTTGTGTAGACTAAGACTTGGTAGT 2110       2120       2130       2140       2150
TCTCCCAAATCTAAAAGTAGGAGGCCAAAAAAAAAAAAAAACCAAAAAAC
AGAGGGTTTAGATTTTCATCCTCCGGTTTTTTTTTTTTTTGGTTTTTTG 2160       2170       2180       2190       2200
CCCGTTAATTCTACTTTCAGTAAGTCTGAAGCAAGTATTTCAGTCAAAGT
GGGCAATTAAGATGAAAGTCATTCAGACTTCGTTCATAAAGTCAGTTTCA 2210       2220       2230       2240       2250
TAAAAACCCCATTAAAAACAAAAAATTCAAATTTTAGAATTATTCAATAA
ATTTTTGGGGTAATTTTGTTTTTAAGTTTAAAATCTTAATAAGTTATT 2260       2270       2280       2290       2300
TATCAAATATAGGGCAACCAATGTGTAATTTATGTGTTTTGTTTTAAAT
ATAGTTTATATCCCGTTGGTTACACATTAAATACACAAAAACAAAATTTA 2310       2320       2330       2340       2350
ACATGAAGTACAGCTTTGTTTAAATATTGAGATGTTATTTAAAAATATAG
TGTACTTCATGTCGAAACAAATTTATAACTCTACAATAAATTTTTATATC 2360       2370       2380       2390       2400
TACCTGTTTTTCATATAAGTGTTTTAACATGTAAAAATTATGTGTGTGTG
ATGGACAAAAAGTATATTCACAAAATTGTACATTTTAATACACACAC
```

FIGURE 5e

```
         2410      2420      2430      2440      2450
TGTGAGAGAGAGAGAGAGAGAGAGGTGGAGAAAGGAAAAGTAACAACG
ACACTCTCTCTCTCTCTCTCTCCACCTCTTTCCTTTTCATTGTTGC 2460      2470      2480      2490      2500
TATTTTGGTATTTCATGTTATTTGCAAGTTCGAAAGCTCTGCTGCTGCTG
ATAAAACCATAAAGTACAATAAACGTTCAAGCTTTCGAGACGACGACGAC 2510      2520      2530      2540      2550
CTACTGCTGCTGCTAAGTTGCTTCAGACATGTTCGACTCTGTGCGACCCC
GATGACGACGACGATTCAACGAAGTCTGTACAAGCTGAGACACGCTGGGG 2560      2570      2580      2590      2600
ATAGACAGCAGCCCACCAAGATACCCTGTCCCTGGGATTCTCCAGGCAAG
TATCTGTCGTCGGGTGGTTCTATGGGACAGGGACCCTAAGAGGTCCGTTC 2610      2620      2630      2640      2650
AACACTGGAGTGGGTTGCCACTTCCTTCTCGAATGTATGAAAATGAAAAG
TTGTGACCTCACCCAACGGTGAAGGAAGAGCTTACATACTTTTACTTTTC 2660      2670      2680      2690      2700
TGAATGTGAAGTCACTCCATCGTGCCCGACTCTTAGCAACCCCATGGACT
ACTTACACTTCAGTGAGGTAGCACGGGCTGAGAATCGTTGGGGTACCTGA 2710      2720      2730      2740      2750
TCAGCCCACCAGGCTCCTCCATCTGTAGGATTTTTCCCACAAGAGTACTG
AGTCGGGTGGTCCGAGGAGGTAGACATCCTAAAAAGGGTGTTCTCATGAC 2760      2770      2780      2790      2800
GAGTGGGGTGCCATTGCCTTCTCCACTATACATATAATCTGTAGAGTGTT
CTCACCCCACGGTAACGGAAGAGGTGATATGTATATTAGACATCTCACAA 2810      2820      2830      2840      2850
TAGCAATGAAATTTTCAACTGTTTTCATGCTTTGAAGATCTCAGTATTAA
ATCGTTACTTTAAAAGTTGACAAAAGTACGAAACTTCTAGAGTCATAATT 2860      2870      2880      2890      2900
CTATATAGCCAGATTGGAATGGCTTTGTTATGGTATGGTCCTGTGTGCTG
GATATATCGGTCTAACCTTACCGAAACAATACCATACCAGGACACACGAC 2910      2920      2930      2940      2950
CTGAACTCTCCGAAGTGCCTCTGTTGTGCTGTTCTAAGATAAAATGGTTC
GACTTGAGAGGCTTCACGGAGACAACACGACAAGATTCTATTTTACCAAG 2960      2970      2980      2990      3000
CGAAAGCCTGATGTGGAGAAGTTGATGGAGAAACTATGATGTGAGTTTGG
GCTTTCGGACTACACCTCTTCAACTACCTCTTTGATACTACACTCAAACC
```

FIGURE 5f

```
         3010      3020      3030      3040      3050
ACCAGACACGGGATTTAGTTAGTGGAGAGCTGTGGCTTCTTGTCCCAGTT
TGGTCTGTGCCCTAAATCAATCACCTCTCGACACCGAAGAACAGGGTCAA 3060      3070      3080      3090      3100
GAGGAAGAGGCATGCATGCACTCCAGGCATGGAGCCAAGGCAGAAGGAAC
CTCCTTCTCCGTACGTACGTGAGGTCCGTACCTCGGTTCCGTCTTCCTTG 3110      3120      3130      3140      3150
ACTGTCTCAGAGTGTCTTAACCTAGCCCAGGGACATGTCAAGGAAGCCAA
TGACAGAGTCTCACAGAATTGGATCGGGTCCCTGTACAGTTCCTTCGGTT 3160      3170      3180      3190      3200
CCACTAAAATGCCTGTTAGGTGAGAGGCACTTGCAAGGATCAAGCAGGCC
GGTGATTTTACGGACAATCCACTCTCCGTGAACGTTCCTAGTTCGTCCGG 3210      3220      3230      3240      3250
CTGTATATCATTGACTGCAGTTGGAGAAGCAGAGATAGTTAATAGAATGA
GACATATAGTAACTGACGTCAACCTCTTCGTCTCTATCAATTATCTTACT 3260      3270      3280      3290      3300
GGCCTGGTGCCTGTGGACCTCCTGTTGAGTGATCAAAAGGGGAATTTGAT
CCGGACCACGGACACCTGGAGGACAACTCACTAGTTTTCCCCTTAAACTA 3310      3320      3330      3340      3350
TCATTCCATCTCCTTTCCCATTTGGCTGGCCTTTAGTCAAAGTGAAGTAG
AGTAAGGTAGAGGAAAGGGTAAACCGACCGGAAATCAGTTTCACTTCATC 3360      3370      3380      3390      3400
CCCTATCCGTCTCCATCACAATAGTAAAGCAAGTTAAGATTCCCAAAGAA
GGGATAGGCAGAGGTAGTGTTATCATTTCGTTCAATTCTAAGGGTTTCTT 3410      3420      3430      3440      3450
AAAAGCCTTGACATCCAGTTTGATTTGTACTGGACCCATAGGTTTAACTG
TTTTCGGAACTGTAGGTCAAACTAAACATGACCTGGGTATCCAAATTGAC 3460      3470      3480      3490      3500
AAAAGGATCAAACACAGGGAATCTTTTCAGTTTATGAATTGAGCTAAGTT
TTTTCCTAGTTTGTGTCCCTTAGAAAAGTCAAATACTTAACTCGATTCAA 3510      3520      3530      3540      3550
TAGTTCTCTTTCCCTTAAGCTACAAAGGAGTTGTCCGAGAAGAGTAAATG
ATCAAGAGAAAGGGAATTCGATGTTTCCTCAACAGGCTCTTCTCATTTAC 3560      3570      3580      3590      3600
TAGTGGATACAAAGGGTCCAGGGTGATTAAACCCTCTATAGAACTTTTCC
ATCACCTATGTTTCCCAGGTCCCACTAATTTGGGAGATATCTTGAAAAGG
```

FIGURE 5 g

```
        3610      3620      3630      3640      3650
TTACCTTTTCCAGTTACATGTGTCTTACCCTAGTTTAACGTGACAATTTC
AATGGAAAAGGTCAATGTACACAGAATGGGATCAAATTGCACTGTTAAAG 3660      3670      3680      3690      3700
ACTTTTGTATCTTATCTTGCCTTGGGCAGGAATGTATTAAAGTTAACAGC
TGAAAACATAGAATAGAACGGAACCCGTCCTTACATAATTTCAATTGTCG 3710      3720      3730      3740      3750
TAATTCTTTGTGTAATTTCCCATTTTATCAAACTAATACTGGGTTTCCAT
ATTAAGAAACACATTAAAGGGTAAAATAGTTTGATTATGACCCAAAGGTA 3760      3770      3780      3790      3800
CTTACTTGACACAGTCTGATGTGCAGGAATTTTCTCATTTATTTCAGTAA
GAATGAACTGTGTCAGACTACACGTCCTTAAAAGAGTAAATAAAGTCATT 3810      3820      3830      3840      3850
TTATCAGGTCATAGAGTTATCATCCTTCCTCTACTCTATCCAACTACCTA
AATAGTCCAGTATCTCAATAGTAGGAAGGAGATGAGATAGGTTGATGGAT 3860      3870      3880      3890      3900
GTCTGTGATTATACTTGTGGAAACCTTTTTCGTGTGATCTCCAAGGGCT
CAGACACTAATATGAACACCTTTGGAAAAAAGCACACTAGAGGTTCCCGA 3910      3920      3930      3940      3950
CTTTCACAGACCTGTGGTGTACCCTCTAAGTACTGGTTCCTGAACATCAG
GAAAGTGTCTGGACACCACATGGGAGATTCATGACCAAGGACTTGTAGTC 3960      3970      3980      3990      4000
CACACTTGGCTTCCTCTGTGGGTTCCTGGAGTTGAGTCTCCTCCTGGAGT
GTGTGAACCGAAGGAGACACCCAAGGACCTCAACTCAGAGGAGGACCTCA 4010      4020      4030      4040      4050
TGAATGCCATACCTTCTCCACTTCTGGCACAGATATCTAGAATCTCTGTG
ACTTACGGTATGGAAGAGGTGAAGACCGTGTCTATAGATCTTAGAGACAC 4060      4070      4080      4090      4100
CACCATTCAAGGAACCTGGAATCTTGGCTGTAGACCTATGTCAAGAGAAA
GTGGTAAGTTCCTTGGACCTTAGAACCGACATCTGGATACAGTTCTCTTT 4110      4120      4130      4140      4150
TCTCTCCATTTCCTCTTCCTTTCTCCTCCTCTTTGTCTCTCCCCACTCTT
AGAGAGGTAAAGGAGAAGGAAAGAGGAGGAGAAACAGAGAGGGGTGAGAA 4160      4170      4180      4190
TCTGCCCCTCCCCACAATTCATTTAAATCCTCTAAGCTT
AGACGGGGAGGGGTGTTAAGTAAATTTAGGAGATTCGAA
```

FIGURE 6a

```
             10         20         30         40         50
     AAGCTTGTTTGTCTTTAAGATACGGAAACACATTTAAAAATTATAAATTT
     TTCGAACAAACAGAAATTCTATGCCTTTGTGTAAATTTTTAATATTTAAA
     HindIII
             60         70         80         90        100
     GCCGAAAAAGATGCAGCTGGTGTGTGGTTAACTTAGAATTCCAGTTTAAT
     CGGCTTTTTCTACGTCGACCACACACCAATTGAATCTTAAGGTCAAATTA
                                             EcoRI
            110        120        130        140        150
     CTTCTTTGACTCCAAAGTCCATGTTTCTAAACAGTGTAAAATAGTGCTTT
     GAAGAAACTGAGGTTTCAGGTACAAAGATTTGTCACATTTTATCACGAAA 160        170        180        190        200
     TGTAAAAGATTTGTCTTTTACATGTGATTTGACCTAATGATGAGTGGTG
     ACATTTTCTAAACAGAAAATGTACACTAAACTGGATTACTACTCACCAC 210        220        230        240        250
     TTTTTTTTTTTTCCTTTCTTTCTTTTTTAAATAGAAAAGATTAAAAT
     AAAAAAAAAAAAAGGAAAGAAAGAAAAAATTTATCTTTTCTAATTTTA 260        270        280        290        300
     CAACATGGGACAAAGCTATGATTCTCGAGTCATGTAGACTTGTAGTCATA
     GTTGTACCCTGTTTCGATACTAAGAGCTCAGTACATCTGAACATCAGTAT 310        320        330        340        350
     GGTTTTTCCGCTGCCATTTAGTCTCTTTGATGCTAAATGTCCTTATCTGT
     CCAAAAAGGCGACGGTAAATCAGAGAAACTACGATTTACAGGAATAGACA 360        370        380        390        400
     AAGATAAGGGTGTTTATAACTCCCCTAGAGTTTTGGAGATAAACAAATAG
     TTCTATTCCCACAAATATTGAGGGGATCTCAAAACCTCTATTTGTTTATC 410        420        430        440        450
     CACATTGTTCTGTACTTAGCTAATATGTAATATATTTATACTTAGGTGGA
     GTGTAACAAGACATGAATCGATTATACATTATATAAATATGAATCCACCT 460        470        480        490        500
     AGTTTATTTAAAGGAAGCACTGGGACTTGTGGCCACATCCTCCAAGAATA
     TCAAATAAATTTCCTTCGTGACCCTGAACACCGGTGTAGGAGGTTCTTAT 510        520        530        540        550
     AAAGAAAAAAGTACTTAAAATATGGAACGACCATGTATGTGAAAAAGAA
     TTTCTTTTTTTCATGAATTTTATACCTTGCTGGTACATACACTTTTTCTT 560        570        580        590        600
     CAAGAGCCAGAACCACAGAAAAGCGAGGGAGAAACCAAACAAGTAGATGA
     GTTCTCGGTCTTGGTGTCTTTTCGCTCCCTCTTTGGTTTGTTCATCTACT
```

FIGURE 6b

```
        610        620        630        640        650
TGAAGATGCTGAACTGATCTTGTTTGGAGTGGAACATGTAAATGAAGATG
ACTTCTACGACTTGACTAGAACAAACCTCACCTTGTACATTTACTTCTAC 660        670        680        690        700
CTGATGTGATCTTTGTGGGGATGACCTCAAATTCAAAATCAGTTGTTTCA
GACTACACTAGAAACACCCCTACTGGAGTTTAAGTTTTAGTCAACAAAGT 710        720        730        740        750
AACATACTGAACAGAGTTACCCCAGGTTCTTGTTCAAGGAGAAAAAGTA
TTGTATGACTTGTCTCAATGGGGTCCAAGAACAAGTTCCTCTTTTTTCAT 760        770        780        790        800
TGTTCACTTCAGGAAAGATAATGCTCAGAAATTACAGTGTGTTAGTCATG
ACAAGTGAAGTCCTTTCTATTACGAGTCTTTAATGTCACACAATCAGTAC 810        820        830        840        850
TGACTCCTGCATCAGAAGCAAAGACTGTCTTGCCTCTTTCTGTCTCTGAA
ACTGAGGACGTAGTCTTCGTTTCTGACAGAACGGAGAAAGACAGAGACTT 860        870        880        890        900
TCAAGATCAACATATAGTCCTATTATTATTGAGCCTTTGTCCAAAGCGGA
AGTTCTAGTTGTATATCAGGATAATAATAACTCGGAAACAGGTTTCGCCT 910        920        930        940        950
CTATAAAAATATTTCACCACAAATAGTGCCTAACAGCTTTTCAGAGTTAT
GATATTTTATAAAGTGGTGTTTATCACGGATTGTCGAAAAGTCTCAATA 960        970        980        990        1000
GTTCTCCTTTGATTACCTTCACAAGTTCATTGCAGCATCCAGTAGAAACA
CAAGAGGAAACTAATGGAAGTGTTCAAGTAACGTCGTAGGTCATCTTTGT 1010       1020       1030       1040       1050
GCAGTTACTGCAGGAGCTATGGATAAAATTGCTCATATATCAAAGTGACT
CGTCAATGACGTCCTCGATACCTATTTTAACGAGTATATAGTTTCACTGA 1060       1070       1080       1090       1100
TTCCACTTCTGAAACAAATAGCAATAAATCCCAAAAGGCCTAAACTCAGT
AAGGTGAAGACTTTGTTTATCGTTATTTAGGGTTTTCCGGATTTGAGTCA 1110       1120       1130       1140       1150
GATGGAATTATAGGAGAACATTCTTTAGCTTTGTCCCCTCCAGGTATTTT
CTACCTTAATATCCTCTTGTAAGAAATCGAAACAGGGGAGGTCCATAAAA 1160       1170       1180       1190       1200
TCAAACAGTGACTACTCATCAAAGCACACCAGACAGTGTTCATACCTCAG
AGTTTGTCACTGATGAGTAGTTTCGTGTGGTCTGTCACAAGTATGGAGTC
```

FIGURE 6c

```
        1210      1220      1230      1240      1250
TAAGCCATGTTCAGAATGGAGAATCTTGTCCAACACATTTTCCAAAGGAC
ATTCGGTACAAGTCTTACCTCTTAGAACAGGTTGTGTAAAAGGTTTCCTG 1260      1270      1280      1290      1300
AATGTCCATTGCAAGCCTATAAGTGCTTTAGGGTAAAATGGACTGACAAA
TTACAGGTAACGTTCGGATATTCACGAAATCCCATTTTACCTGACTGTTT 1310      1320      1330      1340      1350
AATTGACTTTCCAAGTGTAGCAAGTCAAAACAAGATTGTTGATCCCACAG
TTAACTGAAAGGTTCACATCGTTCAGTTTTGTTCTAACAACTAGGGTGTC 1360      1370      1380      1390      1400
AAGGCAATCTGATTGTGTTACTCTGTGATTTCTACTATGGACAGCATATA
TTCCGTTAGACTAACACAATGAGACACTAAAGATGATACCTGTCGTATAT 1410      1420      1430      1440      1450
GGAGATAGGCAGCCAGAACCGCAAACTCACACAGCCTTTAAATGCCTCAG
CCTCTATCCGTCGGTCTTGGCGTTTGAGTGTGTCGGAAATTTACGGAGTC 1460      1470      1480      1490      1500
CTGCTTGAAAGTTCTAAAAAATGTCAAGTTTATGAATCACATGAAGCACC
GACGAACTTTCAAGATTTTTACAGTTCAAATACTTAGTGTACTTCGTGG 1510      1520      1530      1540      1550
ATTTGGAGCTTGAGAGGCAGAGAGGTGACAGCTGGAAATACCACACCACC
TAAACCTCGAACTCTCCGTCTCTCCACTGTCGACCTTTATGGTGTGGTGG 1560      1570      1580      1590      1600
TGCCAGCACTGCAACTGCCAGTTTCCTACTCCCTTCCAGCTGCAGTGTCA
ACGGTCGTGACGTTGACGGTCAAAGGATGAGGGAAGGTCGACGTCACAGT 1610      1620      1630      1640      1650
CATTGAAAGTGTCCACACTTCCCAGGAGCCCTCTGCAGTCTGTAAAATCT
GTAACTTTCACAGGTGTGAAGGGTCCTCGGGAGACGTCAGACATTTTAGA 1660      1670      1680      1690      1700
GTGAATTGTCCTTTGAGACAGATCGGGTTCTCTAACAGCACATGAAAGAT
CACTTAACAGGAAACTCTGTCTAGCCCAAGAGATTGTCGTGTACTTTCTA 1710      1720      1730      1740      1750
AATCATAAGCCTGGAGACATGCCCTATGCATGCCAGGTTTGCAGTTACAG
TTAGTATTCGGACCTCTGTACGGGATACGTACGGTCCAAACGTCAATGTC 1760      1770      1780      1790      1800
ATCATCATTCTTTGCAGATGTGGATGCACATTTCAGAGCTTACCATGGTA
TAGTAGTAAGAAACGTCTACACCTACGTGTAAAGTCTCGAATGGTACCAT
```

FIGURE 6d

```
          1810      1820      1830      1840      1850
     ACATTAAGAATTTACTTTGCCCCTTTTGTCTACAAATTTTAAAACTGCA
     TGTAATTCTTAAATGAAACGGGGAAAACAGATGTTTAAAAATTTTGACGT 1860      1870      1880      1890      1900
     ACACCATACATATGCCATTATAGACAGCACTAGGAAAAGTTTTCATCAGT
     TGTGGTATGTATACGGTAATATCTGTCGTGATCCTTTTCAAAAGTAGTCA 1910      1920      1930      1940      1950
     GTTCCAAATGTCAGCTACACTTTTTAACTTTTAAAGAGAAAAGACAGCAC
     CAAGGTTTACAGTCGATGTGAAAAATTGAAAATTTCTCTTTTCTGTCGTG 1960      1970      1980      1990      2000
     AAGACCCAGTGTCATCAAATATATAAGAAGCCTCAGCATCTAGAAGGATT
     TTCTGGGTCACAGTAGTTTATATATTCTTCGGAGTCGTAGATCTTCCTAA 2010      2020      2030      2040      2050
     ACCTCCTGAAACAAGAGTTTTTATTCAGGTATCACTGGAACCCCTTCAAC
     TGGAGGACTTTGTTCTCAAAAATAAGTCCATAGTGACCTTGGGGAAGTTG 2060      2070      2080      2090      2100
     AAGATTGGTGGAAGTGGCATCCATTACTGTGAACACATCTGATTCTGAAC
     TTCTAACCACCTTCACCGTAGGTAATGACACTTGTGTAGACTAAGACTTG 2110      2120      2130      2140      2150
     CATCACCCCAAATCTAAAAGTAGGAGGTCAAAAAAAAAAAAAACATTAAT
     GTAGTGGGGTTTAGATTTTCATCCTCCAGTTTTTTTTTTTTGTAATTA 2160      2170      2180      2190      2200
     TCTGCTTTCAATAAGTCTGAAGCAAGTATTTCAGTCAAAGTTAAAAACCC
     AGACGAAAGTTATTCAGACTTCGTTCATAAAGTCAGTTTCAATTTTTGGG 2210      2220      2230      2240      2250
     CATTAAAAACAAAAAATTCAAATTATAGAATTATTCAATAATATCAAATA
     GTAATTTTGTTTTTAAGTTTAATATCTTAATAAGTTATTATAGTTTAT 2260      2270      2280      2290      2300
     TAGGGAAACCAATGTGTAATTTATGTGTTTTTATTTTAAATACATGACGT
     ATCCCTTTGGTTACACATTAAATACACAAAATAAAATTTATGTACTGCA 2310      2320      2330      2340      2350
     ACAGCTTTGTTTAAATATTGAGATGTTATTTAAAAATATAGTACCTGTTT
     TGTCGAAACAAATTTATAACTCTACAATAAATTTTTATATCATGGACAAA 2360      2370      2380      2390      2400
     TTCATATAAGTATTTTAACATGTAAAAATTATGTGTGCGTGTGTGTGTGT
     AAGTATATTCATAAAATTGTACATTTTAATACACACGCACACACACACA
```

FIGURE 6e

```
         2410      2420      2430      2440      2450
GTGTGTGAGTGTCAGAGAGAGAGAACGAGAGAGGTGGAGAAAGGAAAAGT
CACACACTCACAGTCTCTCTCTTGCTCTCTCCACCTCTTTCCTTTTCA 2460      2470      2480      2490      2500
AACAATGTTTTTGGTATTTCATGTTATTTGCAAGTTTGAAAGCTCTGCT
TTGTTACAAAAAACCATAAAGTACAATAAACGTTCAAACTTTCGAGACGA 2510      2520      2530      2540      2550
GCTGCTGCTACTGCTGCTGCTAAGTTGCTTCAGTCATGTTCGACTCTGTG
CGACGACGATGACGACGACGATTCAACGAAGTCAGTACAAGCTGAGACAC 2560      2570      2580      2590      2600
CGACCCCATAGACAGCAGCCCACCAGGCTACCCTGTCCCTGTTATTCTCC
GCTGGGGTATCTGTCGTCGGGTGGTCCGATGGGACAGGACAATAAGAGG 2610      2620      2630      2640      2650
AGGCAAGAACACTGGAGCGGGTTGCCATTTCCTTTTCCAATGTATAAAAA
TCCGTTCTTGTGACCTCGCCCAACGGTAAAGGAAAAGGTTACATATTTTT 2660      2670      2680      2690      2700
TGAAAAGTGAATGTGAAGTCACTCAGTCGTGCCCAACTCTTAGCAACCCC
ACTTTTCACTTACACTTCAGTGAGTCAGCACGGGTTGAGAATCGTTGGGG 2710      2720      2730      2740      2750
ATGGACTTCAGCCCACCAGGCTCCTCCATCCGTAGGATTTTTCCTGCAAG
TACCTGAAGTCGGGTGGTCCGAGGAGGTAGGCATCCTAAAAAGGACGTTC 2760      2770      2780      2790      2800
AGTACTGGAGTGGGGTGCCATTGCCTTCTTCACTATACATGTAATCTGTA
TCATGACCTCACCCCACGGTAACGGAAGAAGTGATATGTACATTAGACAT 2810      2820      2830      2840      2850
GAGTGTTTAGCAATGAAAATTTCAACTCTTTTCATGCCTTGAAGATCTCA
CTCACAAATCGTTACTTTTAAAGTTGAGAAAAGTACGGAACTTCTAGAGT 2860      2870      2880      2890      2900
GTATTAACTATATAGCCAGATTGGAATGGCTTTGTTATGGTATGGTCCTG
CATAATTGATATATCGGTCTAACCTTACCGAAACAATACCATACCAGGAC 2910      2920      2930      2940      2950
TGTGCTGCTGAACTCTGTGAAGTGCCTCTGTTGTGCTGTTCTAAGATAAA
ACACGACGACTTGAGACACTTCACGGAGACAACACGACAAGATTCTATTT 2960      2970      2980      2990      3000
ATGGTTCCAAAAGCCTGATGTGGAGAAGTTGATGGAGAAACTATGATGTG
TACCAAGGTTTTCGGACTACACCTCTTCAACTACCTCTTTGATACTACAC
```

FIGURE 6f

```
        3010      3020      3030      3040      3050
AGTTTGGACCAGACACGGGATTTAGTTAGTGGAGAGCTGTGGCTTCTTGT
TCAAACCTGGTCTGTGCCCTAAATCAATCACCTCTCGACACCGAAGAACA 3060      3070      3080      3090      3100
CCCAGTTGAGGAAGAGGCATGCATGCACTCCAGGCATGGAGCCAAGGCAG
GGGTCAACTCCTTCTCCGTACGTACGTGAGGTCCGTACCTCGGTTCCGTC 3110      3120      3130      3140      3150
AAGGAACACTGTCTGAGAGTGTCTTTACCTAGCCCAGGGACATCTCAAGG
TTCCTTGTGACAGACTCTCACAGAAATGGATCGGGTCCCTGTAGAGTTCC 3160      3170      3180      3190      3200
AAGCCAACCACTAAAATGCCTGTTAGGTGAGAGGCACCTGCAAGGATCAA
TTCGGTTGGTGATTTTACGGACAATCCACTCTCCGTGGACGTTCCTAGTT 3210      3220      3230      3240      3250
GCAGGACCTGTGTATCATTGACTGCAGTTGGAGAAGCAGAGACAGTTAAA
CGTCCTGGACACATAGTAACTGACGTCAACCTCTTCGTCTCTGTCAATTT 3260      3270      3280      3290      3300
GAATGAGGCCTGGTGCCTGTGGACCTCCTGTTGAGTGATCAAAAGGGGAA
CTTACTCCGGACCACGGACACCTGGAGGACAACTCACTAGTTTTCCCCTT 3310      3320      3330      3340      3350
TTTGATTCATTCCATCTCCTTTCCCATTTGGCTGGCCTTTAGTCAAAGTG
AAACTAAGTAAGGTAGAGGAAAGGGTAAACCGACCGGAAATCAGTTTCAC 3360      3370      3380      3390      3400
AAGTAGCCCTATCAGTCTCCATCACAGTAGTAAAGCAAGTTAAGATTCCC
TTCATCGGGATAGTCAGAGGTAGTGTCATCATTTCGTTCAATTCTAAGGG 3410      3420      3430      3440      3450
CAAGAAAAAAGCCTTGACATCCAGTTTGATTTGTACTGGACCCATAGTTT
GTTCTTTTTTCGGAACTGTAGGTCAAACTAAACATGACCTGGGTATCAAA 3460      3470      3480      3490      3500
TAACTGAAAAGGATCAAACACAGGGAACCTTTTCAGTTTATGAATTGAGC
ATTGACTTTTCCTAGTTTGTGTCCCTTGGAAAAGTCAAATACTTAACTCG 3510      3520      3530      3540      3550
TAAATTTAGTTCTCTTTCCCTTAAGCTACAAAGGAGTTATCTGAGAATAG
ATTTAAATCAAGAGAAAGGGAATTCGATGTTTCCTCAATAGACTCTTATC 3560      3570      3580      3590      3600
TAAATGTAGTGGATACAAAGGTGATTAAAGCCTCTATAGAACTTTTCCTT
ATTTACATCACCTATGTTTCCACTAATTTCGGAGATATCTTGAAAAGGAA
```

FIGURE 6g

```
      3610      3620      3630      3640      3650
ACATTTTCCAGTTACATGTGTCTTACCCTAGTTTAAACATGTGACGATTT
TGTAAAAGGTCAATGTACACAGAATGGGATCAAATTTGTACACTGCTAAA 3660      3670      3680      3690      3700
CAGTTTTGTATCTTATCTTGCCTTGGGCATGAATGTATTAAAGTTAACAG
GTCAAAACATAGAATAGAACGGAACCCGTACTTACATAATTTCAATTGTC 3710      3720      3730      3740      3750
CTAATTCTTTGTTTAATTTCCCATTTTATCAAACTAATACTTGGTTTCTG
GATTAAGAAACAAATTAAAGGGTAAATAGTTTGATTATGAACCAAAGAC 3760      3770      3780      3790      3800
TCTTACTTGACACAGTCTGATGTGCAGGAATTTTCTCATTTATTTCAGTA
AGAATGAACTGTGTCAGACTACACGTCCTTAAAAGAGTAAATAAAGTCAT 3810      3820      3830      3840      3850
ATTATCAGGTCATAGAGTTATCATCCTTCCTCTACTGTATCCAACTACCT
TAATAGTCCAGTATCTCAATAGTAGGAAGGAGATGACATAGGTTGATGGA 3860      3870      3880      3890      3900
AGTCTGTGATTATACTTGTGGAAACCTTTTTTCGTGTGATCTCCAAGGGC
TCAGACACTAATATGAACACCTTTGGAAAAAAGCACACTAGAGGTTCCCG 3910      3920      3930      3940      3950
TCTTTCACAGACCTGTGGTGTACCCTCTAAGTACTGGTTCCTGTGTTTCA
AGAAAGTGTCTGGACACCACATGGGAGATTCATGACCAAGGACACAAAGT 3960      3970      3980      3990      4000
GCACACTTGGCTTCCTCTGTGGGTTCCTGGAGTTGAGTCTCCTCCTGGAG
CGTGTGAACCGAAGGAGACACCCAAGGACCTCAACTCAGAGGAGGACCTC 4010      4020      4030      4040      4050
TTGAATGCCATACCTTCTCCACTTCTGGCACAGATACCTAGAATCTCTGT
AACTTACGGTATGGAAGAGGTGAAGACCGTGTCTATGGATCTTAGAGACA 4060      4070      4080      4090      4100
GCACCATTCAAGGAACCTGGAATCTTGGCTGTAGACCTATGCCAGGAGAA
CGTGGTAAGTTCCTTGGACCTTAGAACCGACATCTGGATACGGTCCTCTT 4110      4120      4130      4140      4150
ATCTCTCTGTTTCCTCTTCCTTTCTCCTCCTCTTGTCTCTCCCCACTCT
TAGAGAGACAAAGGAGAAGGAAAGAGGAGGAGAAACAGAGAGGGGTGAGA 4160      4170      4180      4190      4200
TTCCCCCCTGCCCCGACCCACCTCCACAATTCATTTAAATCCTCTAAGCT T
AAGGGGGGACGGGGCTGGGTGGAGGTGTTAAGTAAATTTAGGAGATTCGA A
```

FIGURE 7a

BRY4a:
```
        1340       1350        1360        1370        1380
GATTGTTGATCCCACAGAAGGCAATCTGATTGTGTTACTCTGTGACTTCTACT
     1390      1400       1410       1420       1430
ATGGACAGCATATAGGAGATGGGCAGCCAGAACCGAAAACTCACACAGCCTT
    1440       1450       1460
TAAATGCCTCAGCTGCTTGAAAGTTC
```

BRY4b:
```
        1340       1350        1360        1370        1380
GATTGTTGATCCCACAGAAGGCAATCTGATTGTGTTAGTCTGTGACTTCTACT
     1390      1400       1410       1420       1430
ATGGACAGCATATAGGAGAT.GGGCAGCCAGAACCGAAAACTCACACAGCCTT
    1440       1450       1460
TAAATGCCTCAGCTGCTTGAAAGTTC
```

BRY4c:
```
    1340       1350         1360        1370        1380
GATTGTTGATCCCACAGAAGGCAATCTGATTGTGTTACTCTGTGATTTCTACT
1390      1400       1410       1420       1430        1440
ATGGACAGCATATAGGAGATAGG.CAGCCAGAACCGCAAACTCACACAGCCTT
         1450       1460
TAAATGCCTCAGCTGCTTGAAAGTTC
```

BRY4d:
```
       1330        1340       1350       1360       1370
GATTGTTGATCCCACAGAAGGCAATCTGATTGTGTTAGTCTGTGACTTCTACT
     1380       1390       1400       1410       1420
ATGGACAGCATATAGGAGAT.GGGCAGCCAGAACCGAAAACT.ACACAGCCTT
     1430       1440       1450
TAAATGCCTCAGCTGCTTGAAAGTTC
```

BRY4e:
```
        1340       1350        1360        1370        1380
GATTGTTGATTCCACAGAAGGCAATCTGATTGTGTTACTCTGTGACTTCTACT
     1390      1400       1410       1420       1430
ATGGACAGCATATAGGAGATAGG.CAGCCAGAACTGCAAACTCACACAGCCTT
    1440       1450       1460
TAAATGCCTCAGCTGCTTGAAAGTTC
```

FIGURE 7b

GRY1a:
```
        80        90        100       110       120
GATTGTTGATCCCACAGAAGGAAATCTGATTGTGTTACTTCGTGACTTCTACT
   130       140       150       160       170
ATGGAGAGCTTATAGGAGTT.GGGCAGCCAGAACCGAAGACCCACACAGCGTT
  180       190       200
TAAATGCCTCAGCTGCTTGAAAGTTC
```

GRY1b:
```
GATTGTTGATCCCACAGAAGGAAATCTGATTGTGTTACTTCGTGACTTCTACT
   130       140       150       160       170
ATGGAGAGCTTATAGGAGTT.GGGCAGCCAGAACCGAAGACCCACACAGCGTT
  180       190       200
TAAATGCCTCAGCTGCTTGAAAGTTC
```

OY11.1:
```
      1260      1270      1280      1290      1300
AATTGGTGATCCCACAGAAGGAAATCTGATTGTGTTACTTCATGACTTCTACT
   1310      1320      1330      1340      1350
ATGGCGAGCATGGAGGAGTT.GGGCAGCCAGAAGCGAAGACCCACACCGCGTT
  1360      1370      1380
TAAATGCCTCAGCTGCTTGAAAGTTC
```

FIGURE 8

```
          10        20        30        40        50
TGAGACCTTTAGGGGAAAATGGACTGACAAAAACTGATTTTCCAAGTTTA
ACTCTGGAAATCCCCTTTTACCTGACTGTTTTGACTAAAAGGTTCAAAT 60        70        80        90        100
GCAAGTCCAAACAAGATTGTTGATCCCACAGAAGGAAATCTGATTGTGTA
CGTTCAGGTTTGTTCTAACAACTAGGGTGTCTTCCTTTAGACTAACACAT 110       120       130       140       150
CTTCGTGACTTCTACTATGGAGAGCTTATAGGAGTTGGGCAGCCAGAACC
GAAGCACTGAAGATGATACCTCTCGAATATCCTCAACCCGTCGGTCTTGG 160       170       180       190       200
GAAGACCCACACAGCGTTTAAATGCCTCAGCTGCTTGAAAGTTCTAAAAA
CTTCTGGGTGTGTCGCAAATTTACGGAGTCGACGAACTTTCAAGATTTTT 210       220       230       240       250
ATGTCAAGTTTATGAATCACATGAAGCGCCATTTGGAACTTGAGAGGCAG
TACAGTTCAAATACTTAGTGTACTTCGCGGTAAACTTGAACTCTCCGTC 260       270       280       290       300
AGAGGTGACAGCTGGAAAAACCACACCACCTGCCAGCACTGCCTCCGCCA
TCTCCACTGTCGACCTTTTTGGTGTGGTGGACGGTCGTGACGGAGGCGGT 310       320       330       340       350
GTTTCCTACTCCCTTCCAGCTGCAGTGTCACATTGAAAGTGTCACACTCC
CAAAGGATGAGGGAAGGTCGACGTCACAGTGTAACTTTCACAGTGTGAGG 360       370       380       390
CAGGGCCTCGCAGTCTGTCAAATCTGTGAGTTGT
GTCCCGGAGCGTCAGACAGTTTAGACACTCAACA
```

FIGURE 9

```
         10        20        30        40        50
TTGTAAGACCTTTAGGGGAAAATGGACTGACAAAAACTGATTTTCCAAGT
AACATTCTGGAAATCCCCTTTTACCTGACTGTTTTTGACTAAAAGGTTCA 60        70        80        90       100
TTAGCAAGTCCAAACAAGATTGTTGATCCCACAGAAGGAAATCTGATTGT
AATCGTTCAGGTTTGTTCTAACAACTAGGGTGTCTTCCTTTAGACTAACA 110       120       130       140       150
GTTACTTCGTGACTTCTACTATGGAGAGCTTATAGGAGTTGGGCAGCCAG
CAATGAAGCACTGAAGATGATACCTCTCGAATATCCTCAACCCGTCGGTC 160       170       180       190       200
AACCGAAGACCCACACAGCGTTTAAATGCCTCAGCTGCTTGAAAGTTCTA
TTGGCTTCTGGGTGTGTCGCAAATTTACGGAGTCGACGAACTTTCAAGAT 210       220       230       240       250
AAAAATGTCAAGTTTATGAATCACATGAAGCGCCATTTGGAACTTGAGAG
TTTTTACAGTTCAAATACTTAGTGTACTTCGCGGTAAACCTTGAACTCTC 260       270       280       290       300
GCAGAGAGGTGACAGCTGGAAAACCACACCACCTGCCAGCACTGCCTCCG
CGTCTCTCCACTGTCGACCTTTTGGTGTGGTGGACGGTCGTGACGGAGGC 310       320       330       340       350
CCAGTTCCTACTCCCTTCCAGCTGCAGTGTCACATTGAAGTGTCACACTC
GGTCAAGGATGAGGGAAGGTCGACGTCACAGTGTAACTTCACAGTGTGAG 360       370       380       390       400
CCAGGGCCTCGCAGTCTGTCAATCTGTGAGTGTCCTTTGAGACAGATACG
GGTCCCGGAGCGTCAGACAGTTAGACACTCACAGGAAACTCTGTCTATGC 410       420       430       440       450
GTCTCTTAGAGCACTGAAAGACAATCATAAGCCTGGTGGAAATGCCTA
CAGAGAATCTCGTGACTTTCTGTTAGTATTCGGACCACCTTTACGGAT
```

FIGURE 10a

```
         10        20        30        40        50
AAGCTTGTAAGACCTTTAGGGGAAAATGGACTGACAAAAACTGATTTTCC
TTCGAACATTCTGGAAATCCCCTTTTACCTGACTGTTTTGACTAAAAGG
HindIII
         60        70        80        90       100
AAGTTTAGCAAGTCCAAACAAGATTGTTGATCCCACAGAAGGAAATCTGA
TTCAAATCGTTCAGGTTTGTTCTAACAACTAGGGTGTCTTCCTTTAGACT 110       120       130       140       150
TTGTGTTACTTCGTGACTTCTACTATGGAGAGCTTATAGGAGTTGGGCAG
AACACAATGAAGCACTGAAGATGATACCTCTCGAATATCCTCAACCCGTC 160       170       180       190       200
CCAGAACCGAAGACCCACACAGCGTTTAAATGCCTCAGCTGCTTGAAAGT
GGTCTTGGCTTCTGGGTGTGTCGCAAATTTACGGAGTCGACGAACTTTCA 210       220       230       240       250
TCTAAAAAATGTCAAGTTTATGAATCACATGAAGCGCCATTTGGAACTTG
AGATTTTTTACAGTTCAAATACTTAGTGTACTTCGCGGTAAACCTTGAAC 260       270       280       290       300
AGAGGCAGAGAGGTGACAGCTGGAAAAACCACACCACCTGCCAGCACTGC
TCTCCGTCTCTCCACTGTCGACCTTTTTGGTGTGGTGGACGGTCGTGACG 310       320       330       340       350
CTCCGCCAGTTTCCTACTCCCTTCCAGCTGCAGTGTCACATTGAAAGTGT
GAGGCGGTCAAAGGATGAGGGAAGGTCGACGTCACAGTGTAACTTTCACA 360       370       380       390       400
CCACACTCCCCAGGGGCCCTCCGCAGTCTGTCAAATCTGTGAGTTGTCCT
GGTGTGAGGGGTCCCCGGGAGGCGTCAGACAGTTTAGACACTCAACAGGA 410       420       430       440       450
TTGAGACAGATCAGGTTCTCTTAGAGCACATGAAAGACAATCATAAGCCT
AACTCTGTCTAGTCCAAGAGAATCTCGTGTACTTCTGTTAGTATTCGGA 460       470       480       490       500
GGTGAAATGCCCTATGTATGCCAGGTTTGCAGTTACAGATCATCATTTTT
CCACTTTACGGGATACATACGGTCCAAACGTCAATGTCTAGTAGTAAAAA 510       520       530       540       550
TGCAGATGTGGATGCACATTTCCGAGCATGCCATGGTAACACTAAGAATT
ACGTCTACACCTACGTGTAAAGGCTCGTACGGTACCATTGTGATTCTTAA 560       570       580       590       600
TACTTTGCCCGTTTTGTCTCAAAATTTTTAAGACTGCAACAGCATACAGA
ATGAAACGGGCAAAACAGAGTTTTAAAAATTCTGACGTTGTCGTATGTCT
```

FIGURE 10b

```
           610        620        630        640        650
    CGTCATCATAGAGGGCACTGGGAAAAGAGTTTTCACCAGTGTTCCAAATG
    GCAGTAGTATCTCCCGTGACCCTTTTCTCAAAAGTGGTCACAAGGTTTAC 660        670        680        690        700
    TCGGCTACAGTTTTAACTTTCAAAGAGAAAAGGGAGCACAAGACCCAGT
    AGCCGATGTCAAAAATTGAAAGTTTCTCTTTTCCCTCGTGTTCTGGGTCA 710        720        730        740        750
    GTCATCAAATGTTTAAGAAGCCTAAGCAGCTAGAAGGATTGTCTCCTGAA
    CAGTAGTTTACAAATTCTTCGGATTCGTCGATCTTCCTAACAGAGGACTT 760        770        780        790        800
    ACAAAAGTTGTTATTCAGGTATCACTGGAACCCCTTCAAGCAGGATTGGT
    TGTTTTCAACAATAAGTCCATAGTGACCTTGGGGAAGTTCGTCCTAACCA 810        820        830        840        850
    GGAAATAGCATCCATTACTGTGAACACATCTGATTTTGAATCATCACCCA
    CCTTTATCGTAGGTAATGACACTTGTGTAGACTAAAACTTAGTAGTGGGT 860        870        880        890        900
    TCAAATCTAAAAGTAGGAGGTCAAAAAAGAAAAAAAAAGTTAATTCAGC
    AGTTTAGATTTTCATCCTCCAGTTTTTTTCTTTTTTTTTCAATTAAGTCG 910        920        930        940        950
    TTTCAGTAAGTCTGAAGCAAGTATTGCAGTCAAAGTTAAAAACCCCATTA
    AAAGTCATTCAGACTTCGTTCATAACGTCAGTTTCAATTTTTGGGGTAAT 960        970        980        990       1000
    AAAACAAAAAGATCAAATTATAGCATTATTCAGTAATATCAAATATAGGG
    TTTTGTTTTTCTAGTTTAATATCGTAATAAGTCATTATAGTTTATATCCC 1010       1020       1030       1040       1050
    AAAGCGATGGGTAATTTATGTGATTTGTTTTAAATACAGGAAGTACAAT
    TTTCGCTACCCATTAAATACACTAAAACAAAATTTATGTCCTTCATGTTA 1060       1070       1080       1090       1100
    TTTGTTTGATCTGCATATTGAGATGTTATTTAAAAATCTATTATCTGTTT
    AAACAAACTAGACGTATAACTCTACAATAAATTTTAGATAATAGACAAA 1110       1120       1130       1140       1150
    TTCATAAAATTGTCTTAACATGTAAAAGAATGTGTGCATGTGTGTGTGA
    AAGTATTTTAACAGAATTGTACATTTTCTTACACACGTACACACACACT 1160       1170       1180       1190       1200
    GAGAGAGAATGAGAGAAGTGGAGAAAGGAAAAGTAACAACCTATTTTGGT
    CTCTCTCTTACTCTCTTCACCTCTTTCCTTTTCATTGTTGGATAAAACCA
```

FIGURE 10c

```
         1210      1220      1230      1240      1250
ATTCGATGTTACTTGTAGGTTCGAAAGCTCTACTATACATATAATCTGTA
TAAGCTACAATGAACATCCAAGCTTTCGAGATGATATGTATATTAGACAT 1260      1270      1280      1290      1300
GAGTGTTTTAGCAACGTAGTTTTCAACTGTTTTCATGCCTTGAAGATCTC
CTCACAAAATCGTTGCATCAAAAGTTGACAAAAGTACGGAACTTCTAGAG 1310      1320      1330      1340      1350
AGTATCAGCTATATAGCCAGATTTGAATGTCACTCTCTGAAGTGCCTCTT
TCATAGTCGATATATCGGTCTAAACTTACAGTGAGAGACTTCACGGAGAA 1360      1370      1380      1390      1400
GGGCTGATCTAAGATAACCTGGCTCTGAAAGCATGCAGTGGAGAAGTTGA
CCCGACTAGATTCTATTGGACCGAGACTTTCGTACGTCACCTCTTCAACT 1410      1420      1430      1440      1450
TGGAGAAGCTCTGATGTGAGTTTGGACCAGACACGGGATTTAATAAGTGA
ACCTCTTCGAGACTACACTCAAACCTGGTCTGTGCCCTAAATTATTCACT 1460      1470      1480      1490      1500
AGAGCTGTGGCTTCTTGTCCCAGCTGAGGAAGAGCCATACATTCACTCCA
TCTCGACACCGAAGAACAGGGTCGACTCCTTCTCGGTATGTAAGTGAGGT 1510      1520      1530      1540      1550
GGCATAGAGCCAAGGTAGAAGGAACACTGTCTCAGAGTGCTTTTACCTAG
CCGTATCTCGGTTCCATCTTCCTTGTGACAGAGTCTCACGAAAATGGATC 1560      1570      1580      1590      1600
CCCAGGGACATCTCAAGGAAGCCAGCCGTTAAAATGCCTGTGTTTGGTGA
GGGTCCCTGTAGAGTTCCTTCGGTCGGCAATTTTACGGACACAAACCACT 1610      1620      1630      1640      1650
GAGAGCCTTGCAAGCATCAAGCAGGCCCTGTGTATCATTGACTGCAGTTG
CTCTCGGAACGTTCGTAGTTCGTCCGGGACACATAGTAACTGACGTCAAC 1660      1670      1680      1690      1700
GAGAAGCAGAGATAGTTAATAGAATGAGACCTGGTGCCTGTGGACCTCCT
CTCTTCGTCTCTATCAATTATCTTACTCTGGACCACGGACACCTGGAGGA 1710      1720      1730      1740      1750
GTTGAGTGATCAAAAGGGGAATTTGATTCATTTCATCCCCTTTGCCATTT
CAACTCACTAGTTTTCCCCTTAAACTAAGTAAAGTAGGGGAAACGGTAAA 1760      1770      1780      1790      1800
GGCTGGCCTGTAGTCACAATGAGGTAGGCATATCCCTGTCAGACACAGTA
CCGACCGGACATCAGTGTTACTCCATCCGTATAGGGACAGTCTGTGTCAT
```

FIGURE 10d

```
         1810      1820      1830      1840      1850
    GCAAAGCAAGTTAAAATTCCAAAAGGAAAAAGAGCCTTGACGTGCACTTT
    CGTTTCGTTCAATTTTAAGGTTTTCCTTTTTCTCGGAACTGCACGTGAAA 1860      1870      1880      1890      1900
    GATTTGTGCTGGACCCATAGTTTTAACTGAAAAGGATCAAACACAGGGAA
    CTAAACACGACCTGGGTATCAAAATTGACTTTTCCTAGTTTGTGTCCCTT 1910      1920      1930      1940      1950
    TCTGTTCAGCTTTTGAATTGGGCTAAATTGAGTTCTCTTACCCTTAAGCT
    AGACAAGTCGAAAACTTAACCCGATTTAACTCAAGAGAATGGGAATTCGA 1960      1970      1980      1990      2000
    ACAATGGAGTTGTCCAAGAATAGTAAATATAGTGGGTGAAAATAGTCCAG
    TGTTACCTCAACAGGTTCTTATCATTTATATCACCCACTTTTATCAGGTC 2010      2020      2030      2040      2050
    GGTGATTAAACCCTTTTTAGAACTCGTCCTTACCTTTTCCAGTTACATGT
    CCACTAATTTGGGAAAAATCTTGAGCAGGAATGGAAAAGGTCAATGTACA 2060      2070      2080      2090      2100
    GTCTTACCCTAGTTGAACACGTGAAGATTTCAGTTTTGTATCTTATCTTG
    CAGAATGGGATCAACTTGTGCACTTCTAAAGTCAAAACATAGAATAGAAC 2110      2120      2130      2140      2150
    CCTTGGACACAAATGTAGTACAGTTAACAGCTAATTCTCTGCGTGTGTAA
    GGAACCTGTGTTTACATCATGTCAATTGTCGATTAAGAGACGCACACATT 2160      2170      2180      2190      2200
    TTTCCCATTGTATCAAACTAATTGAGTTTCAGTCTTTCTTGACACAGTCT
    AAAGGGTAACATAGTTTGATTAACTCAAAGTCAGAAAGAACTGTGTCAGA 2210      2220      2230      2240      2250
    GATGTGCAAGAATTGTCTCATGTATTTCAGTAATTGTCAGGTCATAGAGT
    CTACACGTTCTTAACAGAGTACATAAAGTCATTAACAGTCCAGTATCTCA 2260      2270      2280      2290      2300
    TTTCCTTCCTCTAATGTGCGATTATACTTGTGGTAACCTTTTTCTTGCG
    AAAGGAAGGAGATTACACGCTAATATGAACACCATTGGAAAAAGAACGC 2310      2320      2330      2340      2350
    GTCTCCAAGGGCTGTTTCACAGACCTGTGGGGTTCCCTCTTAAGTATTGG
    CAGAGGTTCCCGACAAAGTGTCTGGACACCCCAAGGGAGAATTCATAACC 2360      2370      2380      2390      2400
    TTCCTGAACATCAGCACACTTGGCTGCCTCCGTAGGTTCTTGGAGTTGAA
    AAGGACTTGTAGTCGTGTGAACCGACGGAGGCATCCAAGAACCTCAACTT
```

FIGURE 10e

```
        2410      2420      2430      2440      2450
TCTCCTGGAGTTGAATGTTACCCCTTCTCCACTTCTGGCACAGATACCTA
AGAGGACCTCAACTTACAATGGGGAAGAGGTGAAGACCGTGTCTATGGAT 2460      2470      2480      2490      2500
GCAATCTCTGTGCACCATTCAAGGAAGCCCTATCTGTAGACCTGTGCCAG
CGTTAGAGACACGTGGTAAGTTCCTTCGGGATAGACATCTGGACACGGTC 2510      2520      2530      2540      2550
GAGAAATCTCTCCGTTTCCTCTTCCTTTCTCCTCCTCTTTGTCTCTCCCC
CTCTTTAGAGAGGCAAAGGAGAAGGAAAGAGGAGGAGAAACAGAGAGGGG 2560      2570      2580      2590
ACTTCTCCCATCCTCAATTTATTTAAGTCCTCTAAGCTT
TGAAGAGGGTAGGAGTTAAATAAATTCAGGAGATTCGAA
                                  HindIII
```

FIGURE 11

```
         10        20        30        40        50
GTGACTACTCAGCNANGCACACCAGACAGTGTTCATACCTCATTAAGCCA
CACTGATGAGTCGNTNCGTGTGGTCTGTCACAAGTATGGAGTAATTCGGT 60        70        80        90       100
TGTTCAGAATGGAGAATCTTATCCCAACACATTTTCTAACGGACAATGTC
ACAAGTCTTACCTCTTAGAATAGGGTTGTGTAAAGATTGCCTGTTACAG 110       120       130       140       150
ATTGCAAACCTATAAGCCCTTTAGGGTCAAATGGACTGACAAAGCTTTG
TAACGTTTGGATATTCGGGAAATCCCAGTTTACCTGACTGTTTTCGAAAC 160       170       180       190       200
CTTTCCAAGTGTAGCAAGTCAAAACAAGATTGTTGATCCCACAGAAGGCA
GAAAGGTTCACATCGTTCAGTTTTGTTCTAACAACTAGGGTGTCTTCCGT 210       220       230       240       250
ATCTGATTGTGTTACTCTGTGACTTCTACTATGGACAGCATATAGGAGAT
TAGACTAACACAATGAGACACTGAAGATGATACCTGTCGTATATCCTCTA 260       270       280       290       300
GGGGCAGCCAGAACCGAAAACTCACACAGCCTTTAAATGCCTCAGCTGCT
CCCCGTCGGTCTTGGCTTTTGAGTGTGTCGGAAATTTACGGAGTCGACGA 310       320       330       340       350
TGAAAGTTCTAAAAAATGTCAAGTTTATGAATCACATGAAGCACCATTTG
ACTTTCAAGATTTTTTACAGTTCAAATACTTAGTGTACTTCGTGGTAAAC 360       370       380       390       400
GAGCTTGAGAGGCAGAGAGGTGACAGCTGGAAATACCACACCACCTGCCA
CTCGAACTCTCCGTCTCTCCACTGTCGACCTTTATGGTGTGGTGGACGGT 410       420       430       440       450
GCACGTCAACTGCCAGTTTCCTACTCCCTTCCAGCTGCAGTGTCACATTG
CGTGCAGTTGACGGTCAAAGGATGAGGGAAGGTCGACGTCACAGTGTAAC 460       470       480       490       500
AAAGTGTCCATACTTCCCAGGAGCCCTCTGCAGTCTGTAAAATCTGTGAA
TTTCACAGGTATGAAGGGTCCTCGGGAGACGTCAGACATTTTAGACACTT 510       520       530       540       550
TTGTCCTTTTGAGACAGATCGGGTTCTCTAACAAGCACATGAAAA
AACAGGAAAACTCTGTCTAGCCCAAGAGATTGTTCGTGTACTTTT
```

FIGURE 12

```
         10        20        30        40        50
TCAGGTACTTCACTCTGAACTAATAGGCATAATCCAAAGGCCTAACTCAG
AGTCCATGAAGTGAGACTTGATTATCCGTATTAGGTTTCCGGATTGAGTC 60        70        80        90       100
TGATGGATTATAGGAGTCACATTCTTTAGCTTTGTCCCCTCCAGGTATTT
ACTACCTAATATCCTCAGTGTAAGAAATCGAAACAGGGGAGGTCCATAAA 110       120       130       140       150
TTCAAACAGTGACTACTCATCAAAGCACACCAGACAGTGTTCATACCTCA
AAGTTTGTCACTGATGAGTAGTTTCGTGTGGTCTGTCACAAGTATGGAGT 160       170       180       190       200
GTAAGCCATGTTCAGAATGGAGAATCTTGTCCAACACATTTTCCAAAGGA
CATTCGGTACAAGTCTTACCTCTTAGAACAGGTTGTGTAAAAGGTTTCCT 210       220       230       240       250
CAATGTCCATTGCAAGCCTATAAGTGCTTTAGGGTAAAATGGACTGACAA
GTTACAGGTAACGTTCGGATATTCACGAAATCCCATTTTACCTGACTGTT 260       270       280       290       300
AAATTGACTTTCCAAGTGTAGCAAGTCAAAACAAGATTGTTGATCCCACA
TTTAACTGAAAGGTTCACATCGTTCAGTTTTGTTCTAACAACTAGGGTGT 310       320       330       340       350
GAAGGCAATCTGATTGTGTTACTCTGTGATTTCTACTATGGACAGCATAT
CTTCCGTTAGACTAACACAATGAGACACTAAAGATGATACCTGTCGTATA 360       370       380       390       400
AGGAGATAGGCAGCCAGAACCGCAAACTCACACAGCCTTTAAATGCCTCA
TCCTCTATCCGTCGGTCTTGGCGTTTGAGTGTGTCGGAAATTTACGGAGT 410       420       430       440       450
GCTGCTTGAAAGTTCTAAAAAATGTCAAGTTTATGAATCACATCAAGCAC
CGACGAACTTTCAAGATTTTTTACAGTTCAAATACTTAGTGTAGTTCGTG 460       470       480       490
CATTTGGAGCTTGAGAGGNAGANAGGTNACAGCT
GTAAACCTCGAACTCTCCNTCTNTCCANTGTCGA
```

FIGURE 13a

BCY11a:

BRY4a:     CACCACAAATAGTGCCTAATAGCTTTTC.A...GAGTTATGTTC
                920       930       940       950
           ................  .......  ...........
OY11.1:    CACCACAAATAGTGCCTGATGGCTTTTCGAAGGAGTTATGTTC
              830       840       850       860       870

GRY1a:

10        20        30
           CTTCACAAGTTCATTGCAGCATCCAGTAGAAACAGCAG
           |||||||||||||||||||| |||||||||||||||||
        TCCTTTGATTACCTTCACAAGTTCATTGCAGGATCCAGTAGAAACAGCAG
              960       970       980       990       1000
           ...........||||||||| |||||||||||||||||||||||||
        TTCTTTGATTACCTTCACAAGGTCATTGCAGCATCCAGTAGAAACAGCAG
              880       890       900       910       920

40        50        60        70        80
        TTTCTGCAGGAGATATGGATAAAAGTCCTCGTGTATCAAAGCGACTTTCCA
        || ||||||||| |||||||||||||||||| ||||||||| |||||||||
       .TTATGCAGGAGCTATGGATAAAAGTCCTCATGTATCAAAGTGACTTTCCA
              1010      1020      1030      1040      1050
        |||||||||||||||||| ||||||||||||| ||||||||||| |||||
        TTTCTGCAGGAGATATGAATAAAAGTCCTCATGTATCAAAGCGAGTTTCCC
              930       940       950       960       970

90        100       110       120       130
        CTTCTGAAACAAATAGCACAAGTCCCAAAAGGCCTACACTCAGTGATGG.A
        ||||||||||||||||||||||||| |||||||||| || |||||||||||
        CTTCTGAAACAAATAGCACAAATCCCAAAAGGCCTAAACTCAGTGATGG.A
              1060      1070      1080      1090      1100
        ||| ||||||||||  ||| || ||||| ||||| || |||||||||||| |
        CTTGTGAAACAAATCGCAGAAATCCCAGAAGGCCTAAACTCAGTGATGGCA
              980       990       1000      1010      1020

FIGURE 13b

```
                150       160       170       180
     GTTATAGGAGAACATTCTTTAGCTTTGTCCCTTTCAGGTACTTTTCATAC
     |||||||||||||||||||||||||||||| || | ||| || |||||| ||
     ATTATAGGAGAACATTCTTTAGCTTTGTGCCCTCCAGATATTTTTCAAAC
        1110      1120      1130      1140      1150
     || | || |||||||||||||| ||| ||||  ||| ||  |||||||||
     .TTGTCGGGGAACATTCTTTAGGTTTCTCCCCGTCACGTTTTTTTCATAC
        1030      1040      1050      1060      1070

190       200       210       220       230
     AGTGACTACTCAGCAAAGCACACCAGACAGTGTTCATACCTCATTAAGCC
     ||||||||||||||||||||||||||||||||||||||||||||||||||
     AGTGACTACTCAGCAAAGCACACCAGACAGTGTTCATACCTCATTAAGCC
        1160      1170      1180      1190      1200
     || ||| ||||||||||||||||||||| |·||| ||||||||| ||||||
     AGAGACCACTCAGCAAAGCACACCAGACCGTGTCCATACCTCACTAAGCC
        1080      1090      1100      1110      1120

250       260       270       280
     ATGTTCAGAGTGGAGAACCTTGTCCAACAGCTTTTCCAAAGGAACATGTT
     ||||||||| ||||||| ||| ||||||| ||||| ||||||| ||||
     ATGTTCAGAATGGAGAATCTTATCCAACACATTTTCTAAAGGACAATGTC
        1210      1220      1230      1240      1250
     ||||||||| ||||||||||||||||||| ||||||||||||  ||||
     ATGTTCAGAATGGAGAACCTTGTCCAACACCTTTTCCAAAGGACAGTGTT
        1130      1140      1150      1160      1170

290       300       310       320       330
     CATTGCAAGCCTGTAAGTCCTTTAGGGGGAAATGTATTGACAAAAACTGA
     ||||||||| ||| |||| |||||||||  ||||| | ||||||||| |||
     CATTGCAAACCTATAAGCCCTTTAGGGTCAAATGGACTGACAAAAATTGA
        1260      1270      1280      1290      1300
     |||||||||||||||||| ||||||||| || || | ||||||||||||
     CATTGCAAGCCTGTAAGACCTTTAGGGGAAAGTGGACGGACAAAAACTGA
        1180      1190      1200      1210      1220
             |||| |||||| |||||||||| ||||| | ||||||||||||
             AAGCTTGTAAGACCTTTAGGGGAAAATGGACTGACAAAAACTGA
                10        20        30        40
```

FIGURE 13c

```
              350        360        370        380
      CTTTCCAAGTGTATCAAGTCAAAATAAGTTTGCTGATCCCACAGAAGGCA
      ||||||||||||| ||||||||| ||| ||| ||||||||||||||||||
      CTTTCCAAGTGTAGCAAGTCAAAACAAGATTGTTGATCCCACAGAAGGCA
            1310       1320       1330       1340       1350
       ||||||||| | |||||| ||| ||  ||| |||||||||||||||| |
       TTTTCCAAGTTTGGCAAGTCCAAACAAAATTGGTGATCCCACAGAAGGAA
            1230       1240       1250       1260       1270
       ||||||||| || |||||| ||| ||| ||| ||||||||||||||||  |
       TTTTCCAAGTTTAGCAAGTCCAAACAAGATTGTTGATCCCACAGAAGGAA
              50         60         70         80         90

390        400        410        420        430
      ATCTGATTGTGTTACTTCGTGACTTCTACTATGGACAGCATATAGGAGAT
      |||||||||||||||||  |||||||||||||||||||||||||||||||
      ATCTGATTGTGTTACTCTGTGACTTCTACTATGGACAGCATATAGGAGAT
            1360       1370       1380       1390       1400
       ||||||||||||||||||| |||||||||||||  |||||  ||||| |
       ATCTGATTGTGTTACTTCATGACTTCTACTATGGCGAGCATGGAGGAGTT
            1280       1290       1300       1310       1320
       |||||||||||||||||||||||||||||||||| ||| ||||||||  |
       ATCTGATTGTGTTACTTCGTGACTTCTACTATGGAGAGCTTATAGGAGTT
             100        110        120        130        140

450        460        470        480
      GGG.CAGCCAGAACCAAAAACTCACACAGCCTTTAAATGCCACAGCTGCT
      ||| ||||||||||| |||||||||||||||||||||||  ||||||||
      GGGGCAGCCAGAACCGAAAACTCACACAGCCTTTAAATGCCTCAGCTGCT
            1410       1420       1430       1440       1450
       ||| ||||||||| | || || ||||| || ||||||||| ||||||||
       GGG.CAGCCAGAAGCGAAGACCCACACCGCGTTTAAATGCCTCAGCTGCT
            1330       1340       1350       1360       1370
       ||| ||||||||| || || |||||||| ||||||||| ||||||||
       GGG.CAGCCAGAACCGAAGACCCACACAGCGTTTAAATGCCTCAGCTGCT
             150        160        170        180        190

490        500        510        520        530
      TGAAGGTTCTAAAAAATGTTGAGTTTATGAATCACATGAAGCACCATTTG
      |||| |||||||||||||||  ||||||||||||||||||||||||||||
      TGAAAGTTCTAAAAAATGTCAAGTTTATGAATCACATGAAGCACCATTTG
            1460       1470       1480       1490       1500
       |||| |||||||||||||||  ||||||||||||||||||||||||||||
       TGAAAGTTCTAAAAAATGTCAAGTTTATGAATCACATGAAGCACCATTTG
            1380       1390       1400       1410       1420
       |||| |||||||||||||||  ||||||||||||||||||||| ||||||
       TGAAAGTTCTAAAAAATGTCAAGTTTATGAATCACATGAAGCGCCATTTG
             200        210        220        230        240
```

FIGURE 13d

```
        540       550       560       570       580
GAACTTGAGAGGCTGAGAGGTGACAGCTGGAAATAC.ACACCACCTGCCA
 | ||||||||||| |||||||||||||||| ||| |||||||||||||
GAGCTTGAGAGGCAGAGAGGTGACAGCTGGAAATACCACACCACCTGCCA
       1510      1520      1530      1540      1550
|||||||||||| |||||||||||||||||  | |||||||||||||
GAACTTGAGAGGCAGAGAGGTGACAGCTGGAAAACCCACACCACCTGCCA
       1430      1440      1450      1460      1470
|||||||||||| |||||||||||||||||| || |||||||||||||
GAACTTGAGAGGCAGAGAGGTGACAGCTGGAAAAACCACACCACCTGCCA
        250       260       270       280       290

590       600       610       620       630
GCACTGCCACCGCCAGTTTCCTACGCCCTTCCAGCTGCAGTGTCATATTG
||||||| || ||||||||||||| ||||||| |||||||||||| ||||
GCACTGCAACTGCCAGTTTCCTACTCCCTTCCAGCTGCAGTGTCACATTG
       1560      1570      1580     .1590      1600
|||||||| |||||||||||||||| ||||||| |||||||||||| ||||
GCACTGCCTCCGCCAGTTTCCTACTCCCTTCCAGCTGCAGTGTCACATTG
       1480      1490      1500      1510      1520
|||||||| ||||||||||||||| ||||||| |||||||||||| ||||
GCACTGCCTCCGCCAGTTTCCTACTCCCTTCCAGCTGCAGTGTCACATTG
        300       310       320       330       340

640       650       660       670       680
AAAGTGTCCACACTTCCCAGGAGCCCTGCACAGTCTTGTAAAATCTGTGAA
|||||||||| |||||||||||||||| ||| || |||||||||||||
AAAGTGTCCATACTTCCCAGGAGCCCTCTGCAGTCT.GTAAAATCTGTGAA
       1610      1620      1630      1640      1650
|||||||||||| ||||||||||| |  | ||| || || | |||||||
AAAGTGTCCACACGGCCCAGGAGCCCTCCGCAGTCT.GTCACATCTGTGAG
       1530      1540      1550      1560      1570
|||||||||||| |||||| ||||| | ||| || || |||||||||
AAAGTGTCCACACTCCCCAGGGGCCCTCCGCAGTCT.GTCAAATCTGTGAG
        350       360       370       380       390

690       700       710       720       730
TTGTCCTTTGAGGCAGATCAGATTCTCTTACAGCACATGAAAGATAATCA
|||||||||||| |||||| | |||||| ||| |||||||||||||||
TTGTCCTTTGAGACAGATCGGGTTCTCTAACAGCACATGAAAGATAATCA
       1660      1670      1680      1690      1700
|||||||||||| ||||||| |||||||| | |||||||||||| |||||
TTGTCCTTTGAGACAGATCAGGTTCTCTTAGAGCACATGAAAGACAATCA
       1580      1590      1600      1610      1620
|||||||||||| ||||||| |||||||| | |||||||||||| |||||
TTGTCCTTTGAGACAGATCAGGTTCTCTTAGAGCACATGAAAGACAATCA
        400       410       420       430       440
```

FIGURE 13e

```
      740       750       760       770       780
 TAAGCCTGGTGAAATGCCCTATGTATGCCAGGTTTGCAGTTACAGATCAT
 ||||||||||||||||||||||||||||||||||||||||||||||||||
 TAAGCCTGGTGAAATGCCCTATGTATGCCAGGTTTGCAGTTACAGATCAT
       1710      1720      1730      1740      1750
 ||||||||||||||||||||||||||||||||||||||||||||||||||
 TAAGCCTGGTGAAATGCCCTATGTATGCCAGGTTTGCAGTTACAGATCAT
       1630      1640      1650      1660      1670
 ||||||||||||||||||||||||||||||||||||||||||||||||||
 TAAGCCTGGTGAAATGCCCTATGTATGCCAGGTTTGCAGTTACAGATCAT
        450       460       470       480       490

790       800       810       820       830
 CATTCTTTGCAGATGTGGATGCACATTTCAGAGCATACCATGGTAACACT
 ||||||||||||||||||||||||||||||||||||||||||||||||| |
 CATTCTTTGCAGATGTGGATGCACATTTCAGAGCATACCATGGTAACATT
       1760      1770      1780      1790      1800
 ||||  ||||||||||||||||||||||||||||||||||||||||||||
 CATTTTTTGCAGATGTGGATGCACATTTCAGAGCATACCATGGTAACACC
       1680      1690      1700      1710      1720
 ||||  |||||||||||||||||||||  |||||| ||||||||||||||
 CATTTTTTGCAGATGTGGATGCACATTTCCGAGCATGCCATGGTAACACT
        500       510       520       530       540

840       850       860       870       880
 AAGAATTTACTTTGCCCCTTTTGTCTCCAAATTTTTAAAACTGAAGCACT
 ||||  |||||||||||||||||| |||||   ||||||||| |  ||
 AAGAGTTTACTTTGCCCCTTTTGTCTTCAAATGTTTAAAACTGCAAGACC
       1810      1820      1830      1840      1850
 ||||||||||||||||| ||||||||| |||||||| |||||| | ||
 AAGAATTTACTTTGCCCGTTTTGTCTCAAAATTTTTCAAACTGCAACAGC
       1730      1740      1750      1760      1770
 ||||||||||||||||| ||||||||| ||||||||  |||| | ||
 AAGAATTTACTTTGCCCGTTTTGTCTCAAAATTTTTAAGACTGCAACAGC
        550       560       570       580       590

890       900       910       920       930       940
 ATACATATGTCATTATAAACAGCACTGGGCAAAGCGTTTTCACCAGTGTTC
 ||||||||||||||||| ||||||||||| ||||  ||||| ||||||||
 ATACATATGTCATTATAGACAGCACTGGGAAAAG..TTTTCATCAGTGTTC ᵪ
       1860      1870      1880      1890      1900
 ||||| | ||||| ||  | |||||||| |||| ||||||||||||||||
 ATACAGACGTCATCATCGAGGGCACTGGGAAAAGAGTTTTCACCAGTGTTC
       1780      1790      1800      1810      1820
 ||||| | ||||| ||| |  |||||||| |||| |||||||||||||||
 ATACAGACGTCATCATAGAGGGCACTGGGAAAAGAGTTTTCACCAGTGTTC
        600       610       620       630       640
```

FIGURE 13f

```
           950       960       970       980       990
      CAAATGTCGGCTACAATTTTTAACTTGTAAAGAGAAAAGGGAGCACAAGAC
      |||| || |||||||| |||||||||| |||||||||||  ||||||||||
      CAAATGTAGGCTACACTTTTTAACTTTTAAAGAGAAAAGACAGCACAAGAC
           1910      1920      1930      1940      1950
      |||||||||||||| ||||||||||   ||||||  |  |||||||||||
      CAAATGTCGGCTACAGTTTTTAACTACCAAAGAGGAGAGGGAGCACAAGAC
           1830      1840      1850      1860      1870
      ||||||||||||||| ||||||||||  ||||||||||||||||||||||
      CAAATGTCGGCTACAGTTTTTAACTTTCAAAGAGAAAAGGGAGCACAAGAC
           650       660       670       680       690

1000      1010      1020      1030      1040
      CCAGTGTCATCAAATGTTTAAGAAGCCTAAGCAGCTAGAAGGATTACCTC
      ||||||||||||||||||||||||||||||||| |||||||||||||||
      CCAGTGTCATCAAATGTTTAAGAAGCCTAAGCATCTAGAAGGATTACCTC
           1960      1970      1980      1990      2000
      |||||||||||||||||||||||||||||||||||||||||||||| |||
      CCAGTGTCATCAAATGTTTAAGAAGCCTAAGCAGCTAGAAGGATTGTCTC
           1880      1890      1900      1910      1920
      |||||||||||||||||||||||||||||||||||||||||||||| |||
      CCAGTGTCATCAAATGTTTAAGAAGCCTAAGCAGCTAGAAGGATTGTCTC
           700       710       720       730       740

1050      1060      1070      1080      1090
      CTGAAACAAAAGTTGTTATTCAGGTATCACTGGAACCCCTTCAACCAGGAT
      |||||||||| |||| || |||||||||| |||||||||||||| |||||
      CTGAAACAAGAGTTTTTTTTCAGGTATCACCGGAACCCCTTCAAC.AGGAT
           2010      2020      2030      2040      2050
      |||||||||| ||  ||||||| |||||| |||||||||||||  ||||||
      CTGAAACAAAAATTTTATTCAAGTATCAATGGAACCCCTTCAGCCAGGAT
           1930      1940      1950      1960      1970
      |||||||||||||||||||||||||||||||||||||||||||| ||||||
      CTGAAACAAAAGTTGTTATTCAGGTATCACTGGAACCCCTTCAAGCAGGAT
           750       760       770       780       790

1100      1110      1120      1130      1140
      TGGTGGAAGTAGCATCCATTACTGTGAACGCATCTGATTCTGAACCATCA
      |||| |||||||||||||| ||||||||||| ||||||||||||||||||
      TGGTGGAAGTAGCATCCAATACTGTGAACACATCTGATTCTGAACCATCA
           2060      2070      2080      2090      2100
      ||||.||||| |||||| |||||||||||| |||||||||  |||||||
      TGGTGGAAGTTGCATCCGTTACTGTGAACACATCTGATTTTGAATCATCA
           1980      1990      2000      2010      2020
      |||| ||| |||||||||||||||||||||| ||||||||||  |||||
      TGGTGGAAATAGCATCCATTACTGTGAACACATCTGATTTTGAATCATCA
           800       810       820       830       840
```

FIGURE 13g

```
         1150      1160      1170
CCCCCCAAATCTAAAAGTAGGAGGTCAAAAAAA...............C
 ||||||||||||||||||||||| |||||||                |
TCTCCCAAATCTAAAAGTAGGAGGCCAAAAAAAAAAAAAAACCAAAAAAC
         2110      2120      2130     2140      2150
||||||||||||||||| |||||||||||||||
CCCCCCAAATCTAAAAGGAGGAGGTCAAAAAAAGAAAAATAATA......
         2030     2040     2050     2060
|||  ||||||||||||||||||||||||||||
CCCATCAAATCTAAAAGTAGGAGGTCAAAAAAAGAAAAAAAA.......
         850       860       870       880

1180      1190      1200      1210      1220
CCGGTTAAGTCTACTTTAAGTAAGTCTGAAGCAAGTATTT....CAAAGT
 || |||||  |||||||| |||||||||||||||||||||    ||||||
CCCGTTAATTCTACTTTCAGTAAGTCTGAAGCAAGTATTTCAGTCAAAGT
         2160      2170      2180      2190      2200
     |||||  |||  |  ||  |||||||||||||||||||||      ||||||
...GTTAATTCTGCCTTCAGTAAGTCTGAAGCAAGTATTTCAGTCAAAGT
         2070      2080      2090      2100      2110
      |||||  ||    ||||  ||||||||||||||||||||||      ||||||
...GTTAATTCAGCTTTCAGTAAGTCTGAAGCAAGTATTGCAGTCAAAGT
         890       900       910       920       930

1230      1240      1250      1260      1270
TATAAACTCCATTAAAAACAAAAAATTCAA.CTATAGCATTATTCAATAA
|| ||||  |||||||||||||||||||||||||| |  |||  |||||||||||||
TAAAACCCCATTAAAAACAAAAAATTCAAATTTAGAATTATTCAATAA
         2210      2220      2230      2240      2250
 ||  |||   ||||||||||  |||||   ||||   ||||||||||||||||||||
TAAAAATCCCATTAAAAACCAAAAGATCAACTTATAGCATTATTCAATAA
         2120      2130      2140      2150      2160
 ||  ||||  ||||||||||||||||    ||||   |||||||||||||||   |||
TAAAAACCCCATTAAAAACAAAAGATCAAATTATAGCATTATTCAGTAA
         940       950       960       970       980

TAAA
||
TATCAAATATAGGGCAACCAATGTGTAATTTATGTGTTTTTGTTTTAAAT
         2260      2270      2280      2290      2300
||·············  ····  ···      ···············
TATCAAATATAGGGAAACCGATGGGTAATTTATGTGATTTTGTTTTAAAT
         2170      2180      2190      2200      2210
||·············  ··  ·   ···       ···············
TATCAAATATAGGGAAAGCGATGGGTAATTTATGTGATTTTGTTTTAAAT
         990       1000      1010      1020      1030
```

DETERMINATION OF GENETIC SEX IN RUMINANTS USING Y-CHROMOSOME SPECIFIC POLYNUCLEOTIDES

This application is a continuation of application Ser. No. 08/003,695, filed Jan. 13, 1993, now abandoned; which is a continuation of application Ser. No. 07/548,903, filed as PCT/AU89/00029, Jan. 29, 1989, now abandoned.

The present invention relates to determination of the primary (i.e. genetic) sex of individuals and of samples of cells removed from individuals, and is particularly concerned with ruminant sex determination using polynucleotides that are associated specifically with the Y chromosome.

(Note: References cited herein are collected at the end of the specification.)

The capacity to determine the sex of an embryo or a foetus is becoming increasingly advantageous, particularly in light of advances in the area of reproductive biology such as embryo transfer. In the dairy and beef cattle industry alone, some 50,000 embryo transplants were reported to have been carried out in 1985. Given the predisposition of the dairy industry to female progeny, it would be most advantageous if embryos could be routinely sexed in vitro prior to transfer into a maternal host. The availability of sexed embryos would allow dairy producers to select replacement progeny for their stock from embryos which possessed desirable traits, such as increased milk production and mothering ability. Similarly, in the sheep and goat industries, the availability of sexed embryos would enable producers to select the most desirable progeny for their stock.

The ability to determine the sex of an embryo or foetus in vivo is also important. In "conventional" pregnancies which do not involve embryo transfer, but rather arise via artificial insemination or natural insemination, the early determination of sex of an embryo or foetus would allow a producer to terminate a pregnancy if an embryo or foetus of the desired sex was not obtained.

The primary sex of a mammal is determined by the presence or absence of the entire Y-chromosome or a functional portion thereof. Gene(s) present on the Y-chromosome are responsible for the formation of the testis and the development of the male phenotype. The primary sex of an individual mammal is therefore dependent upon whether or not its genome contains certain DNA sequences, specifically those sequences comprising that part of the Y-chromosome which encode gene(s) responsible for testis determination.

The sex or presumptive sex of an individual mammal can therefore be determined by analysis for Y-chromosome specific genes in the DNA of the animal. Alternatively, sex can be determined by analysis for unrelated but genetically linked sequences that are associated specifically with the Y-chromosome. In order to minimise possible errors due to infrequent genetic recombination events, such analyses are best made for sequences which are closely linked to the testis-determining gene(s).

A number of investigators have identified DNA sequences which hybridize preferentially or exclusively to male DNA (1,2). These DNA sequences, however, have not been functionally characterized. Furthermore, it is unknown whether these sequences are capable of hybridization to non-human species.

Australian Patent Application No. 59561/86 discloses bovine DNA probes which hybridize preferentially to male DNA. These DNA sequences are stated to be useful as hybridization probes for sexing in embryos and foetuses.

A particular disadvantage associated with the DNA sequences described in Australian Patent Application No. 59561/86 is that they are species specific, i.e. bovine specific, and do not hybridize to DNA from other ruminant animals such as sheep or goats. The species specificity of these sequences therefore, limits their usefulness as a general reagent for determining the sex of foetuses or embryos of ruminant animals.

International Patent Application No. PCT/AU87/00254, discloses a 307 base pair nucleic acid sequence designated BRY.1 comprising Y-chromosome-specific DNA which is capable of hybridizing, i.e. forming stable heterologous hybrids, with male bovine- and ovine-derived DNA but not with DNA isolated from female animals.

The DNA sequences of the present invention were discovered through their association with the BRY.1 sequence in the DNA of male ruminants. Certain of these sequences are more efficacious than BRY.1 for determining the genetic sex of reminant cells because they exist in much higher copy number, are present in multiple copies in males (upto 500 copies per cell), but not the females, of all domestic ruminant species, i.e. cattle, sheep and goats, and show stronger sequence similarity between individual elements that have been sequenced.

The present invention arises from the discovery of specific Y-chromosomal DNA sequences, all or part of which, are found in all mammals so far examined. In particular, all or a large part of these sequences are conserved among ruminants and have been found to be repeated in the Y-chromosome of all ruminant animals studied to date. The conservation of these DNA sequences throughout the Order Mammalia, the demonstration that one of these sequences (called OY11.1) encodes all or part of a structural gene that is expressed in ruminant testes, and the exclusive association of repeating units of these sequences with the Y-chromosome of various ruminant species (which constitutes evidence for suppression of genetic recombination between these sequence elements and a gene or genes associated with testis-determination and/or male fertility) implies their close linkage on the Y-chromosome to DNA sequences essential to the differentiation and development of fertile males.

According to one aspect of the present invention, there is provided nucleic acid isolates capable of hybridizing only to Y-chromosome specific DNA species of cattle, sheep, goats, and other ruminants. The nucleic acid isolates correspond to all or part of a DNA sequence found on the Y-chromosome of at least one of bovine, ovine and caprine animals.

In particular, there are provided and defined a number of DNA isolates from male sheep that are capable of hybridizing only to samples of nucleic acid of cattle, sheep, goats and other ruminants which contain Y-chromosomal DNA sequences. The nucleic acid isolates correspond to DNA sequences comprising part of the Y-chromosomal DNA of ovine animals, referred to hereinafter as OY1.1, OY4.1, OY4.2, OY9.1, OY9.2, OY9.5 and OY11.1, respectively.

Additionally, there are provided and defined five DNA isolates from male cattle which are similar to portions of OY11.1 in nucleotide sequence, in their ability to form stable heterologous hybrids with similar portions of OY11.1 under standard conditions of high-stringency DNA/DNA hybridization, and in their ability to hybridize only to the DNA of cattle, sheep, goats and other ruminants which contain Y-chromosomal DNA sequences, and are referred to hereinafter as BRY.4a, BRY.4b, BRY.4c, BRY.4d and BRY.4e, respectively.

There are further provided and defined herein two DNA isolates from male goat which are similar to portions of OY11.1 in nucleotide sequence, in their ability to form stable heterologous hybrids with similar portions of OY11.1 under standard conditions of high-stringency DNA/DNA hybridization, and in their ability to hybridize only to the DNA of cattle, sheep, goats and other ruminants which contain Y-chromosomal DNA sequences, and are referred to hereinafter as GRY.1a and GRY.1b, respectively.

The OY1.1 DNA sequence is shown in FIG. 1. This sequence comprises 3,142 base pairs of nucleotides, with those numbered 2,171–2,475 inclusive being similar to the 307 base pairs of Y-specific DNA sequence BRY.1 to the extent that it can form stable heterologous hybrids with BRY.1 under standard conditions of high-stringency DNA/DNA hybridization and its determined sequence of bases is similar to that of BRY.1. OY1.1 is a 3,142 base pair BamHI-EcoRI restriction fragment that was cloned into plasmids pTZ18u and pTZ19u (trademark Bio-Rad) from a recombinant bacteriophage (λOGY1) containing approximately 17,200 base pairs of ram genomic DNA. Bacteriophage λOGY1 was identified and isolated from an unamplified library of ram genomic DNA by virtue of its hybridization to a 3,500 base pair (approx.) fragment of bovine genomic DNA containing BRY.1DNA, designated BRY.1 (BRY.S is a BamHI fragment contained within a recombinant bacteriophage isolated from an amplified library of bull genomic DNA: the specific recombinant was isolated by virtue of its hybridisation with BRY.1, as was the BRY.S fragment itself). The restriction fragment OY1.1 was sub-cloned in consequence of its being found to hybridize with BRY.1. It was subsequently shown by Hybridization to Southern blots of genomic DNA from individual male and female mammals to be generally conserved, male-specific and repeated in ruminants.

OY4.1 (FIG. 2) is a 2,552 base pair HindIII-BamHI restriction fragment that was cloned from a recombinant bacteriophage (λOGY4) containing approximately 12,900 base pairs of ram genomic DNA. Bacteriophage λOGY4 was identified and isolated from the unamplified library of ram genomic DNA by virtue of its hybridization to BRY.S. The restriction fragment OY4.1 was sub-cloned in consequence of its being found to hybridize with BRY.1. It was subsequently shown by hybridization to Southern blots of genomic DNA from individual male and female mammals to be generally conserved, male-specific and repeated in ruminants. The restriction fragment was blunt-ended with the large (Klenow) fragment of E. coli DNA polymerase I and cloned into the SmaI site of plasmid pTZ18u.

OY4.2 (FIG. 2) is a 1,076 base pair BamHI-BamHI restriction fragment that was cloned from the recombinant bacteriophage λOGY4. The restriction fragment OY4.2 was sub-cloned in consequence of its being adjacent to OY4.1 and being found to hybridize with BRY.S but not with BRY.1. The restriction fragment was blunt-ended with the large (Klenow) fragment of E. coli DNA polymerase I and cloned into the SmaI site of plasmid pTZ18u.

OY9.1 is a 2,555 base pair HindIII-BamHI restriction fragment (corresponding to base pairs 1071 and 3625 of FIG. 3) that was cloned from a recombinant bacteriophage (λOGY9) containing approximately 13,100 base pairs of ram genomic DNA. Bacteriophage λOGY9 was identified and isolated from the unamplified library of ram genomic DNA by virtue of its hybridization to BRY.S. The restriction fragment OY9.1 was sub-cloned in consequence of its being found to hybridize with BRY.1. It was subsequently shown by hybridization to Southern blots of genomic DNA from individual male and female mammals to be generally conserved, male-specific and repeated in ruminants. The restriction fragment was blunt-ended with the large (Klenow) fragment of E. coli DNA polymerase I and cloned into the SmaI site of plasmid pTZ18u.

OY9.2 (FIG. 3) is a 1,076 base pair BamHI-BamHI restriction fragment that was cloned from the recombinant bacteriophage λOGY9. The restriction fragment OY9.2 was sub-cloned in consequence of its being adjacent to OY9.1 and being found to hybridize with BRY.S but not with BRY.1. It was subsequently shown by hybridization to Southern blots of genomic DNA from individual male and female mammals to be generally conserved, male-specific and repeated in ruminants. The restriction fragment was blunt-ended with the large (Klenow) fragment of E. coli DNA polymerase I and cloned into the SmaI site of plasmid pTZ18u.

OY9.5 (FIG. 3) is a 6,933 base pair EcoRI-BamHI restriction fragment that was cloned into plasmid pTZ18u from the recombinant bacteriophage λOGY9. The restriction fragment OY9.5 was sub-cloned in consequence of its subtending OY9.1, with which it shares the BamHI terminus, and a number of 124 base pair tandem repeats adjacent to the HindIII terminus of OY9.1.

The OY11.1 DNA sequence comprising 3,983 nucleotide pairs is shown in FIG. 4. OY11.1 is an EcoRI-EcoRI restriction fragment of a recombinant bacteriophage (λOGY11) containing approximately 18,100 base pairs of ram genomic DNA. Bacteriophage λOGY11 was identified and isolated from an unamplified library of ram genomic DNA by virtue of its hybridization to BRY.S. The restriction fragment was blunt-ended with the large (Klenow) fragment of E. coli DNA polymerase I and cloned into the SmaI site of plasmid pTZ18u.

The restriction fragment OY11.1 was cloned in consequence of its being found to hybridize with a discrete species of polyadenylated RNA in the testes of foetal cattle, and was subsequently shown by hybridization to Southern blots of genomic DNA from individual male and female mammals to be generally conserved, male-specific and repeated in ruminants. It was also found to hybridize to Southern blots of genomic DNA of all mammals examined, but in a manner indicative of one or a small number of copies/genome.

Of the nucleic acid isolates from the Y-chromosome of bovine animals, BRY.4a(d) (FIG. 11) is 545 base pairs and is similar to bases numbered 1,074–1,613 in OY11.1 and BRY.4c(i) (FIG. 12) is 484 base pairs and is similar to bases numbered 950–1,449 in OY11.1 BRY.4a(d) and BRY.4c(i) are portions of two independent 4,000 base pair (approx.) HindIII restriction fragments (BRY.4a and BRY.4c, respectively) that were resected into plasmid pTZ19u from recombinant bacteriophage (λBGY1 and λBGY2 respectively) which contained approximately 15,000 base pairs of bull genomic DNA. The DNA sequences of BRY.4a and BRY.4c are shown in FIGS. 5 and 6, respectively. The complete sequences of BRY.4b, 4d and 4e (not shown) are greater than 90% homologous with BRY.4a and BRY.4c.

Bacteriophage λBGY1 and λBGY2 were identified and isolated from an unamplified library of bull genomic DNA by virtue of their hybridization with OY11.1. The restriction fragments BRY.4a and BRY.4c were sub-cloned in consequence of both their hybridization to OY11.1 and their apparent identity in size to similarly hybridizing HindIII fragments of three additional independent recombinant bacteriophage (λBGY3, λBGY4 and λBGY5, respectively) isolated similarly from the bull library.

The DNA sequences of GRY.1a and GRY.1b are shown in FIG. 10. Contained within these sequences are two smaller fragments designated GRY.1a(a) (384 base pairs, similar to bases numbered 1,186–1,575 in OY11.1) and GRY.1b(a) (448 base pairs, similar to bases numbered 1,183–1,642 in OY11.1) and the sequences of which are shown in FIGS. 8 and 9, respectively. GRY.1a(a) and GRY.1b(a) are HindIII restriction fragments of GRY.1a and GRY.1b, respectively, that were resected into plasmid pTZ19u from recombinant bacteriophage (λCGY1 and λCGY2, respectively) which contained approx. 15,000 base pairs of male goat genomic DNA. Bacteriophage CGY1 and λCGY2 were identified and isolated from an unamplified library of male goat genomic DNA by virtue of their hybridization with OY11.1. The restriction fragments GRY.1a and GRY.1b were sub-cloned in consequence of both their hybridization to OY11.1 and their apparent identity in size to similarly hybridizing HindIII fragments of one additional independent recombinant bacteriophage (λCGY3) isolated similarly from the male goat library.

The DNA sequences described herein (FIG. 1–12) were determined by standard DNA sequencing techniques (17), which recombinant plasmids were transformed into *E. coli* strain JPA101 and infected with "helper" bacteriophage M13K07 to produce single-stranded recombinant plasmid molecules. The DNA sequences of these template molecules were determined by the Sanger chain termination procedure. The complete sequences were determined for both strands from a nested series of deletion recombinants generated by sequential erasure at one end of the insert by the combined actions of exonuclease III and S1 nuclease followed by re-circularization and transformation.

The terms "OY1.1", "OY4.1", "OY4.2", "OY9.2", "OY9.5", "OY11.1", "BRY.4a", "BRY.4b", "BRY.4c", "BRY.4.d", "BRY.4e", "GRY.1a", and "GRY.1b" refer to, where provided, the specific sequences set forth in FIGS. 1–12. These terms also include variants where nucleotides have been substituted, added to or deleted from the relevant sequences shown in FIGS. 1–12, as long as the variants hybridize with all or part of any of the sequences given in FIGS. 1–12 and diverge by no more than 25% from any of those sequences.

Such variants may be naturally occurring allelic and/or cis variants which may arise within a population of individuals by virtue of point mutation(s), deletion(s) or insertion(s) of DNA sequences, by recombination or by rearrangement, and are not restricted to ruminant species. Alternatively, such variants may be artificially produced, for example by site-directed mutagenesis, by deletion of fragments of DNA using exonuclease(s) and/or endonuclease(s) including restriction endonuclease(s), or by the addition of DNA sequences by ligating portions of DNA together, or by the addition of DNA sequences by templat-dependent and/or template-independent DNA polymerase(s).

The various DNA sequences described herein show a high degree of sequence conservation. For example, DNA sequences OY1.1; OY4.1; OY4.2; OY9.1; OY9.2; OY9.5 and OY11.1 share over 85% homology. DNA sequences OY11.1; BRY.4a; BRY.4b; BRY.4c; BRY.4d; BRY.4e; GRY.1a. and GRY.1b are similarly homologous.

The present invention also extends to any contiguous portion of 12 or more nucleotides of any and all of the sequences illustrated, hereinafter referred to as "oligonucleotides". Such oligonucleotides may be used as hybridization probes to detect any of the illustrated sequences or similar sequences in ruminant and non-ruminant species. Such oligonucleotides may be constructed synthetically using commercially available DNA synthesizers such as the Applied Biosystems 380A DNA Synthesizer, using standard methods. Oligonucleotides which comprise less than 12 nucleotides have limited effectiveness as hybridization probes.

According to a further aspect of the present invention, there is provided nucleic acid isolates comprising any contiguous portion of 12 or more nucleotides of any and all of the sequences claimed herein.

The present invention also includes recombinant DNA molecules constructed from all or part of the claimed sequences as defined above and a vector capable of propagation in host prokaryotic or eukaryotic cells for the purpose of cloning, amplification and/or expression of the claimed sequences.

Although such vectors are exemplified herein to be molecules such as pTZ18u or pTZ19u, the skilled artisan could use any number of a wide range of vector molecules depending on the intended use of the said nucleic acid sequences. Examples of other vector molecules can be found in reference (9), and include both eukaryotic and prokaryotic vectors, plasmids or bacteriophage molecules and shuttle vectors.

The present invention also extends to RNA molecules which correspond to part(s) or the total of any or all of the sequences claimed (where thymidine of the corresponding DNA sequence(s) is replaced by Uracil), including any contiguous portion of 12 or more nucleotides of such RNA sequence(s) corresponding to either or both of he complementary strands of the corresponding DNA sequences(s).

The nucleic acids of the invention may be utilized as hybridization probes, and may be labelled with radioactive markers such as $^{32}P$, $^{35}S$, $^{125}I$, $^{14}C$, $^{3}H$, or with non-radioactive markers such as biotinylated (deoxy)nucleotide(s), bromodeoxyuridine (replacing deoxythymidine), or sulphonated (deoxy)nucleotide(s) by known methods (3–8). Claimed oligonucleotides may also be used as hybridization probes, and as primers for the determination of Y-specific DNA sequence in intact genomic DNA or in fragments of Y-specific DNA using known methods. These oligonucleotides or derivatives thereof may also be useful in oligonucleotide mutagenesis of Y-chromosomal genes.

RNA corresponding to all or part of the sequences claimed (as described above) may be produced using in vitro transcription systems, utilizing for example the RNA polymerases of bacteriophage SP6, T3 or T7 (7,8).

The nucleic acid isolates of the present invention may be used as hybridization probes to detect Y-chromosome-specific DNA and RNA sequences and, hence, to determine the genetic sex of, for example, an embryo or foetus of ruminant species. Similarly, the nucleic acid isolates may be used to detect variations in amounts and/or minor variations in sequence of corresponding sequences in individual animals. Such analyses are useful in paternity testing.

The DNA of fractionated sperm may also be tested with the nucleic acid isolates of the present invention. Particularly, fractionation procedures that in theory or in fact may enrich for sperm bearing a Y-chromosome can be assessed using the nucleic acid isolates of the present invention.

Where the sex of an embryo, foetus or individual ruminant animal or the sex chromosome content of individual sperm or a population of sperm is to be determined, a sample of cells is removed for assay. DNA and/or RNA may be extracted therefrom using known methods (9). The isolated DNA and/or RNA may then be applied and fixed directly to a membrane such as nitrocellulose, Nylon-66 (trademark DuPont) or a derivative thereof such as Hybond-N (trademark The Radiochemical Centre), including charge-modified derivative(s) such as Zeta-Probe membrane (trademark Bio-Rad). Alternatively, the DNA and/or RNA may be electrophoresed through a gel matrix and then transferred and fixed to a similar membrane.

The nucleic acids bound to the membrane are then hybridized with any or all of the nucleic acid isolates of the invention which is/are labelled with a detectable marker as hereinbefore described. Labelled isolate which binds to nucleic acid on the membrane is detected appropriately, for example by autoradiography (10). If the labelled isolate(s) hybridize(s) to similar sequences in the target sample, sex can be unequivocally designated male. In the above-described method, the target DNA of the embryo, foetus, and the like may be amplified according to the procedures of Saiki et al. (11,12).

According to a further aspect of the invention, nucleic acids are not extracted from the sample of cells removed for assay. The cells are heated in alkaline solution and the resultant solution is filtered directly onto a charge-modified nylon membrane such as Zeta-Probe membrane. DNA fixed to the membrane is hybridized with nucleic acid isolate(s) of the invention as described above.

According to a further aspect of the invention, there is provided a method for the determination of the sex chromosome constitution of a tissue or cell sample comprising, isolating DNA from said tissue of cell sample, immobilizing the isolated DNA onto a support matrix, hybridizing the immobilized DNA with a nucleic acid isolate capable of binding only to Y-chromosome specific DNA sequences, washing unbound nucleic acid isolate from the support matrix and subsequently detecting binding of said nucleic acid isolate to DNA bound to the support matrix.

According to another aspect of the present invention there is provided a method for determining the presence or absence of a Y-chromosome in fixed cells or interphase or metaphase chromosome spreads comprising, hybridizing said fixed cells or interphase or metaphase chromosomes with a nucleic acid isolate capable of hybridizing only to Y-chromosome specific DNA sequences of ruminants, under conditions enabling the nucleic acid isolate to bind to complementary DNA sequences, washing away unbound nucleic acid isolate, and detecting binding of the nucleic acid isolate standard techniques of in situ hybridization are used (13).

According to another aspect of the present invention there is provided a method for determining the sex chromosome constitution of a tissue or cell sample comprising isolating DNA from the tissue or cell sample and denaturing the isolated DNA to separate the respective coding and non-coding strands, annealing the denatured DNA with a synthetic oligonucleotide corresponding to 12 or more nucleotides from any of the claimed sequences, incubating the annealed DNA with DNA polymerase 1 to extend the oligonucleotide through the said sequences, if present in the tissue or cell sample; repeating this sequence as many times as desired to amplify levels of target DNA; and subsequently detecting the target DNA in the amplified sample either by:
(a) immobilizing the DNA onto a support matrix, hybridizing the immobilized DNA with a nucleic acid isolate capable of hybridizing only to Y-chromosome specific DNA sequences of ruminants which have been labelled with a detectable marker, under conditions enabling the labelled nucleic acid isolate to bind to complementary sequences, washing unbound isolate from the support matrix, and subsequently detecting binding of the nucleic acid isolate to DNA bound to the support matrix; or
(b) where labelled nucleotide precursors are included in the incubation with the DNA polymerase, fractionating the sample by electrophoresis in a gel matrix, and detecting labelled target DNA sequences which are fractionated in the gel matrix.

Nucleic acid hybridizations are carried out under standard conditions according to the methods of Reed and Mann (14) and Maniatis et al. (9).

According to a further aspect of the invention, a portion of target DNA sequence in the sample of cells may be amplified by "polymerase chain reaction" (PCR). This procedure may be applied to the determination of sex in bovine embryos by using the oligonucleotide primers P11 and P12 defined in FIG. 8 to amplify the DNA sequence occurring between these sequences in target DNA. The amplified target sequences may be detected following their fixation to a nylon membrane by using a labelled oligonucleotide such as P13 or P14 (defined in FIG. 8) in hybridization analysis. Alternatively, the amplified target sequences may be electrophoresed through a gel matrix then transferred to a nylon membrane for hybridization analysis. The amplified target sequences may also be visualized in the gel matrix following electrophoresis and staining, for example, with a standard silver reagent or with ethidium bromide and visualization under ultraviolet light. Even more particularly, the present invention provides two universal sexing primers, USP1 and USP2 (FIG. 12), which can be used for PCR sexing of all three domestic ruminants.

The oligonucleotides used in the foregoing description of PCR sexing of bovine embryos are included by way of example only and may not be construed as being the only oligonucleotides derived from the sequences of FIGS. 1–12 that are claimed for hybridization analysis or for the application of PCR to the determination of sex in ruminant species.

The nucleic acid isolate of the present invention may comprise or form part of a kit for detecting the presence or absence of Y-chromosome specific sequences in a tissue or cell sample. The nucleic acid isolate may be labelled with detectable markers. Kits may include buffers for diluting reagents, labelled compound(s), and solid supports on which assays may be performed.

According to still a further aspect of the present invention, there is provided a method for the isolation of Y-chromosome specific DNA comprising:
(i) annealing single-stranded ruminant genomic DNA of male and female animals under conditions whereby repeated DNA sequences anneal but "single copy" sequences do not, where the DNA of males has been previously subjected to digestion with a restriction endonuclease generating cohesive tarmini and the DNA of females has been subjected to random fragmentation;
(ii) ligating the annealed DNA into a replicable vector which has been prepared with cohesive termini complementary to those of the male genomic DNA fragments;
(iii) transforming host cells with the replicable vector containing the annealed DNA; and
(iv) hybridizing the DNA of transformed host cells with a labelled DNA probe prepared from female ruminant genomic DNA, and identifying those host cells which contain ruminant genomic DNA which does not hybridize with the labelled probe.

DESCRIPTION OF THE DRAWINGS

The present invention will now be described, by way of example only, with reference to the following non-limiting drawings and examples, wherein:

FIG. 1 shows the double-stranded DNA sequence of ovine repeat element OY1.1 comprising 3,142 complementary base pairs. The sequence is written in single-letter code with the upper strand (that sequence immediately beneath numerals indicating number of base pairs) written as 5'→3' and the complementary (lower) strand written 3'→5' according to standard practice, where A refers to deoxyadenosine-5'-phosphate, C refers to deoxycytidine-5'-phosphate, G refers to deoxyguanosine-5'-phosphate, and T refers to deoxythymidine-5'-phosphate. The underlined sequence (base numbers 2,171–2,475 inclusive) is similar to the sequence of bovine repeat element BRY.1 described in International Patent Application PCT/US87/00254.

FIG. 2 shows the double-stranded DNA sequence of ovine repeat element OY4.1–4.2.

FIG. 3 shows the double-stranded DNA sequence of ovine repeat element OY9.2–9.5.

FIG. 4 shows the double-stranded DNA sequence of ovine repeat element OY11.1 comprising 3,983 base pairs. The sequences in double underline (base numbers 1,251–1,270 inclusive of the complement of base numbers 1,360–1,380 inclusive) are identical to the sequences of PCR primers P12 and P11, respectively; the sequences in single underline (the complements of base numbers 1,272–1,288 inclusive and 1,304–1,320 inclusive) are identical to those of the hybridization oligonucleotides P13 and P14, respectively.

FIG. 5 shows the double-stranded DNA sequence of bovine repeat element BRY.4a.

FIG. 6 shows the double-stranded DNA sequence of bovine repeat element BRY.4c.

FIG. 7 shows a comparison of sequences subtended by oligonucleotide primers used for genetic sex determination by PCR.

FIG. 8 shows the double-stranded DNA sequence of caprine repeat element GRY.1a(a) comprising 384 base pairs. The sequences in double underline (base numbers 65–85 inclusive and the complement of base numbers 174–194 inclusive) are identical to the sequences of PCR primers P12 and P11, respectively; the sequences in single underline (the complements of base numbers 87–102 inclusive and 118–134 inclusive) are identical to those of the hybridization oligonucleot4ides P13 and P14, respectively.

FIG. 9 shows the double-stranded DNA sequence of caprine repeat element GRY.1b(a) comprising 448 base pairs. The sequences in double underline (base numbers 68–88 inclusive and the complement of base numbers 178–198 inclusive) are identical to the sequences of PCR primers P12 and P11, respectively; the sequences in single underline (the complements of base numbers 90–106 inclusive and 122–138 inclusive) are identical to those of the hybridization oligonucleotides P13 and P14, respectively.

FIG. 10 shows the double stranded DNA sequence of caprine repeat elements GRY.1a and GRY.1b.

FIG. 11 shows the double-stranded DNA sequence of bovine repeat element BRY.4a(d) comprising 545 base pairs, written as for FIG. 1. The sequences in double underline (base numbers 178–198 inclusive and the complement of base numbers 289–309 inclusive) define the sequences of PCR primers P12 and P11, respectively; the sequences in single underline (the complements of base numbers 200–216 inclusive and 232–248 inclusive) define the sequences of hybridization oligonucleotides P13 and P14, respectively.

FIG. 12 shows the double-stranded DNA sequence of bovine repeat element BRY.4c(i) comprising 484 base pairs. The sequences in double underline (base numbers 285–305 inclusive and the complement of base numbers 395–415 inclusive) define the sequences of PCR primers P12 and P11, respectively; the sequences in single underline (the complements of base numbers 307–323 inclusive and 339–355 inclusive) define the sequences of hybridization oligonucleotides P13 and P14, respectively.

FIG. 13 shows a comparison of repeat elements BRY4a, OY11.1 and GRY1a with bovine testes cDNA BCY11a.

DEFINITIONS AND ABBREVIATIONS

DNA—deoxyribonucleic acid
RNA—ribonucleic acid
cDNA—complementary DNA (enzymatically synthesized from a mRNA sequence)
mRNA—messenger RNA
A—Adenine
T—Thymine
G—Guanine
C—Cytosine
U—Uracil
Tris—Tris (hydroxymethyl) aminomethane
EDTA—Ethylenediaminetetracetic acid
SDA—Sodium dodecylsulphate
psi—pounds per square inch
K.MES—potassium morpholinoethane-sulphonate
polynucleotide—single or double-stranded DNA or RNA

EXAMPLE 1

Preparation of Genomic Libraries

Portions of liver from male and female ruminants (e.g. cattle, sheep or goats) were collected at an abbatoir and immediately frozen in liquid nitrogen. Samples (0.8 g) of frozen liver from individual animals were homogenised in 8 ml of HB (0.1M NaCl, 10 mM Tris-HCl (pH 7.5 ), 1 mM EDTA). To each homogenate was added, with thorough gentle mixing, 2.2 ml of 0.5M EDTA and 1.22 ml of 20% (w/v) Sarcosyl. The suspensions were heated at 65° C. for 15 min with occasional gentle mixing, 11.6 g of solid CsCl was dissolved in each, then 1 ml of ethidium bromide (10 mg/ml) was added and mixed. The suspensions were transferred into 13.5 ml centrifuge tubes which were placed in a Beckman Ti80 rotor and centrifuged in a Beckman L8-80 ultracentrifuge at 45,000 rpm for 60 h at 25° C.

The pink band of concentrated DNA near the middle of the tube was recovered by side puncture (with an 18 g needle affixed to a 1 ml plastic syringe) and transferred to a capped tube. Ethidium bromide was removed by repeated extraction with butanol (previously equilibrated with saturated NaCl solution) and the resultant clear DNA solution was dialysed against 3×2 liters of TE (10 mM Tris-HCl, pH 8.0, 1 mM EDTA) at 4° C.

Preparation of Genomic DNA

Between 9 μg and 1 mg of DNA isolated from the liver was digested to completion with restriction endonuclease Sau3A1 under standard conditions, then extracted successively with phenol and ether. It was recovered by the addition of ammonium acetate to 2M and ethanol to 70% (v/v), mixing thoroughly, freezing in liquid nitrogen, thawing briefly, and centrifuging for 15 min at 4° C. The pellet of digested male DNA was then rinsed with 70% (v/v) ethanol and dried briefly in vacuo.

Preparation of Cloning Vector (plasmid pUCg) (15)

The cloning vector was prepared by digestion of 100 μg of plasmid pUC9 with restriction endonuclease BamHI, followed by the addition of SDS to 0.5% (w/v) and ⅙ volume of 1M Tris-HCl, pH 9.0, and incubation at 37° C. for 1 h with 40 μg of calf intestinal alkaline phosphatase (Boehringer ELISA grade). This solution was treated with phenol and DNA recovered by sodium acetate/ethanol precipitation as hereinbefore described. The restricted DNA was dissolved in TE/0.2% (w/v) Sarcosyl and layered onto a cold (4° C.) linear gradient of 2–25% (w/v) sucrose dissolved in TE/0.2% (w/v) Sarcosyl in a Beckman SW41 ultracentrifuge tube. The tube was centrifuged in a Beckman L8-80 ultracentrifuge at 36,000 rpm for 20 h at 4° C., then fractions of 0.5 ml were collected using a gradient fractionator (ISCO).

Samples (10 μl) of each fraction were electrophoresed in a 1.5% (w/v) agarose gel containing ethidium bromide (0.5 μg/ml) then photographed under ultraviolet illumination (302 nm) to allow visual identification of fractions containing linearised plasmid.

DNA was recovered from 20 μl samples of each gradient fraction above by precipitation with ammonium acetate/ethanol as described above. To these samples was added 50 μl of competent JM83 cells (see below), the suspensions were kept on ice for 30 min, heated at 42° C. for 90 sec, then mixed with 0.1 ml of 2YT medium and incubated at 37° C. for 1 h. Cells were recovered by centrifugation, resuspended in 0.2 ml of 2YT medium, plated on 2YT agar (2YT medium with 1.5% (w/v) agar) containing 50 μg/ml ampicillin and incubated at 37° C. overnight. Counting the number of colonies on each plate allowed identification of gradient fractions containing circular (uncut) plasmid.

Gradient fractions #13–16 (numbering started from top of gradient) containing a majority of linear, phosphatased plasmid and little circular plasmid (estimated from transforming ability) were pooled and the DNA recovered by precipitation with sodium acetate-ethanol as hereinbefore described.

Preparation of Competent Cells

Competent bacterial cells (*Escherichia coli* strain JM83) were prepared (16) by first inoculating 100 ml of 2YT medium (sterile 1.6% (w/v) Bacto-tryptone, 1% (w/v) yeast extract, 0.5% (w/v) NaCl, pH 7.4) with JM83 cells and incubating with vigorous shaking until the optical absorbance of the culture at 600nm was 0.4. The culture flask was chilled in ice/water for 5 min and the cells harvested by centrifugation. The pellet was resuspended in 50 ml of 50 mM $CaCl_2$, allowed to stand on ice for 20 min, then recentrifuged. The pellet was resuspended in 5 ml of cold 50 mM $CaCl_2$ and allowed to stand on ice for 24 h before being used for transformation assays.

Preparation of Library

Samples of genomic DNA (200 μg) and gradient-purified linear vector DNA (10 μg) were combined in 5 ml of ligation buffer (66 mM Tris-HCl, pH 7.5, 6.6 mM $MgCl_2$, 1 mM ATP, 100 μg/ml BSA (bovine serum albumin, Boehringer nuclease-free), 10 mM dithiothreitol, and 50 units of T4 DNA ligase (New England BioLabs)) and incubated overnight at 14° C.

Stocks of JM83 cells were prepared by dilution streaking a sample of cells onto LM agar (sterile 1% (w/v) Bacto-tryptone, 0.5% (w/v) yeast extract, 10 mM NaCl, 10 mM $MgSO_4$, 1.5% (w/v) agar) and incubating overnight at 37° C. A few isolated colonies were inoculated into 20 ml of pre-warmed SOB medium (sterile 2% (w/v) Bacto-tryptone, 0.5% (w/v) yeast extract, 10 mM NaCl, 2.5 mM KCl, 20 mM $MgSO_4$), the culture grown with vigorous aeration to an optical absorbance of 0.5 at 550 nm and diluted with 20 ml of sterile SOB:glycerol (60:40 by volume). Samples (0.1 ml) were transferred to 1.5 ml sealable tubes and chilled on ice for 10 min then frozen in dry ice/ethanol and stored at −70° C.

Competent JM83 cells were prepared from single colonies by first scraping a lump of frozen stock cell suspension onto LM agar, dilution streaking and incubating overnight at 37° C. Ten 2.5 mm (diameter) colonies were each suspended in 1 ml of pre-warmed SOB medium by vortex mixing, the suspensions pooled in 90 ml of pre-warmed SOB medium, and the culture incubated with vigorous aeration at 37° C. until the optical absorbance at 550 nm was 0.5. The culture was transferred to 2×50 ml centrifuge tube, chilled on ice/water for 15 min, then the cells harvested by centrifugation at 4° C. (2,500 rpm for 12 min). The cell pellet was resuspended in 33 ml of ice-cold TEB (sterile 10 mM K-MES (Sigma), pH 6.3, 100 mM $RbCq$, 45 mM $MgCl_2$, 10 mM $CaCl_2$, 3 mM hexamine cobalt trichloride (Fluka)) and allowed to stand on ice for 15 min. The suspension was centrifuged at 4° C. (2,500 rpm for 10 min) and the pellet resuspended in 8 ml of ice-cold TEB. To the suspension was added 0.28 ml of DMSO (dimethyl sulphoxide, Merck spectroscopic grade) and the mixture swirled and allowed to stand on ice for 5 min, then 0.28 ml of 2.25M dithiothreitol (Calbiochem; sterile solution in 40 mM potassium acetate, pH6) was added and the cells again swirled and allowed to stand on ice for a further 10 min. Finally, 0.28 ml of DMSO was added and mixed in gently and cells again allowed to stand on ice for 5 min.

Samples of cells (210 μl) were transferred into 24 chilled polypropylene tubes with 10 μl of ligated DNA and the tubes were mixed gently and allowed to stand on ice for 30 min. The tubes were then placed in a 42° C. water bath for 90 sec, transferred to ice/water for 2 min, and 0.8 ml of SOC medium (sterile SOB medium containing 20 mM glucose) added and the suspension incubated at 37° C. for 1 h with gentle shaking. The suspensions in 4 tubes were pooled and the cells spread uniformly onto an 82 mm diameter nitrocellulose filter disc (Schleicher & Schull) by vacuum filtration on a modified Buchner funnel. The disc was placed onto 2YT agar containing ampicillin (50 μg/ml) and incubated at 37° C. overnight. This procedure was repeated for all samples.

Approx. 1,500 colonies of transformed cells were evident on each filter following overnight incubation, giving a "library" complexity of approx. 9,000 for the 240 μl of genomic DNA used for transformation (equivalent to a total potential complexity of 187,500 transformants for the 5 ml of ligation mixture). The cells on the six filters were gently suspended in 10 ml of SOB medium containing ampicillin (50 μg/ml), the suspension made 20% (v/v) in glycerol, and 1 ml aliquots dispensed into sealed tubes, frozen in liquid nitrogen and stored at −70° C. as the genomic library.

EXAMPLE 2

Hybridization

Samples of genomic libraries prepared as in Example 1, each containing approx. 2,000 transformed cells, were diluted in 4 ml of 2YT agar/ampicillin at 37° C. Each filter ("master") was then used to prepare a replicate screening filter by placing it, colony surface uppermost, onto a pad of 2 sheets of filter paper (Schleicher & Schull 3MM) and covering it with a fresh nitrocellulose disc (that had been pre-wetted by placing it onto 2YT agar/ampicillin) followed by 2 sheets of 3MM filter paper. The "sandwich" was pressed firmly with a smooth, velvet-covered aluminium block and the upper 2 sheets of 3MM filter paper were then removed. The sandwich of two nitrocellulose discs (master and replica) was "keyed" by piercing it a number of times with a 22 g needle attached to a syringe containing water-proof black ink. The filters were then carefully peeled apart and the master filter returned to its 2YT agar/ampicillin plate for storage at 4° C. The replica filter was placed, colony surface uppermost, onto 2YT agar/ampicillin and incubated at 37° C. for approx. 4–6 h (until colonies had grown to a diameter of approx. 0.5 mm) then transferred to 2YT agar containing chloramphenicol (200 µg/ml) and incubated overnight a 37° C. to arrest cell growth without inhibiting plasmid replication (chloramphenicol amplification of plasmid copy number).

The replica filters were then transferred (colonies uppermost) for 5 min onto a pad of 4 sheets of 3MM filter paper that had been wetted uniformly with 0.5M NaOH, 1.5M NaCl. Excess liquid was blotted from the filters by transferring them to dry 3MM filter paper (taking care to maintain them in a horizontal orientation at all times to minimise spreading of plasmid DNA liberated from colonies by alkaline treatment) and the alkaline treatment repeated. The blotted filters were then treated twice successively with 0.5M Tris-HCl (pH 7.5), 1.5M NaCl for 5 min similarly to above. After brief blotting, they were allowed to stand on 3MM filter paper for 30 min. DNA liberated from colonies was fixed to the neutralised filters by heating them in a vacuum oven at 80° C. for 2 h. Cellular debris was then removed from the filters by washing them in 5×SSC (1×SSC is 0.15M NaCl, 15 mM Na$_3$.Citrate), 0.5% SDS at 50° C. for 1 h with continuous gentle shaking.

The washed filters were prehybridized overnight with continuous gentle agitation at 42° C. in hybridization solution (50% (v/v) formamide, 5×SSPE (1×SSPE is 0.18M NaCl, 10 mM sodium phosphate (pH 7.7), 1 mM EDTA), 1% (w/v) SDS, 0.5 mg/ml heat-denatured, sheared salmon sperm DNA (Sigma, dissolved at 10 mg/ml in distilled water and autoclaved), 0.5% (w/v) skim milk powder). The pre-hybridized filters were transferred to fresh hybridization solution containing radioactive probe DNA at 10 mg/ml and incubated at 42° C. overnight with continuous gentle agitation.

The radioactive probe DNA (e.g. BRY1 or OY11.1) was prepared by nick translation. The sample of DNA (0.2 µg) was pre-incubated with 25 mg/ml DNase I (*E. coli* deoxyribonuclease I) in a total volume of 40 µl containing 50 mM Tris-HCl 9 pH 7.5), 7.5 mM MgCl$_2$, 5 mM dithiothreitol, 0.1 mg/ml BSA, 20 µM dATP, 20 µM dGTP, 20 µM dTTP, and 100 µCi α-$^{32}$P dCTP (Amersham; approx. 3,000 Ci/mmol) at 15° C. for 20 min. During this time a minute sample (approx. 0.2 µl) was removed and applied to the origin mark on a small sheet (approx. 4×8 cm) of PEI-cellulose thin layer chromatography material (Merck). Following the pre-incubation, DNA polymerase I (Boehringer; approx. 5 units) was added and incubation continued at 15° C. for 20 min. The nick translation reaction was stopped by the addition of SDS to 1% (w/v) and EDTA to 20 mM, and a second minute sample removed and applied adjacent to the first on the PEI cellulose sheet. The thin layer chromatogram was developed in 0.75M potassium phosphate, pH 3.5, resulting in a separation of dCTP from DNA. The chromatogram was exposed to a sheet of X-ray film (Fuji Rλ) for 15 min. Development of the X-ray film allowed visual estimation of the efficiency of incorporation of α-$^{32}$P dCTP into DNA. This was subsequently quantitated by scintillation counting of appropriate areas of the chromatogram. Before its addition to the hybridization solution, the labelled DNA was recovered by precipitation with ammonium acetate-ethanol as described above then dissolved in distilled water and denatured by heating at 100° C. for 5 min.

Following hybridization, the nitrocellulose filters were rinsed briefly in 2×SSC at room temperature then washed in 2×SSC, 0.1% (w/v) SDS at room temperature for 15 min. with moderate agitation, followed by washing in 0.5×SSC, 1% SDS at 68° C. for 15 min., again with moderate agitation. They were finally rinsed briefly at room temperature in 0.5×SSC, blotted dry, wrapped in Gladwrap, and exposed to X-ray film (Fuji RX) with a DuPont Cronex "Lightning Plus" (Trademark) intensifying screen at −70° C. for 3 days.

Autoradiography signals on the developed X-ray film correspond to hybridization of recombinant plasmids in discrete colonies with nick translated DNA.

When appropriate "alkaline Southern blotting" was by the method of Reed and Mann (14).

Dot Blot hybridization was as follows: 8 µg of genomic DNA was diluted into 1 ml of 0.4M NaOH, 20 mM EDTA and heated at 100° C. for 10 min. One-half of this sample (0.5 ml) was transferred into 0.5 ml of 0.4M NaOH, 20 mM EDTA, and after mixing 0.5 ml of this dilution was again transferred into 0.5 ml of 0.4M NaOH, 20 mM EDTA, and the serial dilution repeated to generate 7 dilutions for each sample. The first, third, fifth and seventh samples (0.5 ml of each, containing respectively 4, 1, 0.25 and 0.0625 µg of DNA) were applied to a sheet of Zeta-Probe membrane using a dot-blot micro-filtration manifold (Bio-Rad). Following vacuum filtration, the sample wells were rinsed with 0.4 ml of 0.4M NaOH and the membrane neutralised and hybridized with nick-translated DNA as described above.

EXAMPLE 3

Sequence Analysis

Sequence analysis of the Y-chromosome-specific DNA's was performed as follows:

The inserts in plasmids were excised by digestion with the restriction endonucleases and purified by electrophbresis of the digest in low melting temperature (LMT) agarose (Marine Colloids "Sea-Plaque") followed by excision of an agarose slice containing the band of insert DNA, visualised under ultraviolet illumination following ethidium bromide staining as hereinbefore described. DNA was isolated from the gel slice by melting the agarose at 65° C. for 10 min, extracting twice with redistilled phenol, concentrating the solution with repeated butanol extractions, and precipitating the DNA with ammonium acetate/ethanol (procedures as described above).

The recovered inserts were ligated into the plasmid vectors pTZ18u and pTZ19u (Bio-Rad) which had been prepared by digestion with restriction endonucleases BamHI and HindlII followed by treatment with alkaline phosphatase (as described above). Samples of the ligation reactions were used to transform *E. coli* strain JPA101 (made competent with CaCl$_2$ treatment as described above) and the cells plated on 2YT agar/ampicillin for overnight incubation at 37° C. Colonies containing the desired recombinant plasmids were identified by restriction enzyme analysis, electrophoresis, alkaline Southern blotting hybridization (described above).

Single colonies were used to inoculate 5 ml cultures of 2YT medium/ampicillin (50 µg/ml). The bacteria were infected with bacterophage M13 strain KO7 (25 µl of phage stock containing $10^8$ pfu (plaque-forming units) and incubated for 1 h at 37° C. Kanamycin was added (70 µg/ml) and incubation continued overnight at 37° C. with vigorous aeration. The cultures were then centrifuged and the supernatants removed and treated with ribonuclease A (5 µg/ml) for 30 min. at 37°. Packaged single-stranded plasmid DNA was precipitated by the addition of 0.3 ml of polyethylene glycol (PEG) 6,000 (Kock-Light) in 2.5M NaCl. After mixing thoroughly and allowing to stand at room temperature for 15 min, the precipitates were recovered by centrifugation and the supernatants removed completely. The pellets were resuspended in 0.1 ml of TE and centrifuged briefly to remove particulate matter, then extracted with phenol and DNA recovered by precipitation from sodium acetate/ethanol as described above. The rinsed and dried pellets were used as templates for Sanger dideoxy sequencing reations (17).

The nucleotide sequences shown in FIGS. 1–13 are given in single letter code according to standard practice, where individual deoxyribonucleotides are denoted by the following letters: C=deoxycytidine-5'phosphate; G=deoxyguanosine-5'-phosphate; T= deoxythymidine-5'-phosphate; A=deoxyadanosine-5'phosphate.

EXAMPLE 4

Genetic Sex Determination by PCR

Table 1 provides the nucleotide sequence and properties of oligonucleotide primers used for genetic sex determination by PCR. The molecular weight of oligonucleotides is calculated from the molecular weight of individual bases as in DNA (sodium salt) with the addition of 1Na and 10H for the 5'- and 3'- termini.

The procedure used for sex determination using PCR is similar for cells derived from all domestic ruminant species (cattle, sheep, goats). The only differences are in the species of origin of the control and test cells and in the sequence of sexing and control oligonucleotide primers. Primers appropriate to each of the three different species are detailed in FIG. 7. The example described below is for cattle. Throughout, "tube" refers to the standard 1.5 ml Eppendorf polypropylene microcentrifuge tube with hinged lid.

1. All reagents are prepared previously and aliquots are stored frozen in liquid nitrogen.
   (a) Control cells: lymphocytes are prepared from peripheral blood of male and female animals by standard methods and are diluted to a concentration of $2\times10^3$/ml in PBS (phosphate buffered saline). The cell suspension is heated at 100° C. for 10 min then aliquoted at 20 µl per tube and frozen in liquid nitrogen.
   (b) 2×reaction mix:

| | |
|---|---|
| deionised water | 0.5 µl |
| 4 × buffer | 12.5 µl |
| dNTP mix | 8.0 µl |
| sexing primer SP11 (0.1 mM) | 0.5 µl |
| sexing primer SP12 (0.1 mM) | 0.5 µl |
| control primer CP16 (0.01 mM) | 0.5 µl |
| control primer CP22 (0.01 1M) | 2.0 µl |

The mix is aliquoted for freezing at 25 µl per tube. Individual components are as follows:

| | |
|---|---|
| 4 × buffer | 200 mM KCl |
| | 10 mM MgCl$_2$ |
| | 200 mM Tris |
| | 20 mM β-mercaptoethanol |
| | 4% (w/v) dextran T500 (Pharmacia) |
| | pH is adjusted to 8.6 with HCl |
| dNTP mix | 1.25 mM dATP |
| | 1.25 mM dCTP |
| | 1.25 mM dGTP |
| | 1.25 mM dTTP | where each of the four deoxynucleotide triphosphate solutions is prepared and frozen separately as a 10 mM stock in 10 mM Tris-HCl/0.5 mM EDTA. The pH of the final dNTP mix is adjusted to 8.5 with NaOH.

"Sexing primers" and "control primers" are described in Table 1 and FIG. 7.

"Taq DNA polymerase" is obtained from Biotech International Ltd. (Perth, Wash.).

2. Deionised water (25 µl) is added to negative control tubes (no sample controls).
3. Deionised water (20 µl) is added to male and female control tubes with 5 µl of frozen, heated lymphocyte suspension of the appropriate sex (refer above).
4. Deionised water (20 µl) is added to biopsy sample tubes and to each one is added a 5–10 cell biopsy of an embryo in 5 µl of culture medium.
5. Paraffin oil (65 µl) is added to all tubes.
6. Biopsy sample tubes are immediately heated at 100° C. for 10 min. During heating, 2× reaction mix aliquots sufficient for all tubes are thawed and mixed thoroughly.
7. Following removal of biopsy tubes from 100° C., 25 µl of 2× reaction mix is added to all tubes (above paraffin layer to minimise possibility of cross-contamination).
8. All tubes are centrifuged for 2–3 sec to consolidate and mix aqueous solutions.
9. All tubes are placed in a suitable rack and the rack is transferred to a 94° C. water bath for 1 min.
10. The rack is transferred immediately to a 65° C. water bath for 2.5 min.
11. Sequential incubation 5t these two temperatures is continued for a total of 35 cycles.
12. On completion of cycling the rack is removed to room temperature.
13. A sample (40 µl) of the aqueous phase in each tube is removed into a tube containing 11 µl of 5× stop solution.

| | |
|---|---|
| 5 × stop solution | 50 mM tris-HCl, pH 8.0 |
| | 100 mM EDTA |
| | 1% (w/v) Sarcosyl (Sigma) |
| | 7.5% (w/v) Ficoll 400 (Pharmacia) |
| | 0.05% (w/v) xylene cyanol. |

14. PCR reaction products are analysed by electrophoresis in an agarose gel that has been prepared during preparation of sample biopsies. The system used in the example is the bio-Rad wide mini-subcell with two (tandem) 20-slot sample combs. The gel is 100 ml of 3% (w/v) agarose (Sigma low EEO) in TAE bufer (40 mM Tris, 2 mM EDTA, pH adjusted to 8.0 with acetic acid) containing 0.5 µg/ml ethidium bromide. The tank buffer is identical to the gel buffer.
15. An aliquot (25 µl) of a solution containing 1 µl of DNA fragments of defined size is loaded into a single well of both the upper and lower sets of sample slots in the agarose gel.

DNA electrophoresis size markers: a sample of a plasmid pTZ19u (Bio-Rad) is digested to completion with the restriction endonuclease AluI under conditions recommended by the supplier and is mixed with ¼ volume of 5× stop solution (above) which also contains 0.05% (w/v) bromophenol blue.
16. An aliquot (25 µl) of each quenched control and test sample is loaded into a sample slot of the agarose gel.
17. Samples are electrophoresed at 100 V for 5 min, then at 200 V until the bromophenol blue in the marker slots has migrated 2–3 cm.
18. The gel is removed from the electrophoresis tank and is subjected to 304 nm ultraviolet irradiation on a transilluminator where it is photographed under standard conditions.
19. A band of pink fluorescence indicates the presence of DNA, the size of which is estimated by comparison with the size of the DNA marker fragments.

Negative control samples show no discrete band. Female positive control samples (lymphocytes) show a discrete band at approx. 230 bp. Male positive control samples show two discrete bands: one of approx. 230 bp and one of approx. 130 bp. The former results from PCR amplification of an autosomal satellite sequence common to the genomic DNA of animals of both sexes; the latter results from PCR amplification of a sequence that occurs in multiple copies only in the genomic DNA of male animals.

The sex of an embryo can be determined if the assay of its biopsy yields a discrete DNA band of approx. 230 bp. If this is the only discrete band observable, the sex of the embryo is female; if in addition to this band there is one of approx. 130 bp, the sex of the embryo is male.

Results of the control sample assays and of the "internal controls" (autosomal sequence amplification in biopxy sample) are critical to interpretation of the data. In the absence of a band at 230 bp in any sample, no determination can be made for that sample. If discrete bands at 230 bp and/or 130 bp are visible in the negative control sample, no determination can be made for any biopsy sample. If either or both of the positive control samples do not yield the anticipated result (refer above), no determination can be made for any biopsy sample.

This example should be interpreted to include the use of alternative procedures for thermal cycling and for PCR product identification. The former can be achieved through the use of programmable heating blocks (e.g. the Thermal Cycler sold by Cetus Perkin-Elmer and the Intelligent Heating Block sold by Hyb-Aid), although their optimal implementation requires modification of cycling temperatures and times according to the thermal gradients generated within the assay tubes. The latter includes the application of nucleic acid hybridization procedures, with or without prior electrophoresis of the PCR reaction products.

Variations in the number of cells used for assay and in the number of temperatures of thermal cycles may, of course, be made without affecting the efficiency of this method for sex determination.

Example of PCR Application to Cattle Embryo Sexing

Bovine embryos (late morula state) were asymmetrically divided into four sections. Different cell numbers per section permitted examination of assay sensitivity. Each section was assigned an arbitrary code number and assays were performed in double blind trials. Polymerase chain reaction as described above was used to amplify a bovine male-specific repeated DNA sequence; a control repeated autosomal sequence was amplified simultaneously, allowing for verification of both PCR amplification and successful transfer of biopsy cells into the assay tubes. Each sexing assay trial required approximately 3 hr to complete. Data are presented in the table below.

| TRIAL No. | EMBRYO No. | SECTION No. (a) | | | | ESTIMTED CELL No. (b) | | | | ASSAYED SEX (c) | | | |
|---|---|---|---|---|---|---|---|---|---|---|---|---|---|
| 1 | 1 | 3 | 4 | 18 | 22 | 4 | 6 | 6 | 6 | M | M | M | M |
| 1 | 2 | 1 | 7 | 13 | 15 | 8 | 10 | 8 | 6 | W | M | M | W |
| 1 | 3 | 8 | 17 | 23 | 25 | 12 | 8 | 14 | 4 | F | F | F | F |
| 1 | 4 | 2 | 10 | 29 | 31 | 6 | 7 | 9 | 7 | F | F | F | L |
| 1 | 5 | 11 | 16 | 20 | 28 | 2 | 12 | 8 | 12 | W | M | M | M |
| 1 | 6 | 6 | 9 | 26 | 32 | 6 | 12 | 12 | 12 | F | F | W | F |
| 1 | 7 | 5 | 12 | 27 | 30 | 7 | 10 | 12 | 10 | F | F | F | F |
| 1 | 8 | 14 | 19 | 21 | 24 | 10 | 10 | 10 | 12 | F | F | F | F |
| 2 | 1 | 1 | 13 | 15 | 31 | 12 | 14 | 12 | 10 | M | M | M | M |
| 2 | 2 | 2 | 5 | 11 | 23 | 12 | 14 | 8 | 14 | F | F | F | F |
| 2 | 3 | 6 | 16 | 18 | 26 | 10 | 14 | 7 | 20 | M | M | M | M |
| 2 | 4 | 4 | 17 | 19 | 24 | 14 | 7 | 29 | 15 | F | F | F | F |
| 2 | 5 | 8 | 22 | 16 | 28 | 20 | 20 | 16 | 4 | M | M | M | M |
| 2 | 6 | 20 | 21 | 25 | 29 | 12 | 8 | 15 | 15 | F | F | F | F |
| 2 | 7 | 12 | 14 | 30 | 32 | 15 | 12 | 12 | 6 | M | M | M | M |
| 2 | 8 | 3 | 7 | 9 | 10 | 4 | 9 | 12 | 20 | F | F | F | F |

(a) Number of cells per coded section is presented respectively in adjacent columns;
(b) Estimated cell number is ± 20%;
(c) Assay results are presented as F = female, M = male; W = weak signal, L = lost section.

Some blood in trial 1 produced signals too weak to interpret. An additional amplification cycle was used in trial 2 resulting i much stronger signals. The results of trial 2 demonstrate unequivocally the accuracy of the assay ($p=6\times 10^{-8}; X^2$).

To date, the assay described has yielded unequivocal data with embryo biopsies and lymphocytes from a variety of domestic breeds of cattle (including Hereford, Poll Hereford, Aberdeen Angus, Holstein/Friesian, Murray Grey, Limousin and Shorthorn) and sheep (Merino, Border Leicester and Dorset); with goats, only lymphocytes have been analysed (angora, Chashmere and fetal) with all assays similarly yielding unequivocal accurate data.

Advantages of the PCR technique described herein as a genreal procedure (not confined to sex determination) are:
(i) Constitution of the PCR reaction buffer, in particular the inclusion of the polysaccharide dextran (or similar). This novel component results in three unique advantages: firstly, its inclusion results in more efficient amplification leading to markedly higher sensitivity and specificity. Secondly, it allows the complete reaction mix (including the enzyme Taq DNA polymerase) to be prepared and stored frozen in a single tube resulting in a marked improvement in simplicity and quality control, with reduction in the possibility of on-site contamination. Thirdly, it eliminates the necessity for inclusion of an "inert" protein to stabilise the enzyme. Cognate PCR reaction mixes contain either gelatin or bovine serum albumin; since both are of animal origin there is a strong possibility that they may be contaminated with trace amounts of animal genomic DNA. Our experience has shown that either of these proteins from a variety of sources introduces artifacts into the PCR sexing assays.
(ii) Direct, simple analysis of embryo (any cell) biopsies wherein the sole sample preparation consists of heating the cells in water.
(iii) Judicious selection of oligonucleotide primer sequences such that the melting temperature ($T_m$) of hybrids formed between the primers and their complementary target sequences is approx. 70° C. in the solution used for PCR amplication. This has two major effects: firstly, PCR amplification is achieved by cycling for short periods between just two temperatures. The higher temperatures (94° C.) causes denaturation of complementary hybrids, and the lower temperature (65° C. in the application described above) allows primer annealing to target sequences at a temperature that is near the optimum for activity of Taq NA polymerase (approx. 72° C.). Secondly, annealing is done at high stringency, approx. 5° C. below the $T_m$ for primer target hybrids in the reaction solution. This effectively prohibits non-specific priming, resulting in markedly increased efficiency of specific target amplification with negligible background resulting from non-specific amplification.
(iv) The preceding features, in conjunction with the use of a higher than usual concentration of the enzyme Taq DNA polymerase, allow rapid and simple analysis of PCR reaction products by direct visualisation of amplified DNA following its electrophoresis and staining with a fluorescent dye.

BCY 11a

A cDNA library was constructed from the polyadenylated RNA (poly(A)RNA) fraction of bull testis.
1. RNA was extracted from a sample (1 g) of adult bull testis (that had been stored frozen in liquid nitrogen since biopsy) as described by Cathala et al (1983).
2. Poly(A)RNA was isolated from this RNA by affinity adsorption to ologo(dT)cellulose according to the procedure described by Nakazato and Edmonds (1974).
3. Single-stranded complementary DNA (ss cDNA) was prepared from a sample of the poly(A)RNA as follows:

A stock of concentrated reaction mix was prepared immediately before use by transferring into a sterile, chilled Eppendorf tube:

|  | Final conc. |
| --- | --- |
| 10 µl 1M tris-HCl, pH 8.3 | 50 mM |
| 8 µl 0.5M dithiothreitol | 20 mM |
| 1.5 µl 1M magnesium acetate | 7.5 mM |
| 10 µl 20 mM dATP | 1 mM |
| 10 µl 20 mM dGTP | 1 mM |
| 10 µl 20 mM dTTP | 1 mM |
| 2 µl 20 mM DCTP | 0.2 mM |
| 8 µl 5 mg/ml bovine serum albumin (nuclease-free; Boehringer) | 0.2 mg/ml |

Poly(A)RNA was recovered by centrifugation and the pellet rinsed with 70% ethanol (room tamp), dried briefly, and dissolved in sterile water at 1 mg/ml. A template/primer solution was prepared by transferring to a chilled, sterile Eppendorf tube:

| 19 µl sterile deionized water | |
| --- | --- |
| 5 µl 1 mg/ml poly (A)RNA | 0.1 mg/ml |
| 5 µl 0.2 mg/ml oligo(dT) (Boehringer) | 0.02 mg/ml |

The template was denatured by heating the mixture at 80° C. for 90 sac then immediately chilling in ice-water.

Remaining stock poly (A) RNA was immediately reprecipitated by adding ¹⁄₁₄ vol of sterile 3M sodium acetate (pH 5.5) and 2 vol of ethanol and storing at −20° C.

To the denatured, chilled template/primer solution was immediately added:

| 15 µl reaction mix | |
| --- | --- |
| µl [α-$^{32}$P]dCTP (5 mCi/ml, 3,000 Ci/mmol; Amersham Radiochemical Centre) | 0.1 mCi/ml |

The contents were mixed and centrifuged very briefly, and to it was added:

| 5 µl AMV reverse transcriptase (12,000–15,000 units/ml; Life Sciences) | 1,200–1,500 units/ml |
| --- | --- |

The contents were again mixed and centrifuged very briefly, then incubated at 42° C. for 60 min.

The reaction was quenched by adding:

| 2 µl 0.5M EDTA | 0.02 M |
| --- | --- |
| 1 µl 20% SDS | 0.4% |

The solution was extracted with an equal volume of equilibrated phenol, centrifuged and the upper aqueous phase removed into a clean tube. The aqueous phase was extracted with IAC (isoamyl alcohol:chloroform::1:24), centrifuged and recovered. The cDNA was precipitated by adding:

| | |
|---|---|
| 50 µl 4M ammonium acetate | 2 M |
| 200 µl ethanol | 2 vol |

The solution was frozen solid in liquid nitrogen, then thawed at room temperature and immediately centrifuged for 15 min at 4° C. The pellet was dissolved in TE buffer and the cDNA was reprecipitated with ammonium acetate/ethanol as above.

Double-stranded eDNA (ds eDNA) was synthesised from the as cDNA as follows (similar in principle to the procedure of Gubler and Hoffman (1983)):

Immediately before use, a stock of concentrated reaction mix was prepared by transferring into a sterile, chilled Eppendorf tube:

| | Final conc. |
|---|---|
| 365 µl sterile deionised water | |
| 20 µl 1M tris-HCl, pH 7.5 | 20 mM |
| 50 µl 1M MgCl$_2$ | 5 mM |
| 10 µl 1M (NH$_4$)$_2$SO$_4$ | 10 mM |
| 5 µl 2M KCl | 100 mM |
| 10 µl 20 mM dATP | 0.2 mM |
| 10 µl 20 mM dCTP | 0.2 mM |
| 10 µl 20 mM dGTP | 0.2 mM |
| 10 µl 20 mM dTTP | 0.2 mM |
| 10 µl 5 mg/ml bovine serum albumin (nuclease-free; Boehringer) | 0.05 mg/ml |

The double-precipitated product of first strand synthesis (ss cDNA/poly(A)RNA hybrid) was collected by centrifugation, rinsed with 70% ethanol, dried briefly, and redissolved in 42 µl of 50 mM Tris-HCl, pH 7.5. This gave a solution containing approx. 50 µg of ss cDNA/ml (i.e. 100 µg of hybrid/ml).

To a chilled, sterile Eppendorf tube was transferred:

| | |
|---|---|
| 50 µl reaction mix | |
| 42 µl cDNA/RNA template/primer solution | 0.04 mg/ml |
| 1 µl [α-$^{32}$P]dCTP | 0.1 mCi/ml |
| (5 mCi/ml, 3,000 Ci/mmol; Amersham Radiochemical Centre) | |

The contents were mixed and centrifuged very briefly, and to them was added:

| | |
|---|---|
| 3 µl e. coli Ribonuclease H | 30 units/ml |
| (1,250 units/ml; Boehringer) | |
| 2.5 µl E. coli DNA Polymerase I | 125 units/ml |
| (5,000 units/ml, nuclease-free; Boehringer) | |

The contents were again mixed and centrifuged very briefly, then incubated for 1 h at 12° C. followed by 1 h at 16° C. To the tube was then added:

| | |
|---|---|
| 1.5 µl E. coli Ribonuclease H | 30 units/ml |
| (1,250 units/ml; Boehringer) | | and incubation was continued at 16° C. for a fur=her 30 min.

The termini of the ds cDNA were then 'blunt-ended' by limited digestion with S1 nutlease:

To the tube was added 300 µl of freshly prepared S1 nuclease mix, containing 54 mM potassium acetate, pH 4.6
450 mM NaCl
1.8 mM ZnSO$_4$
9% (v/v) glycerol
90 units/ml S1 nutlease (Sigma)
and the tube was incubated for 60 min at 10° C.

Reaction was quenched by adding:

| | |
|---|---|
| 16 µl 0.5M EDTA | 0.02 M |
| 8 µl 20% Sarcosyl | 0.4% |

The solution was extracted with an equal volume of phenol and centrifuged to separate the phases. The upper aqueous phase was removed into a clean tube, extracted with IAC and centrifuged.

The aqueous phase was removed and concentrate to approx. 100 µl by repeated extraction with butan-1-ol. Excess butanol was removed by extraction with ether and the ds cDNA precipitated as above.

The pellet was dissolved in TE buffer and reprecipitated with ammonium acetate/ethanol. The cDNA was collected by centrifugation, rinsed with 70% ethanol, dried in vacuo, and dissolved in 50 µl of TE.

5. A sample (5 µg) of the plasmid vector BlueScript M13+ (StraLagene) was digested with the restriction endonuclease SmaI and treated with alkaline phosphatase. The blunt-ended, linearised, phosphatesad vector was then purified by electrophoresis in a gel of low melting temperature agerose (Marine Colloids 'Sea Plaque' agerose) from which it was recovered by excision of a gel slice which was melted and extracted twice with phenol. The Solution was concentrated with butanol and the purified DNA precipitated from the aqueous phase with acetate and ethanol as above.

6. A sample of the blunt-ended ds cDNA (approx. 0.2 µg) was treated with E. coli DNA polymerase I (Boabringer) and T4 polynucleotide kinase (Boehringer) under standard conditions (including the four dNTPs and ATP) to ensure that all fragments terminated in ligatable blunt ends. Following purification by phenol extraction and acetate/ethanol precipitation as described above, this material was ligated with prepared vector DNA.

Ligation mix (50 µl) was prepared as:
0.2 µg ds cDNA
1 µg linearised BlueScript vector DNA
50 mM Tris-HCl, pH 7.5
10 mM MgCl$_2$
7.5 mM dithiothreitol
100 µg/ml bovine serum albumin (nuclease-free; Boabringer)
1 mM ATP
1 mM spermidine (Sigma)
4 units T4 DNA ligase (BRL)
4 units T4 RNA ligase (BRL)
and incubated at 8° C. for three days. The product was purified by phenol extraction and acetate/ethanol precipitation as above, and redissolved in 10 µl of TE.

7. The purified ligation product was used to transform E. coli MC1061.1 cells by electrotransformation (Bill Dower, Bio-Rad; personal communication).

Competent cells were prepared by growing E. coli MC1061.1 in LB-broth with vigorous shaking at 37° C., to $A_{600}$ of 0.5 to 1. The culture flask was chilled briefly on ice/water and the cells were harvested by centrifugation at 4,000×$g_{max}$ for 15 rain at 4° C.

The cell pellet from 1 litre of culture was resuspended in 1 litre of cold deionised water and centrifuged as above, then resuspended in 500 ml of cold deionised water and recentrifuged. It was then resuspended in 20 ml of cold 10% glycerol, recentrifuged, and resuspended to approx. 3 ml (final volume) in cold 10% glycerol. This represented approx. 300-fold concentration from the culture, to a density of approx. $3\times10^{10}$ cells/ml. The final suspension was distributed in 100 µl aliquots, frozen in liquid nitrogen and stored at −70° C:

For transformation, an aliquot of the concentrated cells was thawed at room temperature and placed on ice. A sample (40 µl) was removed into a chilled Eppendorf tube and to this was added 1 µl of purified ligated DNA and the suspension mixed vigorously by flicking the tube.

The cell/DNA mixture was transferred into an ice cold 'GenePulser' (Bio-Rad) micro-cuvette (2 mm path length), and the cuvette was positioned in the chilled safety chamber of the GenePulser. The GenePulser was modified to include a 20 Ω resistor in series and a 200 Ω resistor in parallel with the sample. The instrument was set to 25 µF capacitance, 2.5 KV and pulsed once, generating a pulse of 12.5 KV/cm with a time constant of slightly less than 5 msec.

Immediately following the pulse, the cell suspension was removed from the cuvette and mixed into 1–2 ml of SOC medium (2% tryprone, 0.5% yeast extract, 10 mM NaCl, 2.5 mM KCl, 20 mM $MgSO_4$, 20 mM glucose) in a 17×100 mm polypropylene tube. The suspension was incubated with shaking (225 rpm) for 1 h at 37° C.

8. The cells were plated on selective medium (LB agar containing 20 µg/ml ampicillin) and incubated overnight at 37° C. The resultant colonies (approx. 50,000 total) were suspended in 20 ml of LB broth containing 20% glycerol and distributed in 1 ml aliquots into sealed tubes which were frozen in liquid nitrogen and stored at −70° C. This comprised the amplified library of adult bull testis cDNA.

9. Approx. 50,000 cells of the amplified library were spread onto six nitrocellulose filters on LB agar plates containing 20 µg/ml ampicillin and the plates incubated overnight at 37° C. Colonies were replicated for hybridisation screening according to the method of Hanahan and Messelson and duplicate replica filters were screened by hybridisation with plasmid pOY11.1.

Positive colonies (three) were isolated by repeated screening and subcloning. Plasmids contained within them were isolated according to Maniatis et al (1982) and were linearised by digestion with the restriction endonuclease BamHI and subjected to electrophoresis in an agarose gel.

The insert of the plasmid which contained the largest insert of the three recombinants recovered (approx. 1,400 bp; pBCY11a) was subjected to DNA sequence analysis (FIG. 13). The strong sequence similarity between this bovine cDNA (BCY11a) and the ovine genomic repeat element OY11.1 that led to its identification by hybridisation is evident from comparison of the two base sequences in FIG. 13.

By definition, BCY11a is the coding sequence of a structural gene that is transcribed in adult bull testis, a conclusion that is reinforced by its including a long open reading frame (FIG. 13). While its sequence is very similar to the sequence of genomic repeat elements associated with the DNA of male cattle, sheep and goats, it nevertheless shows significant differences from those sequences (FIG. 13). These include not only base substitutions but multiple frame shifts (deletions and insertions) which destroy the integrity of the open reading frame(s). From this it must be concluded that the similar genomic repeat elements that we have sequenced to date are not functional genes. This is reinforced by the linear similarity between BCY11a and the sequenced genomic elements: the majority of structural genes contain noncoding regions (introns) interspersed with coding regions (exons).

EXAMPLE 6

Universal Sexing Primers

Two oligomers designated USP1 (5'-CCCTTCCAGCTG-CAGTGTCA-3'; n=20; $T_H$=59° C.; $A_{260}$=192.9) and USP2 (5'-GATCTGTAACTGCAAACCTGGC-3'; n=22; $T_H$=61° C.; $A_{260}$=236.2) were selected for total homology between cloned BCY11a cDNA and all sequenced cattle, sheep and goat genomic repeats (see FIG. 13). These oligomers are used for PCR sexing of all three domestic ruminant species (cattle, sheep, goats). Amplification with these primers of target sequences is possible at 68°–70° C. as well as 65° C. and the total length of amplified segment is 173 base pairs.

It should be noted that the assay developed depends for its sensitivity on the detection of DNA sequences that are repeated hundreds of times in the DNA of the male genome, so that not one but hundreds of target sequences in each cell of the assay sample are amplified. Since non-functional repeated DNA elements tend to display substantially sequence variations (refer to FIG. 13), it is important to select as targets particular sequences in which variation is minimal. The identification of such regions, which are identical not only between non-functional genomic repeats but also with the analogous region of a functional gene from which those repeats presumably arose, suggests both the possibility of a cellular mechanism that minimises variation in these regions and the probability of these regions being strongly conserved within and between domestic ruminant species.

REFERENCES

1. Kunkel et al., Science 191, 1189–1190 (1976)
2. Bishop et al., Nature 303, 831 (1983)
3. Barone, et al. Nucleic Acids Res. 12, 4051–4061 (1984)
4. Caruthers, et al. Cold Spring Harbor Sym. Quant. Bio. 47, 411–418 (1982)
5. Cathala, et al. (1983) DNA 2, 329–335.
6. Rigy, et al., J. Mol. Biol. 113, 237–251 (1977)
7. Taylor, et al. Blochim. Biophys. Acta 442, 324–330 (1976)
8. Melton, et al. Nucleic Acids Res. 12, 7035–7056 (1984)
9. Lowary, et al. "Structure and Dynamics of RNA, NATO ASI Series 110" pp. 69–76, ed. van Knippeuberg, P. H. and Hilbers, C. W., Plenum Press, New York (1986)
10. Maniatis et al. (1982) Molecular Cloning, A Laboratory Manual, Cold Spring Harbor Laboratory
11. Swanstrom, R. and Shank, P. R. Anal. Blochem. 86, 184–192 (1978)
12. Saiki, et al. Science 230, 1350–1354 (1986)
13. Saiki, et al. Nature 324, 163–166 (1986)
14. Lederman et al. Anal. Blochem. 117, 158–163 (1981)
15. Reed, K. C. and Mann, D. A. Nucl. Acids Res. 13, 7207–7221 (1985)
16. Norgard, M. V., Tocci, M. J. and Monahah, J. J. (1980) J. Biol. Chem. 255, 7665–7672
17. Dagert, M. and Ehrlich, S. D. (1979) Gene 6, 23–28
18. Sanger, F., Nicklen, S. and Coulson, R. (1977) Proc. Natl. Acad Sci. USA 74, 5463–5467.
19. Gubler, U. and Hoffman, B. J. (1983) Gene 25, 263–269.

20. Maniatis, T., Fritxch, E. F. and Sambrook, J. (1982) "Molecular Cloning. A Laboratory Manual" (Cold Spring Harbor Laboratory) pp. 368–369.
21. Nakazato, H. and Edmonds, M. (1974) Meths. Enzymol. 29, 431–443.

TABLE 1

Sequence and Properties of Oligonucleotide Primers Used for Genetic Sex Determination by PCR

| Primer Type | Total length of PCR product (bp) | Primer Name | Primer Sequence (5' → 3') | | | | | | | G | C | A | T | M.W.[1] | $T_H$ (°C.)[2] | $A_{260}$ per µmol[3] | 1 $A_{260}$[3] (µM) |
|---|---|---|---|---|---|---|---|---|---|---|---|---|---|---|---|---|---|
| Control Primers: | | | | | | | | | | | | | | | | | |
| Cattle Satellite Ib | 226 | CP22 CP16 | GTG CGT | GAA TGT | GCA ACC | AAG TCG | AAC TGA | CCC GAA | GC ACC | 6 5 | 6 6 | 7 5 | 1 5 | 6,687 6,970 | 59 59 | 230.1 220.8 | 4.35 4.53 |
| Sheep Satellite I | 258 | CP23 CP24 | GGG CAC | TGT ACA | GAA AGG | GGA TCT | CCC TAG | TTT GCC | GG CC | 9 4 | 3 8 | 3 5 | 5 3 | 6,771 6,589 | 59 59 | 214.9 207.1 | 4.65 4.83 |
| Goat Satellite II | 226 | CP20 CP21 | GAT GGA | CTG GCC | GCA CTT | GAG GGA | TTC TGT | CTG GCA | GC AC | 7 7 | 5 5 | 3 4 | 5 4 | 6,691 6,700 | 59 59 | 206.1 213.2 | 4.85 4.69 |
| Sexing Primers: | | | | | | | | | | | | | | | | | |
| Cattle BRY.4 | 132 | SP11 SP12 | GAA GAT | CTT TGT | TCA TGA | AGC TCC | AGC CAC | TGA AGA | GGC AGG | 6 6 | 5 4 | 6 6 | 4 5 | 7,019 7,034 | 59 57 | 232.3 233.3 | 4.30 4.29 |
| Sheep OY11.1 | 124 | SP11 SP17 | GAA GAT | CTT CCC | TCA ACA | AGC GAA | AGC GGA | TGA AAT | GGC CTG | 6 5 | 5 5 | 6 8 | 4 3 | 7,019 7,012 | 59 57 | 232.3 243.1 | 4.30 4.11 |
| Goat GRY.1 | 130 | SP11 SP12 | GAA GAT | CTT TGT | TCA TGA | AGC TCC | AGC CAC | TGA AGA | GGC AGG | 6 6 | 5 4 | 6 6 | 4 5 | 7,019 7,034 | 59 57 | 232.3 233.3 | 4.30 4.29 |

[1]The molecular weight of oligonucleotides is calculated from the M.W. of individual bases as in DNA (Na$^+$ salt), with the addition of 1 Na and 1 OH (for the 5'- and 3'- termini): G = 351.2   C = 311.2   A = 335.2   T = 326.2
[2]The optimal hybridization temperature ($T_H$) for an oligonucleotide in a solution containing 1 M Na$^+$ can be calculated approximately with the following formula (note that optimal hybridization temperature is approx. 25° C. below the duplex melting temperature, $T_m$): $T_H = 4 \times (G + C) + 2 \times (A + T) - 5$ (°C.)
[3]The concentration of an oligonucleotide solution is calculated from its absorbence at 260 nm by using the following nucleotide-specific extinction coefficients: $A_{260}$ [G] = 11.7/µmol    $A_{260}$ [C] = 7.3/µmol    $A_{260}$[A] = 15.4/µmol    $A_{260}$[T] = 8.3/µmol

We claim:

1. An isolated nucleic acid capable of hybridizing only to Y-chromosome-specific DNA sequences of cattle, sheep and goats said isolated nucleic acid being selected from the group consisting of:
   (a) one or both strand of ovine repeat elements OY1.1, OY4.1, OY4.2, OY9.1, OY9.2, OY9.5 or OY11.1;
   (b) one or both strands of bovine repeat elements BRY4a, BRY4b, BRY4c, BRY4d, BRY4e, BRY4a(d) or BRY4c(i); and
   (c) one or both strands of caprine repeat elements GRY.1a, GRY.1a(a), GRY.1b or GRY.1b(a).

2. The isolated according to claim 1 comprising RNA corresponding to one or both strands of ovine repeat elements OY1.1, OY4.1, OY4.2, OY9.1, OY9.2, OY9.5 or OY11.1.

3. The isolated nucleic acid according to claim 1 comprising RNA corresponding to one or both strands of bovine repeat elements BRY4a, BRY4b, BRY4c, BRY4d, BRY4e, BRY4a(d) or BRY4c(i).

4. The nucleic acid isolate according to claim 1 comprising RNA corresponding to one or both strands of caprine repeat elements GRY.1a, GRY.1a(a), GRY.1b or GRY.1b(a).

5. The isolated nucleic acid according to claim 1 which is labelled with a detectable marker.

6. The isolated nucleic acid isolate according to claim 5 wherein the detectable marker is $^{32}$P, $^{14}$C, $^{3}$H, $^{125}$I, biotin or bromodeoxyuridine.

7. A recombinant vector comprising the isolated nucleic acid according to claim 1.

8. A method for the determination of the sex chromosome constitution of a tissue or cell sample and hence the sex of said sample comprising, isolating DNA from said tissue or cell sample, immobilising the isolated DNA onto a support matrix, hybridizing the immobilised DNA with a nucleic acid of claim 5, under conditions enabling the nucleic acid isolate to bind to complementary sequences, washing unbound nucleic acid from the support matrix, and subsequently detecting nucleic acid of claim 5 binding to DNA bound to the support matrix whereby binding indicates the presence of a Y-chromosome and absence of binding indicates the absence of a Y-chromosome.

9. A method for determining the presence or absence of a Y-chromosome in fixed cells or interphase or metaphase chromosome spreads comprising, hybridizing said fixed cells or interphase or metaphase chromosomes with the nucleic acid of claim 5, under conditions enabling the isolated nucleic acid to bind to complementary sequences, washing away unbound nucleic acid isolated, and detecting binding of the isolated nucleic acid to the fixed cells or interphase or metaphase chromosomes whereby binding indicates the presence of a Y-chromosome and absence of binding indicates the absence of a Y-chromosome.

10. A method for determining the sex chromosome constitution of a tissue or cell sample comprising isolating DNA from the tissue or cell sample and denaturing the isolated DNA to separate the respective coding and non-coding strands, annealing the denatured DNA with one or more synthetic oligonucleotides corresponding to the nucleic acid according to claim 1, incubating the annealed DNA with DNA polymerase to extend the oligonucleotides through the nucleic acid isolate DNA sequence if present in the tissue or cell sample; repeating this sequence as many times as is desired to amplify levels of the nucleic acid isolate and subsequently detecting the nucleic acid isolate sequences in the amplified sample, either by:

(a) immobilizing the amplified DNA onto a support matrix, hybridizing the immobilized DNA with the nucleic acid of claim 8 under conditions enabling the amplified DNA to bind to complementary sequences, washing unbound nucleic acid from the support matrix, and subsequently detecting binding of the nucleic acid of claim 5 to the amplified DNA bound to the support matrix, whereby detection of the amplified DNA is indicative of the presence of a Y-chromosome; or (b) where labelled nucleotide precursors are included in the incubation with DNA polymerase, fractionating the sample by electrophoresis in a gel matrix, and detecting labelled amplified DNA sequences as an indication of the presence of a Y-chromosome.

11. A method as claimed in claim 5 where the tissue or cell sample is obtained from an embryo, a foetus, or from sperm or a fraction of sperm.

12. A method as claimed in claim 5 wherein the isolated nucleic acid is labelled with a detectable marker.

13. A method as claimed in claim 12, wherein the detectable marker is $^{32}P$, $^{14}C$, $^{3}H$, $^{125}I$, biotin, or bromodeoxyuridine.

14. A kit for detecting the presence or absence of Y-chromosome specific sequences in a tissue or cell sample, comprising the isolated nucleic acid according to claim 1.

15. A kit as claimed in claim 14, additionally containing buffers for the dilution of reagents.

16. An oligomer for PCR sexing of ruminants specific for the Y-chromosome thereof comprising the sequence 5'-CCCTTCCAGCTGCAGTGTCA-3'.

17. An oligomer for PCR sexing of ruminants specific for the Y-chromosome thereof comprising the sequence 5'-GATCTGTAACTGCAAACCTGGC-3'.

* * * * *